(12) United States Patent
Malkowski et al.

(10) Patent No.: US 11,871,922 B2
(45) Date of Patent: Jan. 16, 2024

(54) ENDOSCOPIC STITCHING DEVICE

(71) Applicant: Covidien LP, Mansfield, MA (US)

(72) Inventors: Jaroslaw T. Malkowski, Trumbull, CT (US); Jacob C. Baril, Norwalk, CT (US)

(73) Assignee: COVIDIEN LP, Mansfield, MA (US)

( * ) Notice: Subject to any disclaimer, the term of this patent is extended or adjusted under 35 U.S.C. 154(b) by 400 days.

(21) Appl. No.: 17/352,718

(22) Filed: Jun. 21, 2021

(65) Prior Publication Data
US 2021/0378661 A1  Dec. 9, 2021

Related U.S. Application Data

(63) Continuation of application No. 16/142,015, filed on Sep. 26, 2018, now Pat. No. 11,058,413.

(Continued)

(51) Int. Cl.
 *A61B 17/04* (2006.01)
 *A61B 17/062* (2006.01)
 (Continued)

(52) U.S. Cl.
 CPC ...... *A61B 17/0469* (2013.01); *A61B 17/0491* (2013.01); *A61B 17/0625* (2013.01);
 (Continued)

(58) Field of Classification Search
 CPC ............ A61B 17/0469; A61B 17/0491; A61B 17/0625; A61B 17/2909;
 (Continued)

(56) References Cited

U.S. PATENT DOCUMENTS

| 1,037,864 A | 9/1912 | Carlson et al. |
| 1,131,163 A | 3/1915 | Saunders et al. |

(Continued)

FOREIGN PATENT DOCUMENTS

| EP | 0705569 A1 | 4/1996 |
| EP | 3703578 A1 | 9/2020 |

(Continued)

OTHER PUBLICATIONS

Japanese Office Action dated Jan. 12, 2023 corresponding to counterpart Patent Application JP 2018-228719.

(Continued)

*Primary Examiner* — Ashley L Fishback
(74) *Attorney, Agent, or Firm* — Carter, DeLuca & Farrell, LLP

(57) ABSTRACT

A stitching device includes a handle assembly and an elongate shaft assembly. The handle assembly includes a main rod and a drive conversion assembly including a cam wheel, a pivot block, first and second links, and a pawl. The pawl is operatively coupled to the main rod, and is configured to engage the pivot block to cause rotation of the pivot block which, in turn, causes reciprocating displacement of the first and second links. The elongate shaft assembly includes first and second blade drive members coupled to the cam wheel. The tool assembly includes first and second jaws and first and second blades. The first and second blades are operatively coupled with the respective first and second blade drive members, wherein axial displacement of the main rod transitions the first and second jaws between open and closed positions and causes reciprocating axial displacement of the first and second blades.

16 Claims, 40 Drawing Sheets

Related U.S. Application Data

(60) Provisional application No. 62/599,060, filed on Dec. 15, 2017.

(51) Int. Cl.
    *A61B 17/29*     (2006.01)
    *A61B 17/00*     (2006.01)
    *A61B 17/06*     (2006.01)

(52) U.S. Cl.
    CPC .. *A61B 17/2909* (2013.01); *A61B 2017/0046* (2013.01); *A61B 2017/00367* (2013.01); *A61B 2017/00371* (2013.01); *A61B 2017/00407* (2013.01); *A61B 2017/00424* (2013.01); *A61B 2017/00473* (2013.01); *A61B 2017/00477* (2013.01); *A61B 2017/00809* (2013.01); *A61B 2017/0609* (2013.01); *A61B 2017/06047* (2013.01); *A61B 2017/2916* (2013.01); *A61B 2017/2936* (2013.01)

(58) Field of Classification Search
    CPC ........... A61B 2017/00367; A61B 2017/00371; A61B 2017/00407; A61B 2017/0046; A61B 2017/00473; A61B 2017/00477; A61B 2017/00809; A61B 2017/06047; A61B 2017/0609; A61B 2017/2916; A61B 2017/2936
    See application file for complete search history.

(56) References Cited

U.S. PATENT DOCUMENTS

| | | |
|---|---|---|
| 1,293,565 A | 2/1919 | Smit |
| 1,449,087 A | 3/1923 | Bugbee |
| 1,876,792 A | 9/1932 | Thompson |
| 2,213,830 A | 9/1940 | Anastasi |
| 2,880,728 A | 4/1959 | Rights |
| 3,090,386 A | 5/1963 | Curtis |
| 3,349,772 A | 10/1967 | Rygg |
| 3,470,875 A | 10/1969 | Johnson |
| 3,807,407 A | 4/1974 | Schweizer |
| 3,842,840 A | 10/1974 | Schweizer |
| 3,901,244 A | 8/1975 | Schweizer |
| 3,946,740 A | 3/1976 | Bassett |
| 4,021,896 A | 5/1977 | Stierlein |
| 4,109,658 A | 8/1978 | Hughes |
| 4,161,951 A | 7/1979 | Scanlan, Jr. |
| 4,164,225 A | 8/1979 | Johnson et al. |
| 4,236,470 A | 12/1980 | Stenson |
| 4,345,601 A | 8/1982 | Fukuda |
| 4,373,530 A | 2/1983 | Kilejian |
| 4,471,781 A | 9/1984 | Di Giovanni et al. |
| 4,491,135 A | 1/1985 | Klein |
| 4,580,567 A | 4/1986 | Schweitzer et al. |
| 4,621,640 A | 11/1986 | Mulhollan et al. |
| 4,635,638 A | 1/1987 | Weintraub et al. |
| 4,890,615 A | 1/1990 | Caspari et al. |
| 4,923,461 A | 5/1990 | Caspari et al. |
| 4,935,027 A | 6/1990 | Yoon |
| 4,957,498 A | 9/1990 | Caspari et al. |
| 5,059,201 A | 10/1991 | Asnis |
| 5,100,421 A | 3/1992 | Christoudias |
| 5,171,257 A | 12/1992 | Ferzli |
| 5,181,919 A | 1/1993 | Bergman et al. |
| 5,207,693 A | 5/1993 | Phillips |
| 5,217,471 A | 6/1993 | Burkhart |
| 5,242,458 A | 9/1993 | Bendel et al. |
| 5,254,126 A | 10/1993 | Filipi et al. |
| 5,261,917 A | 11/1993 | Hasson et al. |
| 5,281,220 A | 1/1994 | Blake, III |
| 5,336,230 A | 8/1994 | Leichtling et al. |
| 5,454,823 A | 10/1995 | Richardson et al. |
| 5,674,229 A | 10/1997 | Tovey et al. |
| 5,674,230 A | 10/1997 | Tovey et al. |
| 5,690,652 A | 11/1997 | Wurster et al. |
| 5,814,054 A | 9/1998 | Kortenbach et al. |
| 5,980,538 A | 11/1999 | Fuchs et al. |
| 6,270,508 B1 | 8/2001 | Klieman et al. |
| 8,177,794 B2 | 5/2012 | Cabrera et al. |
| 8,226,667 B2 | 7/2012 | Viola et al. |
| 8,246,637 B2 | 8/2012 | Viola et al. |
| 8,292,905 B2 | 10/2012 | Taylor et al. |
| 8,292,906 B2 | 10/2012 | Taylor et al. |
| 8,337,515 B2 | 12/2012 | Viola et al. |
| 8,372,090 B2 | 2/2013 | Wingardner et al. |
| 8,454,631 B2 | 6/2013 | Viola et al. |
| 8,460,275 B2 | 6/2013 | Taylor et al. |
| 8,490,713 B2 | 7/2013 | Furnish et al. |
| 8,496,674 B2 | 7/2013 | Cabrera et al. |
| 8,506,581 B2 | 8/2013 | Wingardner, III et al. |
| 8,628,545 B2 | 1/2014 | Cabrera et al. |
| 8,636,752 B2 | 1/2014 | Cabrera et al. |
| 8,747,424 B2 | 6/2014 | Taylor et al. |
| D708,746 S | 7/2014 | Cabrera et al. |
| 8,864,776 B2 | 10/2014 | Bogart et al. |
| 8,968,340 B2 | 3/2015 | Chowaniec et al. |
| 8,968,342 B2 | 3/2015 | Wingardner, III et al. |
| 9,113,860 B2 | 8/2015 | Viola et al. |
| 9,271,723 B2 | 3/2016 | Taylor et al. |
| 9,615,824 B2 | 4/2017 | Furnish et al. |
| 9,675,340 B2 | 6/2017 | Sniffin et al. |
| 10,806,441 B2 | 10/2020 | Malkowski |
| 11,058,413 B2 | 7/2021 | Malkowski et al. |
| 2004/0260314 A1 | 12/2004 | Lizardi |
| 2005/0149066 A1 | 7/2005 | Stafford |
| 2006/0020274 A1 | 1/2006 | Ewers |
| 2009/0221868 A1 | 9/2009 | Evans |
| 2009/0299406 A1 | 12/2009 | Swain |
| 2010/0228270 A1 | 9/2010 | Bogart et al. |
| 2011/0040308 A1 | 2/2011 | Cabrera et al. |
| 2013/0023725 A1 | 1/2013 | Nose |

FOREIGN PATENT DOCUMENTS

| | | |
|---|---|---|
| JP | 2001500765 A | 1/2001 |
| JP | 2010505524 A | 2/2010 |
| JP | 2017213369 A | 12/2017 |
| WO | 0022992 A1 | 4/2000 |
| WO | 0054667 A1 | 9/2000 |
| WO | 2007033314 A2 | 3/2007 |
| WO | 2008045353 A2 | 4/2008 |

OTHER PUBLICATIONS

Partial European Search Report for EP Application No. 18212603.7, dated May 20, 2019.
Extended European Search Report issued in EP Application No. 18212603.7, dated Oct. 26, 2020.
Extended European Search Report dated Sep. 20, 2022 corresponding to counterpart Patent Application EP 22161043.9.
Partial European Search Report dated Jun. 13, 2022 corresponding to counterpart Patent Application EP 22161043.9.

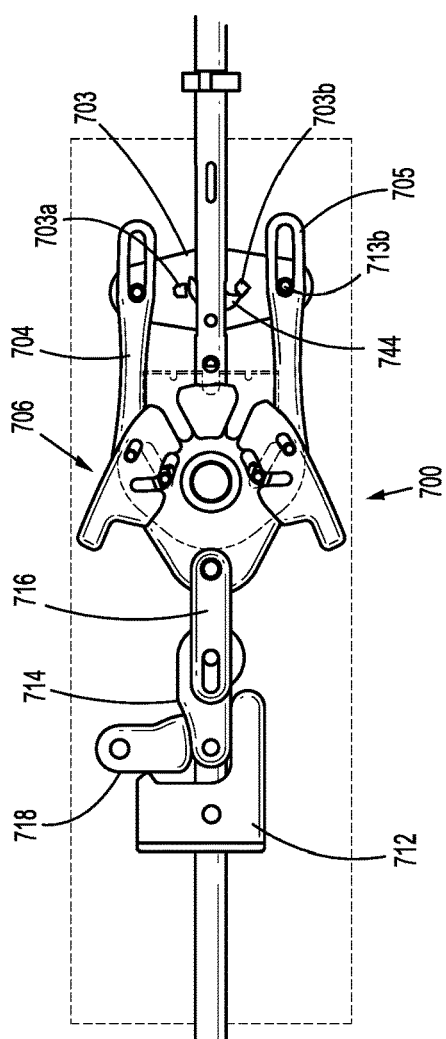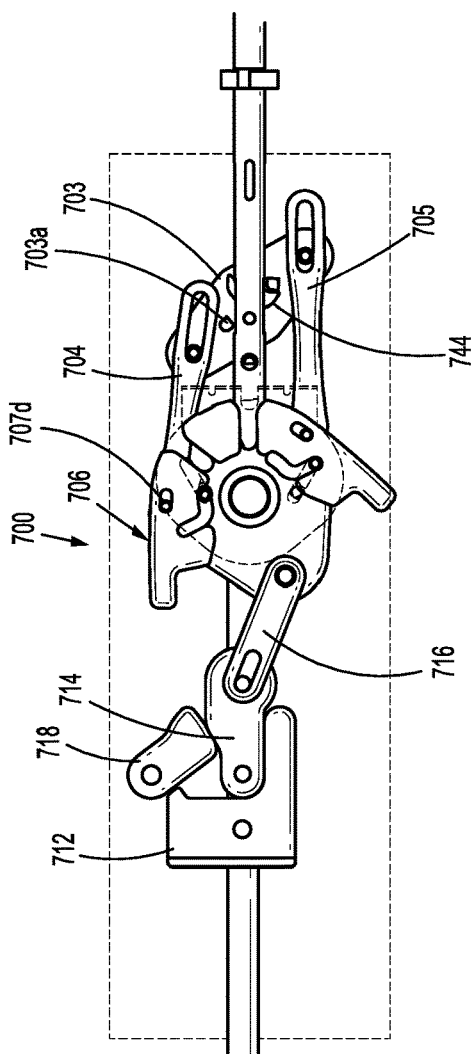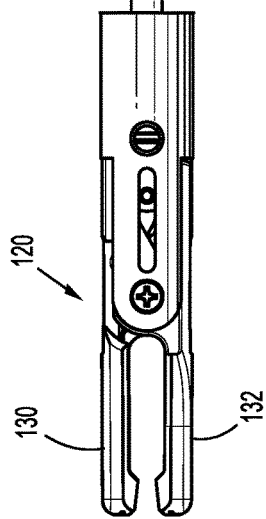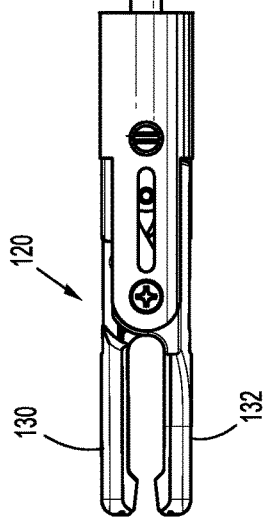

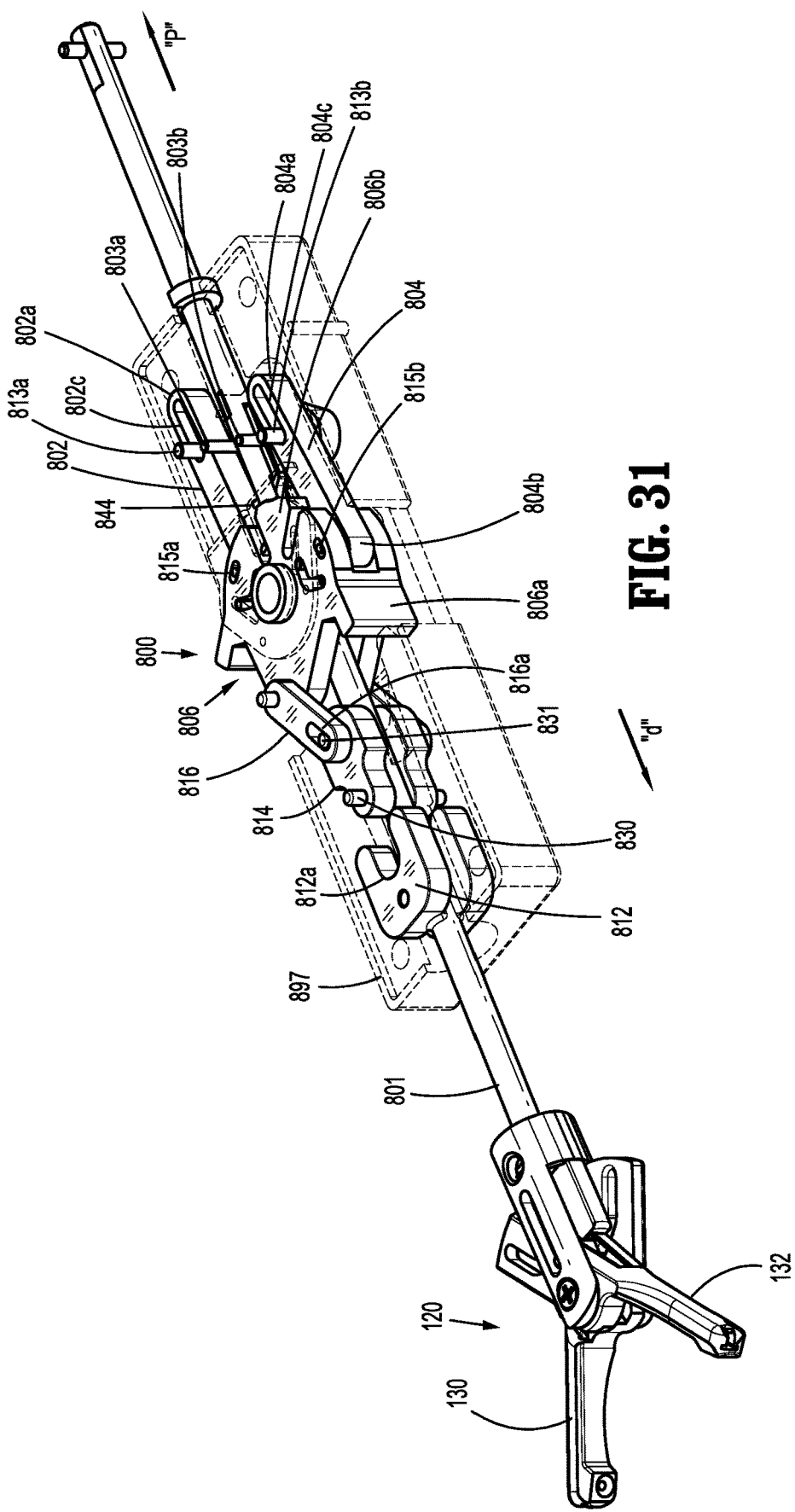

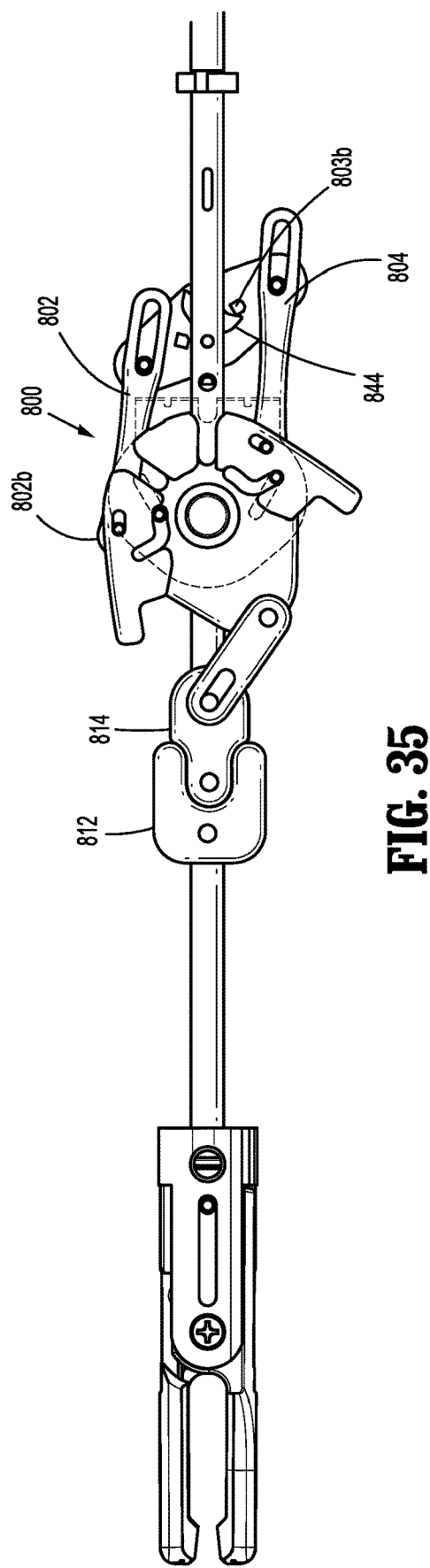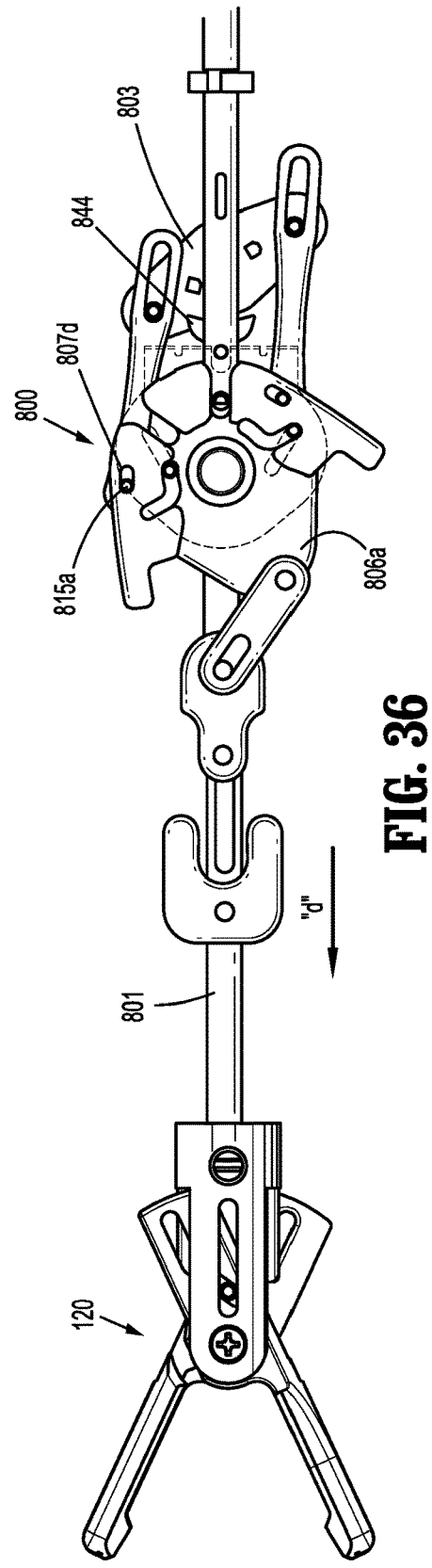

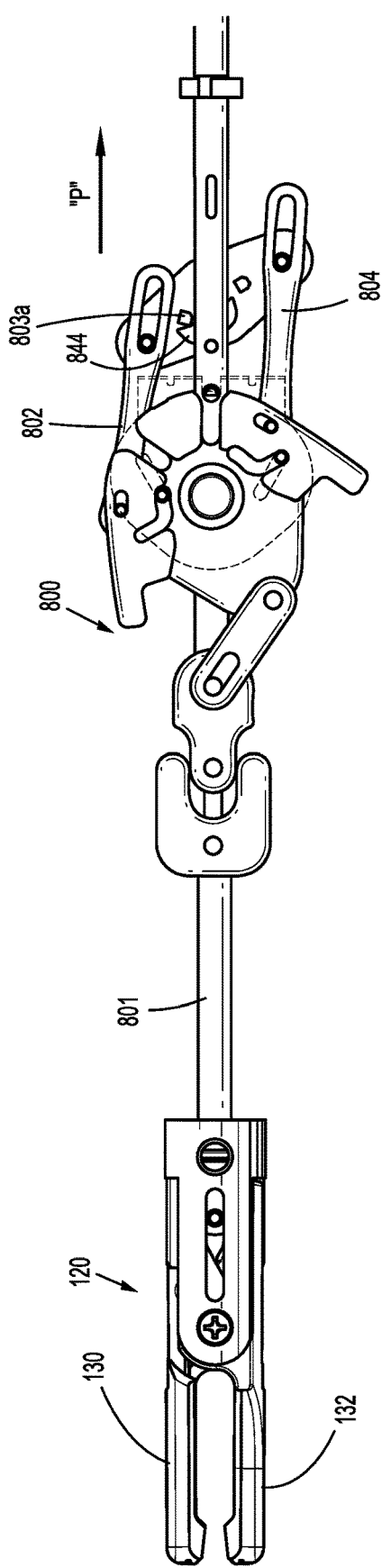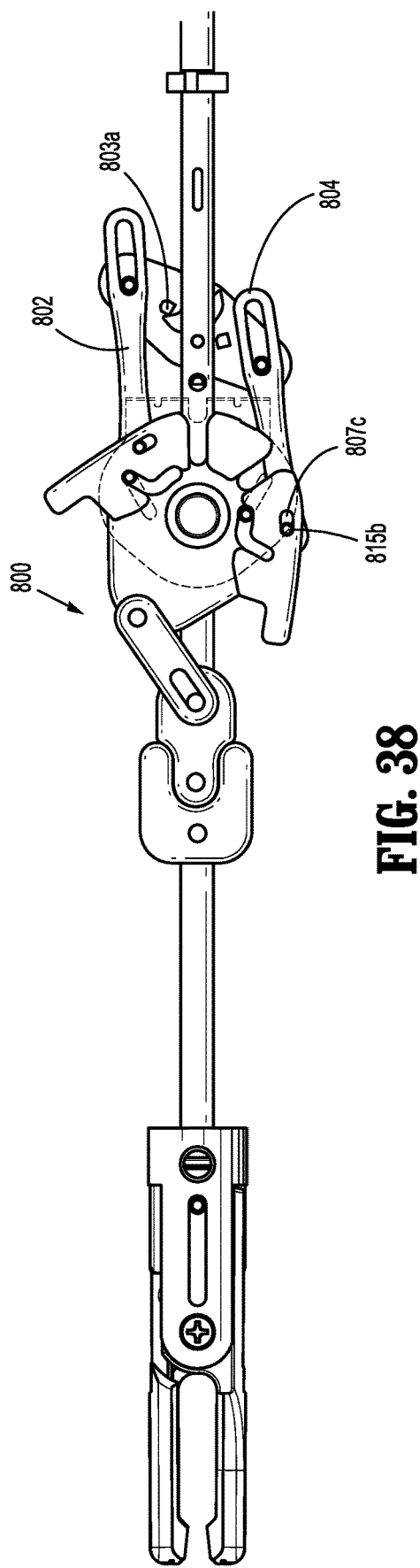

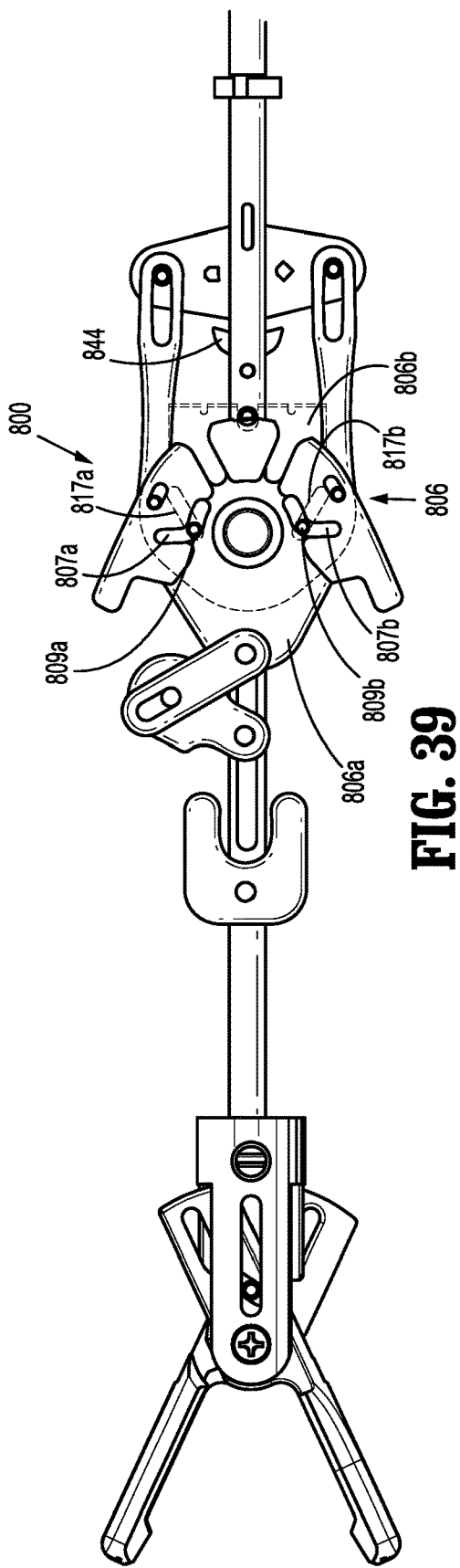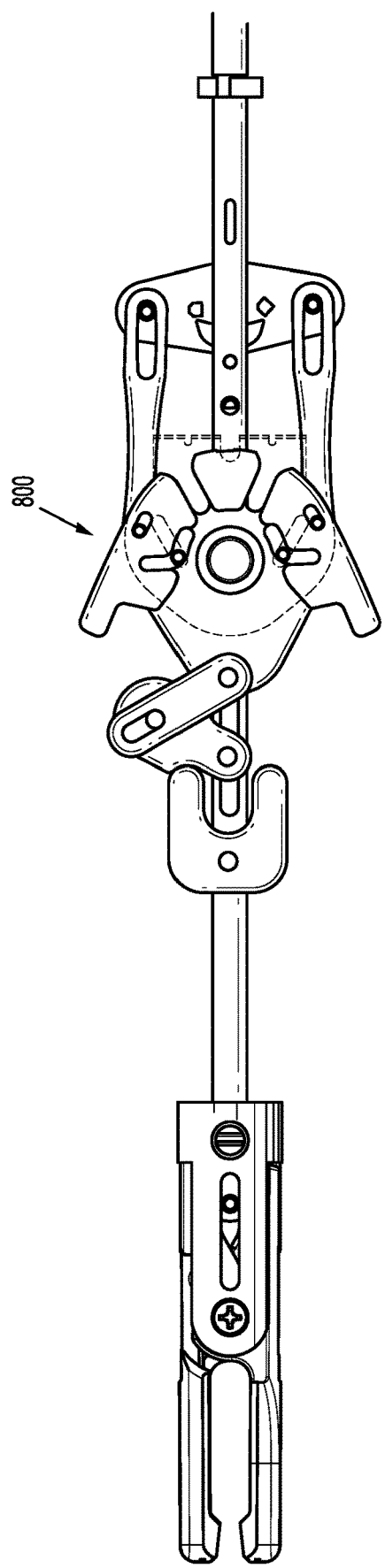

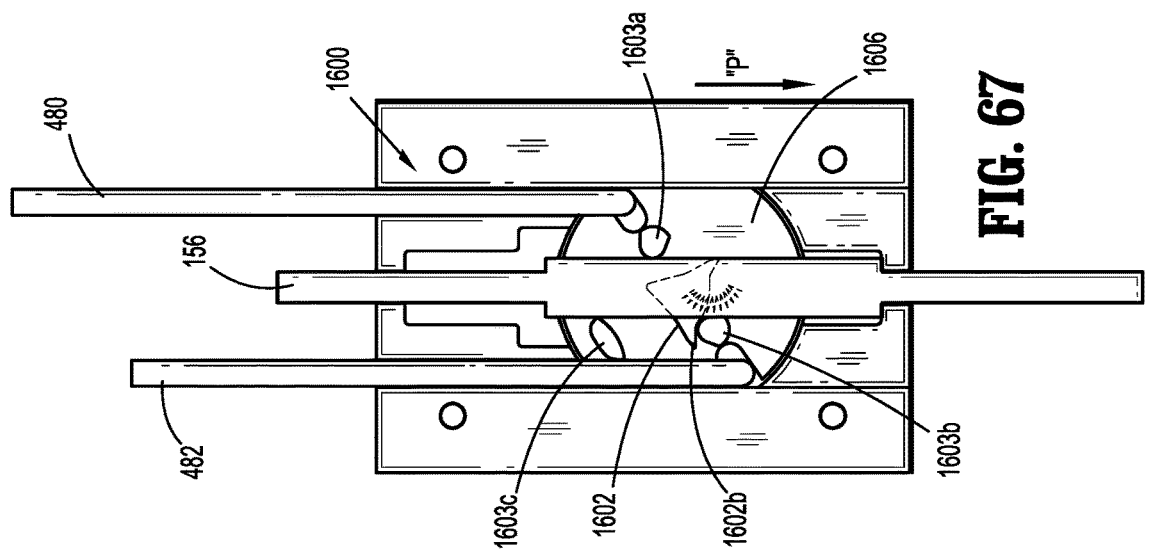
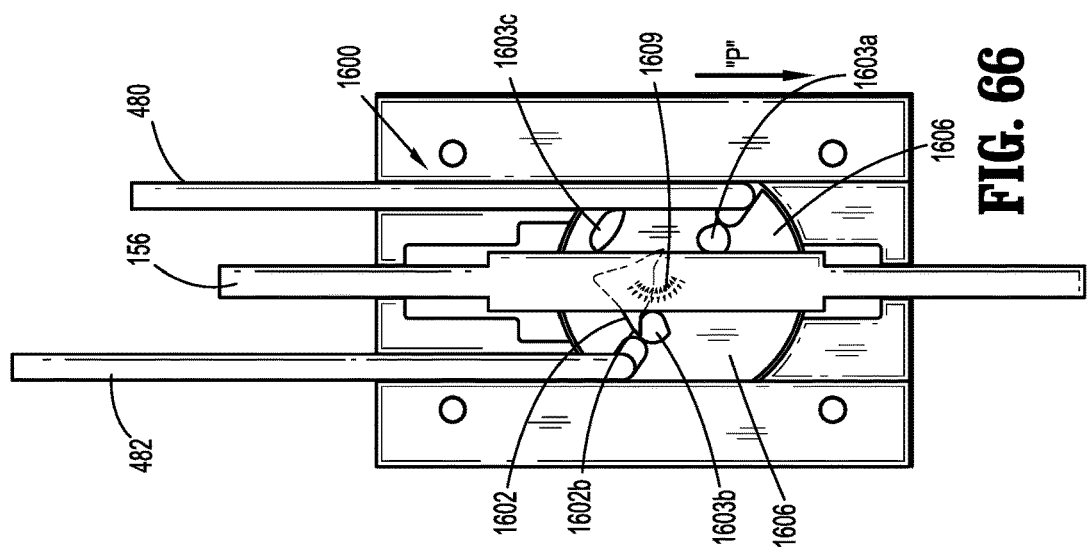
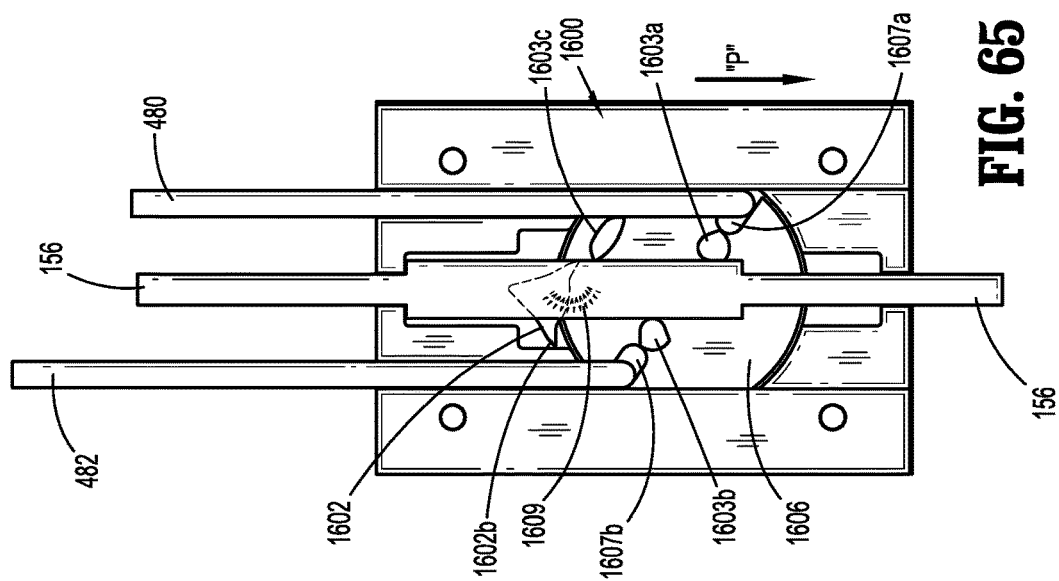

ENDOSCOPIC STITCHING DEVICE

CROSS-REFERENCE TO RELATED APPLICATIONS

This application is a continuation of U.S. patent application Ser. No. 16/142,015, filed on Sep. 26, 2018, which claims the benefit of and priority to U.S. Provisional Patent Application Ser. No. 62/599,060, filed on Dec. 15, 2017, the entire disclosure of each of which is incorporated by reference herein.

BACKGROUND

Technical Field

The present disclosure relates to devices for suturing or stitching and, more particularly, to devices for endoscopic suturing and/or stitching through an access tube or the like.

Background

One of the advances in recent years to reduce the invasiveness of surgical procedures is endoscopic surgery. Generally, endoscopic surgery involves incising through body walls. Typically, trocars are utilized for creating the incisions through which the endoscopic surgery is performed. Trocar tubes or cannula devices are extended into and left in place in the abdominal wall to provide access for endoscopic surgical tools. A camera or endoscope is inserted through a relatively large diameter trocar tube which is generally located at the naval incision, and permits the visual inspection and magnification of the body cavity. The surgeon can then perform diagnostic and therapeutic procedures at the surgical site with the aid of specialized instrumentation, such as, forceps, cutters, applicators, and the like which are designed to fit through additional cannulas.

In many surgical procedures, including those involved in endoscopic surgery, it is often necessary to suture bodily organs or tissue. Suturing may be challenging during endoscopic surgery because of the small openings through which the suturing of bodily organs or tissues must be accomplished. Accordingly, a need exists for simple and effective devices for endoscopic suturing or stitching.

SUMMARY

The present disclosure describes a device for suturing and stitching that demonstrates a practical approach to meeting the performance requirements and overcoming usability challenges associated with endoscopic suturing or stitching. In accordance with an embodiment of the present disclosure, there is provided an endoscopic stitching device including a handle assembly and an elongate shaft assembly.

In accordance with an embodiment of the present disclosure, there is provided an endoscopic stitching device including a handle assembly and an elongate shaft assembly. The handle assembly includes a main rod and a drive conversion assembly. The main rod is configured for axial displacement. The drive conversion assembly includes a cam wheel, a pivot block, first and second links interconnecting the pivot block with the cam wheel, and a pawl. The pawl is operatively coupled to the main rod, wherein the pawl is configured to engage the pivot block to cause rotation of the pivot block which, in turn, causes reciprocating displacement of the first and second links.

The elongate shaft assembly includes first and second blade drive members coupled to the cam wheel and a tool assembly. The tool assembly includes first and second jaws and first and second blades slidably disposed in the respective first and second jaws. The first and second blades are operatively coupled with the respective first and second blade drive members. Axial displacement of the main rod pivots the first and second jaws between open and closed positions and causes reciprocating axial displacement of the first and second blades.

In an embodiment, the pawl may be spring biased toward an initial position.

In another embodiment, the cam wheel may be cammingly coupled to the first and second blade drive members of the elongate shaft assembly.

In yet another embodiment, proximal ends of the respective first and second blade drive members may include respective camming pins, and the cam wheel may define cam slots configured to receive respective camming pins of the first and second blade drive members.

In still another embodiment, the cam slots of the cam wheel may extend transversely outward in a distal direction. Each of the cam slots may define an L-shape.

In still another embodiment, the first and second links may be cammingly coupled with the cam wheel.

In still another embodiment, each link of the first and second links may define a slot extending transversely with respect to the main rod.

In still yet another embodiment, the pawl may be configured to engage inner surfaces of the respective first and second links during axial displacement of the main rod to guide rotation of the pawl.

In accordance with another embodiment of the present disclosure, there is provided an endoscopic stitching device including a handle assembly and an elongate shaft assembly. The handle assembly includes a main rod configured for axial displacement and a drive conversion assembly. The drive conversion assembly includes a cam wheel, a pivot block, first and second links interconnecting the pivot block with the cam wheel, a pawl, third and fourth links operatively coupled with the cam wheel, and a pusher. The pawl is operatively coupled to the main rod. The pawl is configured to engage the pivot block to rotate the pivot block which, in turn, causes reciprocating displacement of the first and second links. The pusher is operatively coupled to the main rod. The pusher is configured to engage the third link to exert force on the cam wheel.

The elongate shaft assembly includes first and second blade drive members and a tool assembly. The tool assembly includes first and second jaws operatively coupled with the main rod of the handle assembly and first and second blades slidably disposed in the respective first and second jaws. The first and second blades are operatively coupled with the first and second blade drive members, respectively. Axial displacement of the main rod transitions the first and second jaws between open and closed positions and causes reciprocating axial displacement of the first and second blades.

In another embodiment, the pusher may include a cutout portion configured to receive the third link such that the third link is aligned with the main rod.

In still another embodiment, the cam wheel may include a base portion and a coupling portion cammingly coupled with the base portion, wherein the first and second blade drive members may be cammingly coupled with the base portion.

In still another embodiment, the first and second links may be cammingly coupled to the base portion of the cam wheel.

In still another embodiment, the coupling portion of the cam wheel may include a pair of opposing slots. The pair of opposing slots may extend distally inward.

In still another embodiment, the base portion of the cam wheel may define a pair of opposing slots extending transversely outward with respect to the main rod.

In still another embodiment, the drive conversion assembly may further include a fifth link pivotally supported such that when the main rod is advanced proximally, the pusher may push the fifth link to position the third and fourth links in alignment with the main rod.

In yet another embodiment, the pusher may define a cutout having an arcuate portion configured to receive the third link therein.

In still yet another embodiment, the cam wheel may be transitionable between a proximal position in which the first and second links are movable to effect axial displacement thereof and a distal position in which both of the first and second blades are in distal positions to receive a needle.

In still yet another embodiment, the pusher may define a U-shaped cutout.

In still yet another embodiment, the third link may include a camming pin that may ride along a camming slot defined in the main rod.

In still yet another embodiment, the cam wheel of the drive conversion assembly may include a lock out pin and the main rod may include an engaging pin configured to inhibit axial movement of the main rod when the lock out pin and the engaging pin engage each other in alignment.

In accordance with another embodiment of the present disclosure, there is provided a handle assembly for use with an endoscopic stitching device. The handle assembly includes a main rod and a cam wheel assembly. The main rod includes a worm gear portion. The main rod is operatively coupled to jaws of a tool assembly of the endoscopic stitching device. The cam wheel assembly includes slots configured to cammingly engage blade drive members coupled to needle engaging blades of the tool assembly. The cam wheel assembly includes first and second gears configured to engage the worm gear portion of the main rod such that rotation or translation of worm gear portion causes rotation of the first and second gears in opposite directions, wherein the first and second gears are operatively coupled with the blade drive members, whereby axial displacement of the main rod causes reciprocating axial displacement of the blade drive members and transitioning of the jaws between open and closed positions.

In an embodiment, the cam wheel assembly may further include first and second links pivotably connected with the respective blade drive members, and first and second rotatable arms may be pivotably coupled with the respective first and second links.

In another embodiment, the first and second gears may include respective inner surfaces configured to engage the respective first and second rotatable arms.

In yet another embodiment, the inner surfaces of the first and second gears may include teeth configured to limit rotation of the respective first and second gears to a single direction.

In accordance with another embodiment of the present disclosure, there is provided an endoscopic stitching device including an elongate shaft assembly and a handle assembly. The elongate shaft assembly includes a tool assembly and first and second blade drive members. The tool assembly includes first and second jaws and first and second blades slidably disposed in the respective first and second jaws. The first and second blades are operatively coupled with the first and second blade drive members, respectively. The handle assembly includes a main rod configured for axial displacement and a drive conversion assembly operatively coupled with the first and second blade drive members. The drive conversion assembly includes a cam wheel and a pawl operatively coupled to the main rod. The cam wheel includes first, second, and third pins. The pawl is configured to engage the first pin to cause rotation of the cam wheel in a first direction which, in turn, causes reciprocating displacement of the first and second blade drive members, and the second pin to cause rotation of the cam wheel in a second direction, which, in turn, causes reciprocating displacement of the first and second blade drive members in opposite directions. The pawl is also configured to engage the third pin to cause the pawl to extend transversely outward of the main rod away from the third pin. Axial displacement of the main rod pivots the first and second jaws between open and closed positions and causes reciprocating axial displacement of the first and second blades.

In an embodiment, the first and second pins may diametrically oppose each other.

In another embodiment, the first and second pins may be disposed adjacent the first and second blade drive members, respectively.

In yet another embodiment, the pawl may be coupled to a biasing member.

In still yet another embodiment, displacement of the main rod in a proximal direction may cause the pawl to engage the first or second pin.

In still yet another embodiment, displacement of the main rod in a distal direction may cause the pawl to engage the third pin.

DETAILED DESCRIPTION OF THE DRAWINGS

The foregoing objects, features and advantages of the disclosure will become more apparent from a reading of the following description in connection with the accompanying drawings, in which:

FIGS. 29 and 30 are partial top views of the stitching device of FIG. 25, illustrating rotation of a pivot block;

FIG. 31 is a partial, perspective view of a stitching device including a drive conversion assembly in accordance with another embodiment of the present disclosure, illustrating the drive conversion assembly in an operational mode;

FIGS. 33-42 are partial, top views of the stitching device of FIG. 31, illustrating operation of the drive conversion assembly;

FIGS. 65-69 are partial, top views of a drive conversion assembly in accordance with another embodiment of the present disclosure, illustrating operation of the drive conversion assembly;

DETAILED DESCRIPTION

Figure 1:
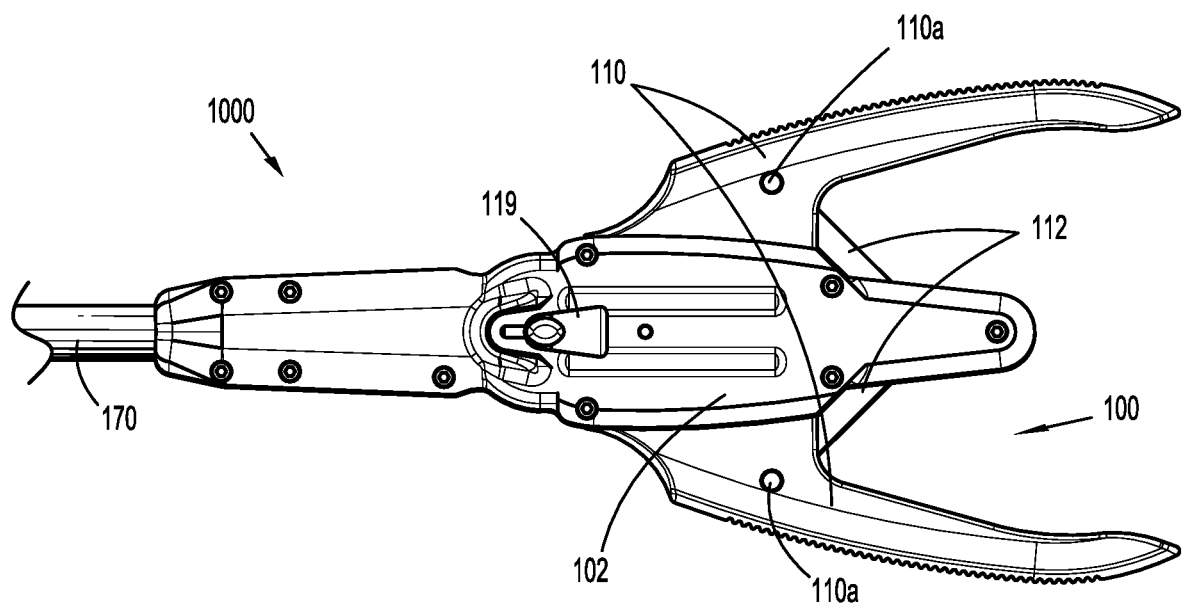
FIG. 1 is a partial top view of a stitching device in accordance with an embodiment of the present disclosure.

Embodiments of the present disclosure will now be described in detail with reference to the drawings, in which like reference numerals designate identical or corresponding elements in each of the several views. As used herein, the term "distal," as is conventional, will refer to that portion of the instrument, apparatus, device or component thereof which is farther from the user while, the term "proximal," will refer to that portion of the instrument, apparatus, device or component thereof which is closer to the user. In the following description, well-known functions or constructions are not described in detail to avoid obscuring the present disclosure in unnecessary detail.

Figure 2:
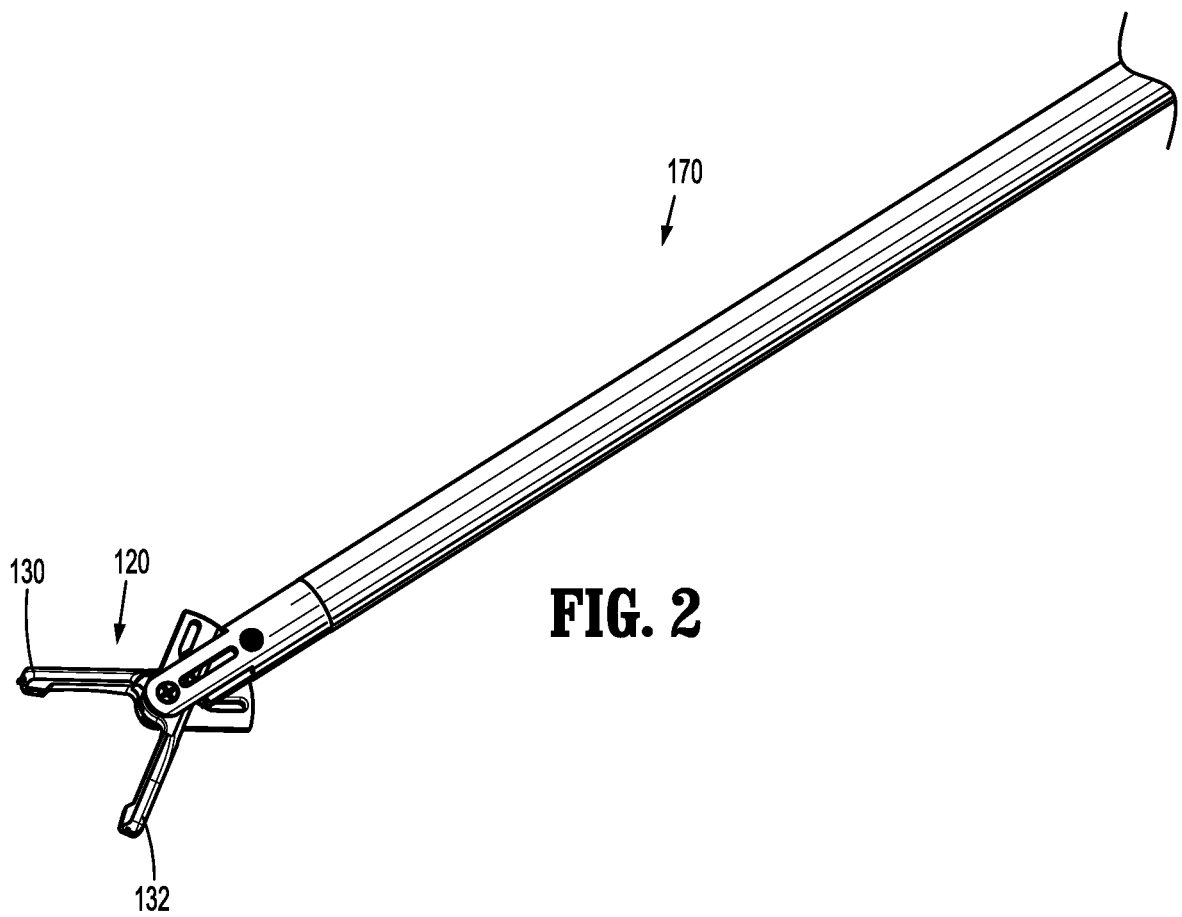
FIG. 2 is a perspective view of an elongate shaft assembly of the stitching device of FIG. 1.

With reference to FIGS. 1 and 2, an embodiment of the present disclosure is generally shown as a stitching device 1000. Stitching device 1000 is adapted to be particularly useful in endoscopic or laparoscopic procedures, wherein an endoscopic portion of stitching device 1000 such as, e.g., a tool assembly 120, is insertable into an operative site, via a cannula assembly or the like (not shown). Stitching device 1000 includes a handle assembly 100 and an elongate shaft assembly 170 extending distally from handle assembly 100. Handle assembly 100 and elongate shaft assembly 170 may be detachably coupled. The detachability of elongate shaft assembly 170 with handle assembly 100 enhances reusability of stitching device 1000 by facilitating, e.g., sterilization of stitching device 1000.

Handle assembly 100 includes a drive conversion assembly 400 (FIG. 6) configured to convert axial displacement of a main rod 156 (FIG. 6) into both functions of opening and closing jaws 130, 132 and providing reciprocating axial displacement of blades 150, 152 (FIG. 5) to enable swapping of needle 104 between jaws 130, 132, thereby eliminating the need for a separate toggle mechanism to manually move blades 150, 152 (FIG. 5) in opposite directions, as will be described hereinbelow. Eliminating a separate toggle mechanism enhances the operability of stitching device 1000 and reduces the hand fatigue experienced by the clinician.

Figure 3:
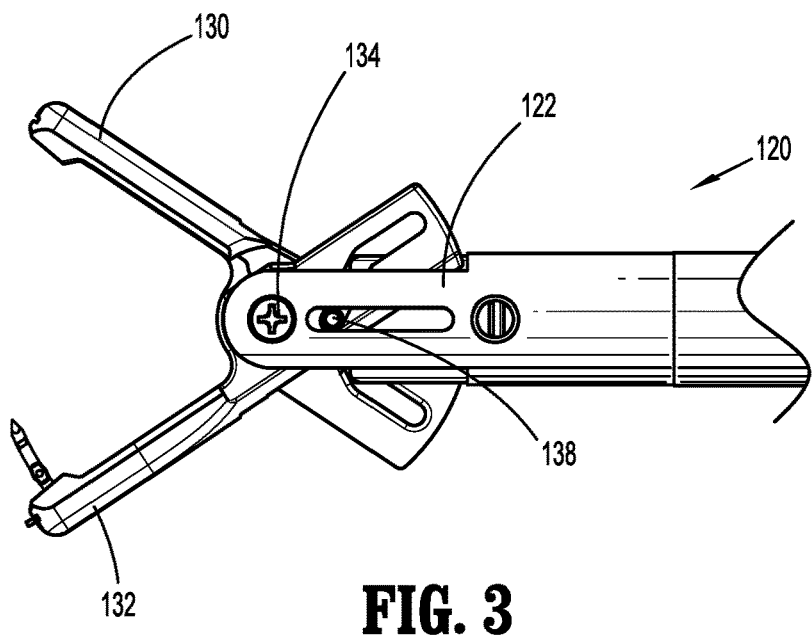
FIG. 3 is a top view of a tool assembly of the elongate shaft assembly of FIG. 2.
Figure 4:
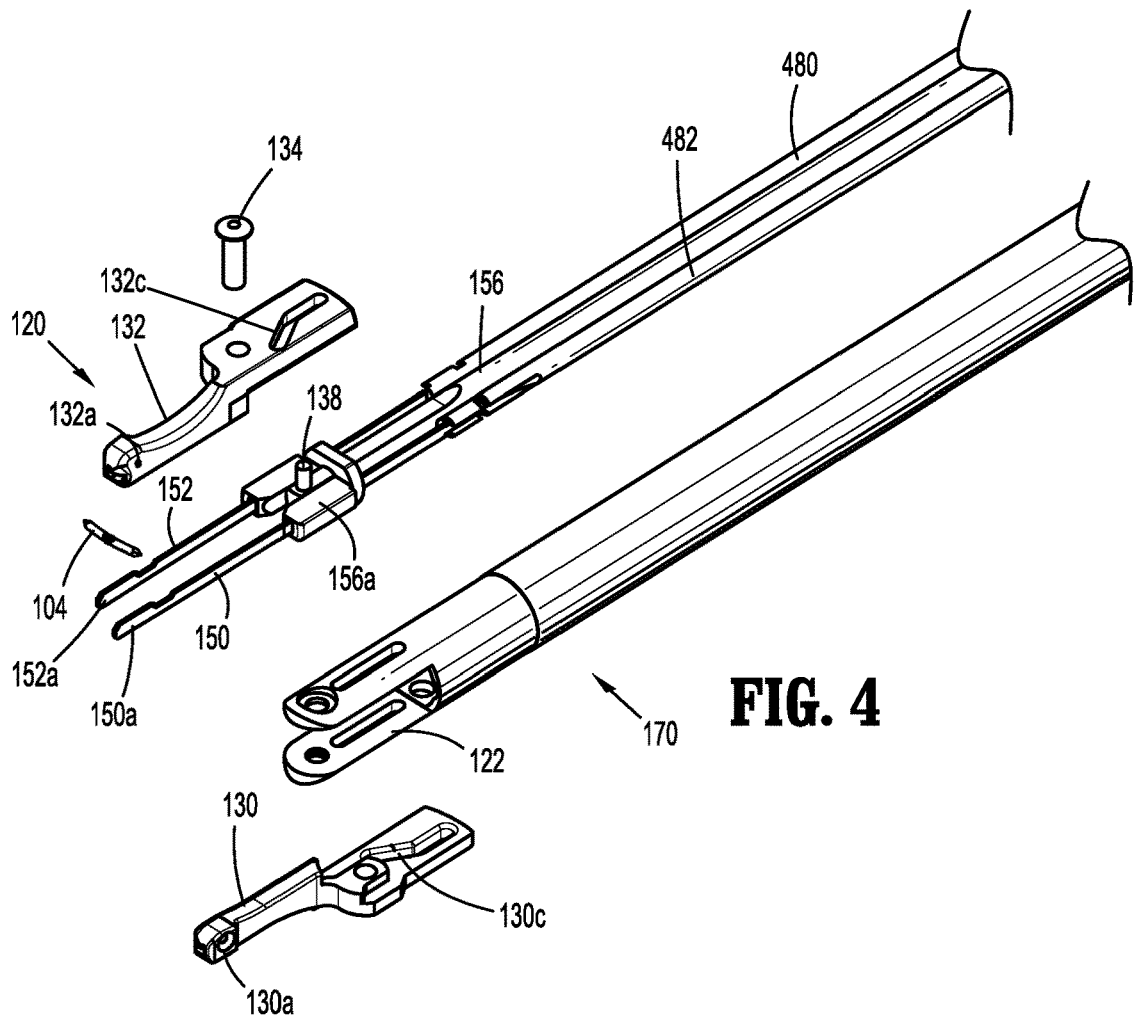
FIG. 4 is a partial, exploded perspective view of the elongate shaft assembly of FIG. 2 with parts separated.
Figure 5:
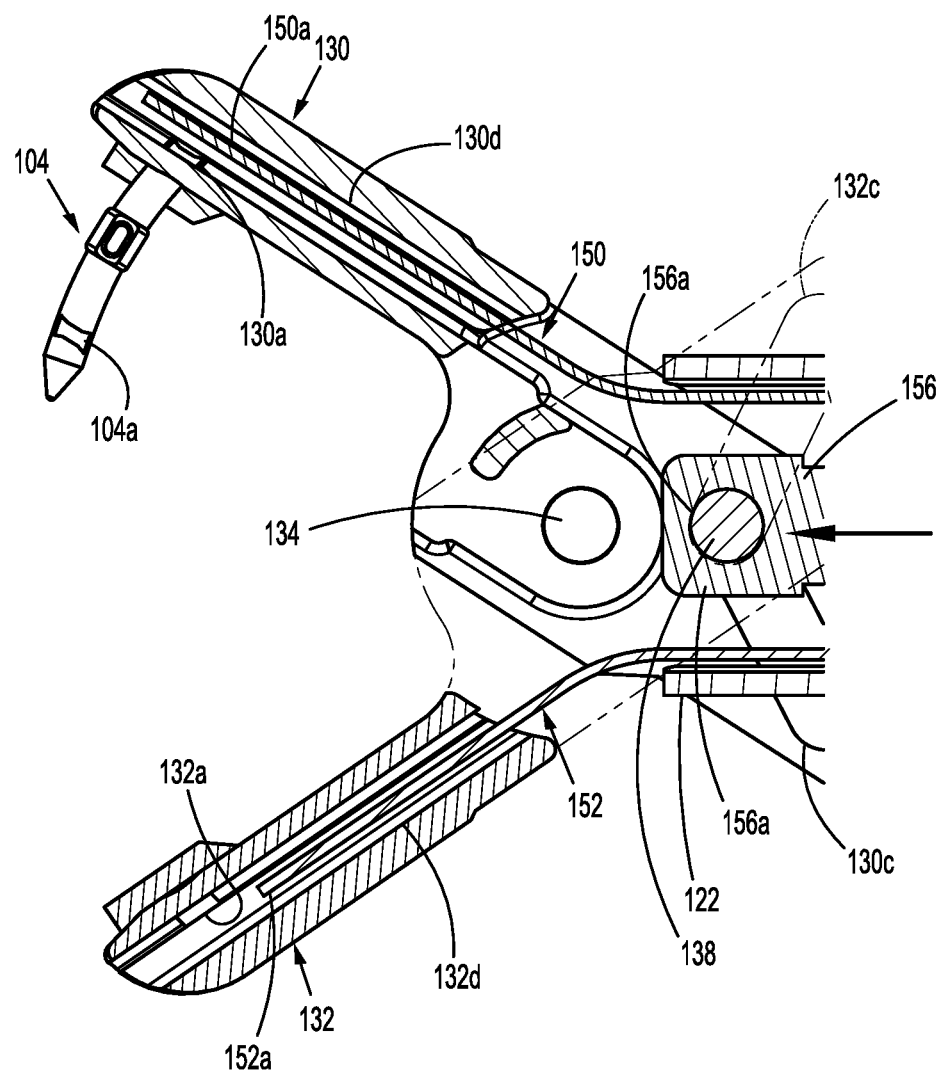
FIG. 5 is a partial cross-sectional view of the tool assembly of FIG. 3.

With reference to FIGS. 3-5, elongate shaft assembly 170 includes tool assembly 120. Tool assembly 120 includes a support member 122 and jaws 130, 132 pivotably mounted on support member 122 by means of a jaw pivot pin 134. To move jaws 130, 132 between an open position and a closed position, main rod 156 has a camming pin 138 mounted at a distal end 156a thereof. Camming pin 138 rides in angled camming slots 130c, 132c defined in respective jaws 130, 132 such that axial or longitudinal movement of main rod 156 causes jaws 130, 132 to be cammed between the open and closed positions.

With particular reference to FIG. 5, tool assembly 120 further includes a pair of needle engaging members or blades 150, 152 which are slidably supported within support member 122. Each blade 150, 152 includes a distal end 150a, 152a slidably extending into blade receiving channels 130d, 132d of respective jaws 130, 132. Channels 130d, 132d are dimensioned to at least partially intersect needle recesses 130a, 132a. Thus, by advancing blade 150 or 152 within respective channel 130d, 132d, distal end 150a, 152a of advancing blade 150, 152 engages or "locks in" a groove 104a formed in needle 104 when at least a portion of needle 104 is received within respective recesses 130a, 132a. A suture (not shown) may be secured to needle 104. The suture may include a plurality of barbs oriented to resist movement in a direction opposite to the direction of travel.

Figure 6:
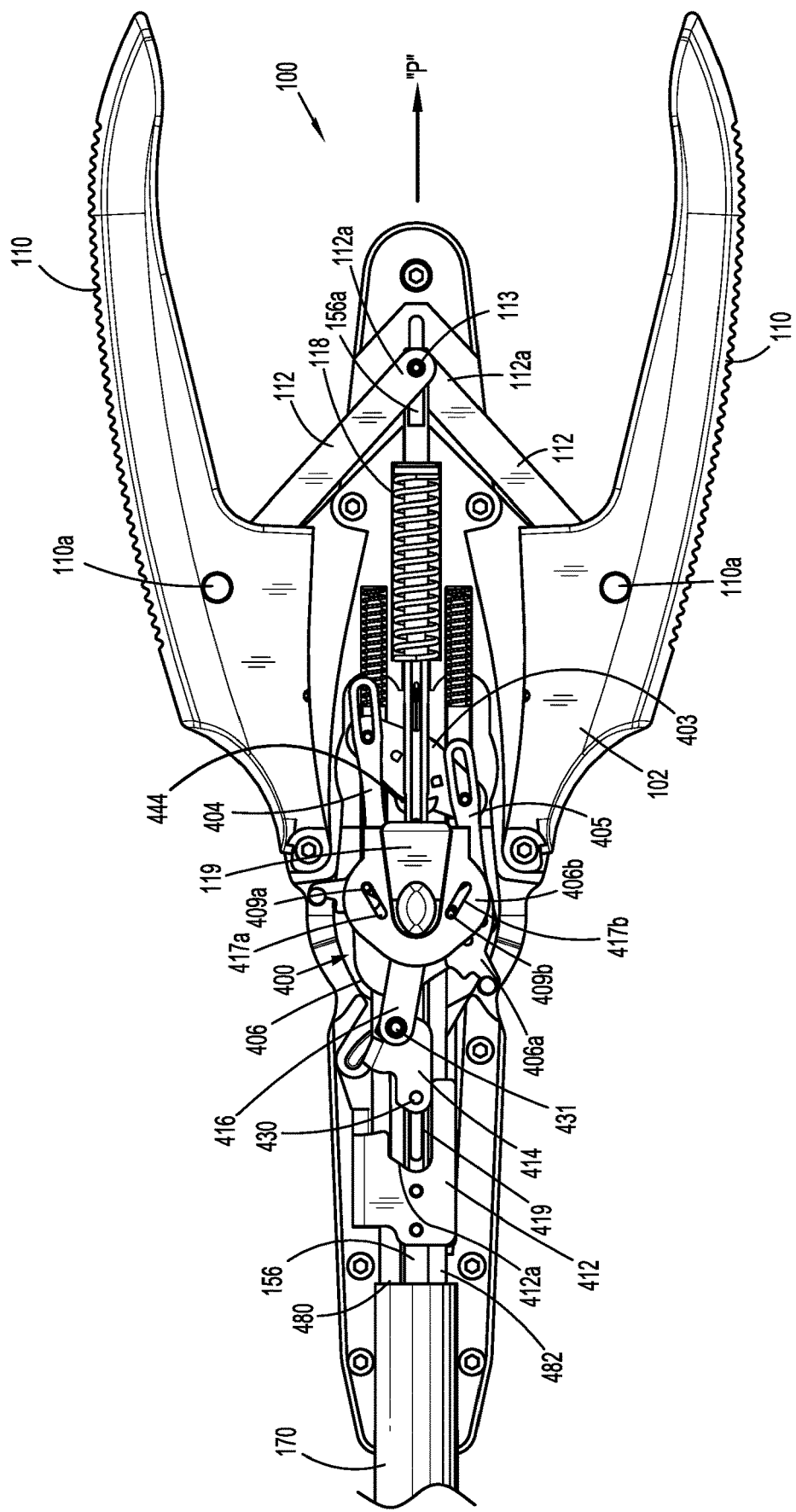
FIG. 6 is a top view of a handle assembly of FIG. 1 with a portion of a housing removed, illustrating a drive conversion assembly.

With reference now to FIG. 6, handle assembly 100 includes a pair of handles 110 pivotably secured to housing 102. Handles 110 are operatively coupled by link members 112. Each link member 112 has a first end (not shown) pivotably connected to respective handles 110 at a pivot point 110a and a second end 112a pivotably connected to a proximal portion 156a of main rod 156 by a pin 113. Under such a configuration, when handles 110 are squeezed, link members 112 advance main rod 156 proximally in the direction of an arrow "p". Main rod 156 may be provided with, e.g., biasing members, in the form of a return spring 118, to bias main rod 156 toward the initial position. Main rod 156 is operatively coupled to jaws 130, 132 (FIG. 2) of tool assembly 120, such that axial displacement of main rod 156 transitions jaws 130, 132 between the open and closed positions.

With continued reference to FIG. 6, handle assembly 100 further includes first and second blade drive members 480, 482 extending through elongate shaft assembly 170. First and second blade drive members 480, 482 are coupled with respective blades 150, 152 (FIG. 5), such that reciprocating axial displacement of first and second blade drive members 480, 482 provides reciprocating axial displacement of blades 150, 152, enabling swapping of needle 104 between jaws 130, 132. Reference may be made to U.S. Pat. No. 8,628, 545, entitled "Endoscopic Stitching Devices," the entire content of which is incorporated herein by reference, for a detailed discussion of the construction and operation of a handle assembly and a tool assembly.

With reference to FIGS. 6-9, handle assembly 100 includes drive conversion assembly 400 operatively coupled to main rod 156. Drive conversion assembly 400 is configured to convert axial displacement of main rod 156 into two reciprocating motions of blades 150, 152 (FIG. 5) of tool assembly 120. In this manner, axial displacement of main rod 156 effects both functions of opening and closing jaws 130, 132 and providing reciprocating axial displacement of blades 150, 152, thereby eliminating the need for a separate toggle mechanism to move blades 150, 152 (FIG. 5) in opposite directions.

With particular reference to FIG. 6, drive conversion assembly 400 includes a pusher 412 and links 414, 416. Pusher 412 is coupled to main rod 156 for concomitant movement therewith. Pusher 412 defines a cutout 412a having a shape complementary to a shape of a portion of link 414. In addition, a portion of main rod 156, in registration with cutout 412a of pusher 412, defines a slot 419. Link 414 includes a pin 430 slidably engaging slot 419 of main rod 156. Link 416 is pivotably coupled with link 414 by a pin 431. With brief reference to FIG. 8, link 416 includes a proximal portion 416a defining a bore 416b dimensioned to rotatably receive a protrusion 417 of a base portion 406a of a cam wheel 406.

Figure 7:
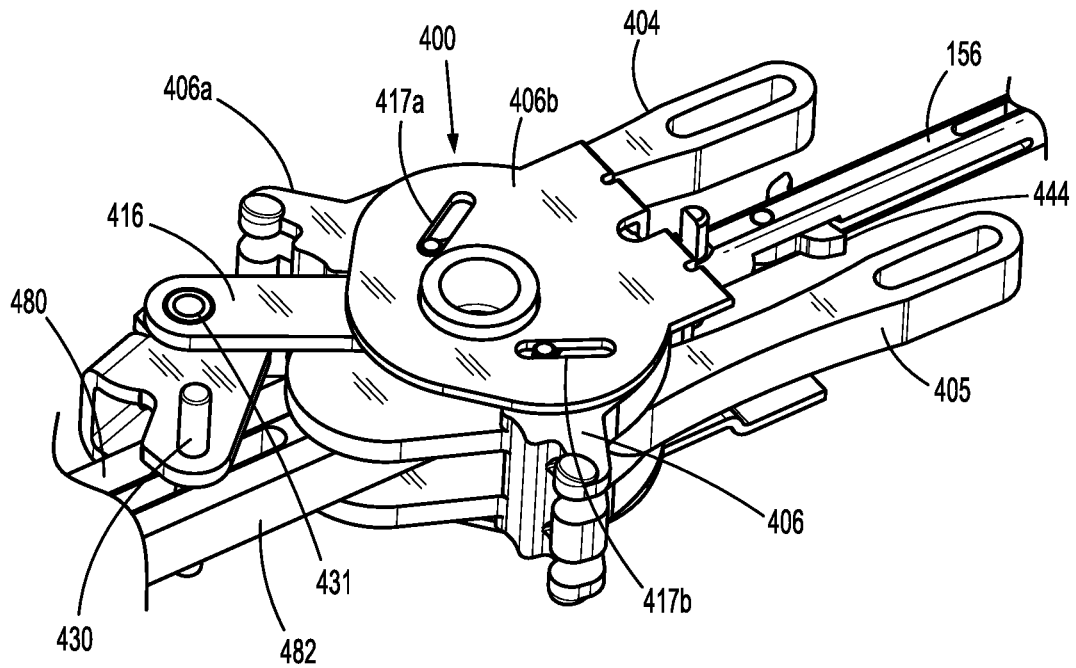
FIG. 7 is a perspective view of the drive conversion assembly of FIG. 6 with a pivot block removed.
Figure 8:
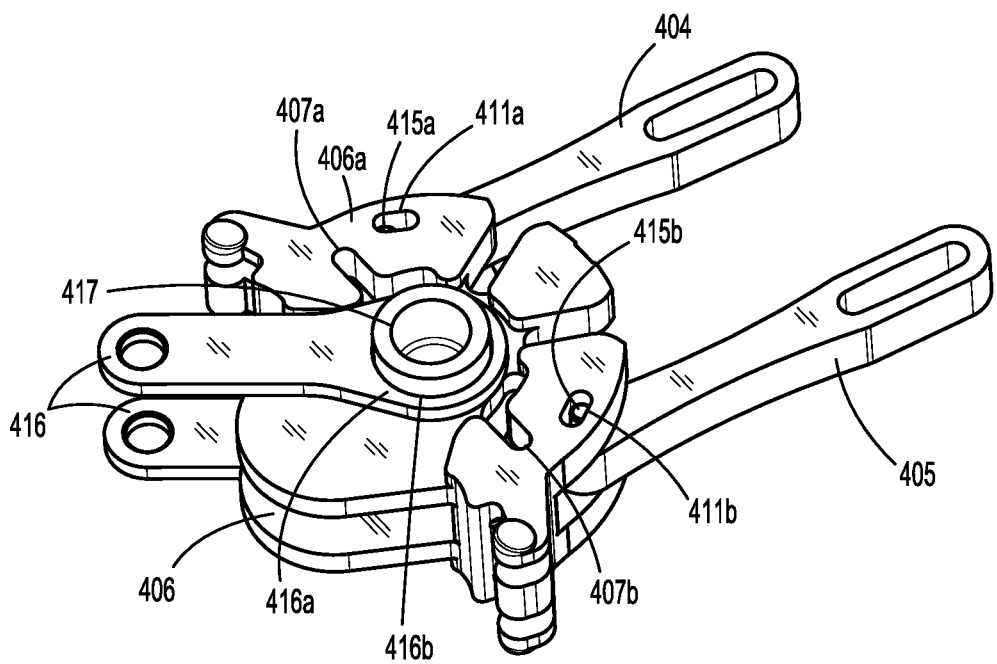
FIG. 8 is a perspective view of the drive conversion assembly of FIG. 7 with a coupling portion of a cam wheel removed.

With reference now to FIGS. 7 and 8, drive conversion assembly 400 further includes cam wheel 406 including a base portion 406a and a coupling portion 406b. Base portion 406a defines camming slots 407a, 407b. Each camming slot 407a, 407b may define an L-shape extending transversely outward. Camming slots 407a, 407b are configured to receive camming pins 409a, 409b (FIG. 6) coupled with respective first and second blade drive members 480, 482 (FIG. 6). Camming pins 409a, 409b extend through respective camming slots 407a, 407b of base portion 406a and further slidably engage respective slots 417a, 417b defined in coupling portion 406b of cam wheel 406. In particular, slots 417a, 417b of coupling portion 406b of cam wheel 406 may be defined on opposing lateral sides of coupling portion 406b and may extend distally inward. Coupling portion 406b may be supported in housing 102 (FIG. 6) by support rods 455 (FIG. 9), which may include biasing members 455a.

Figure 9:
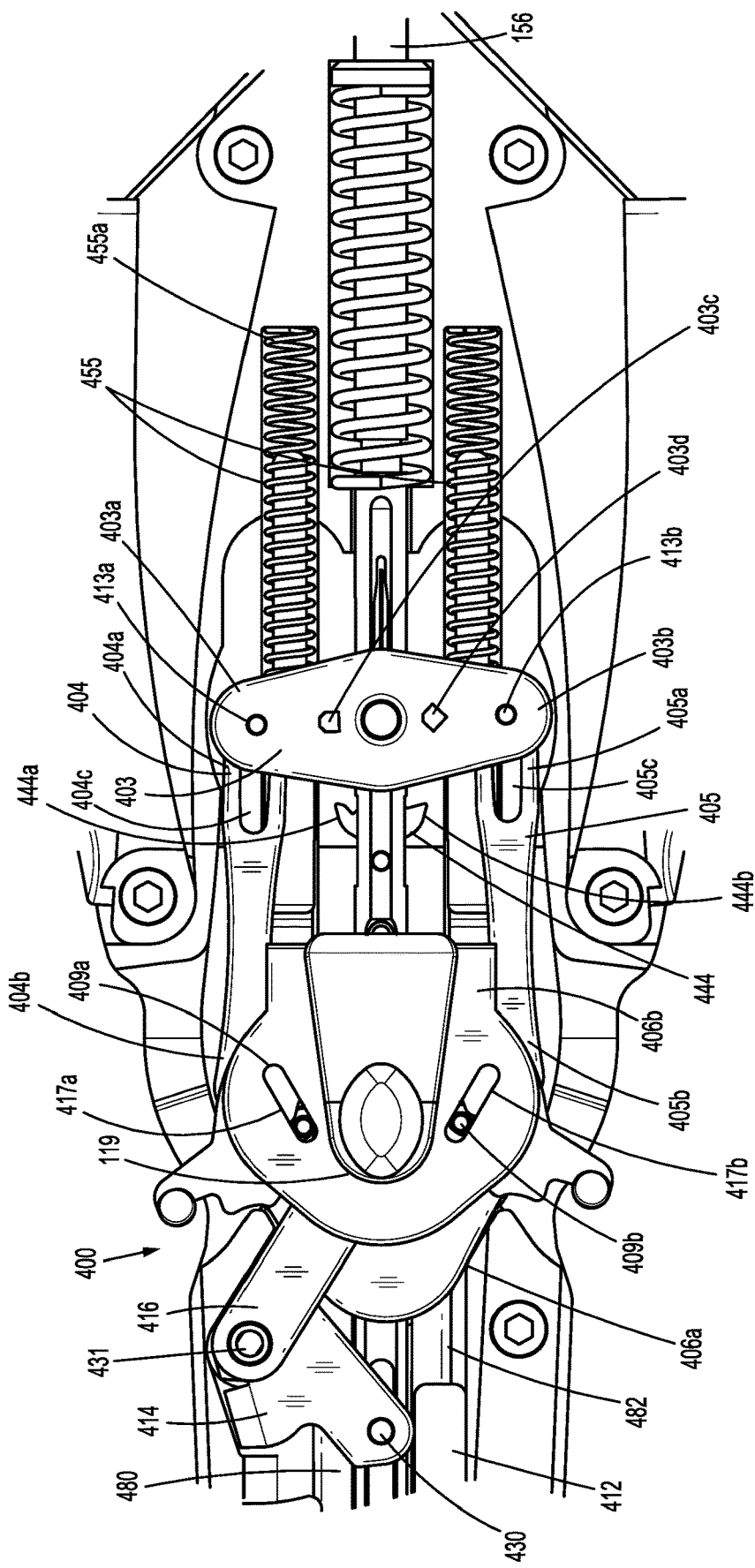
FIG. 9 is a partially enlarged view of the handle assembly of FIG. 6.
Figure 10:
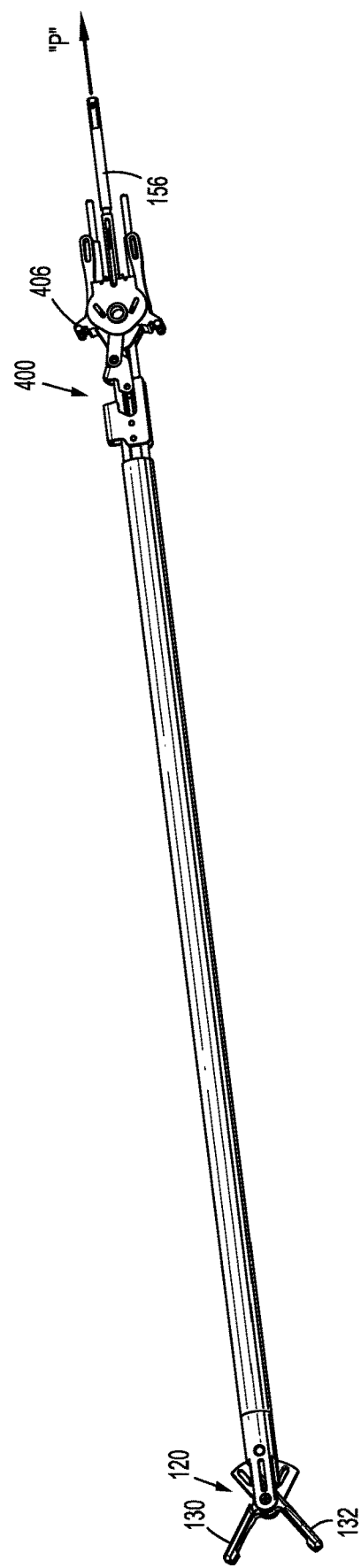
FIG. 10 is a partial perspective view of the stitching device of FIG. 1, illustrating the drive conversion assembly.
Figures 11, 11A:
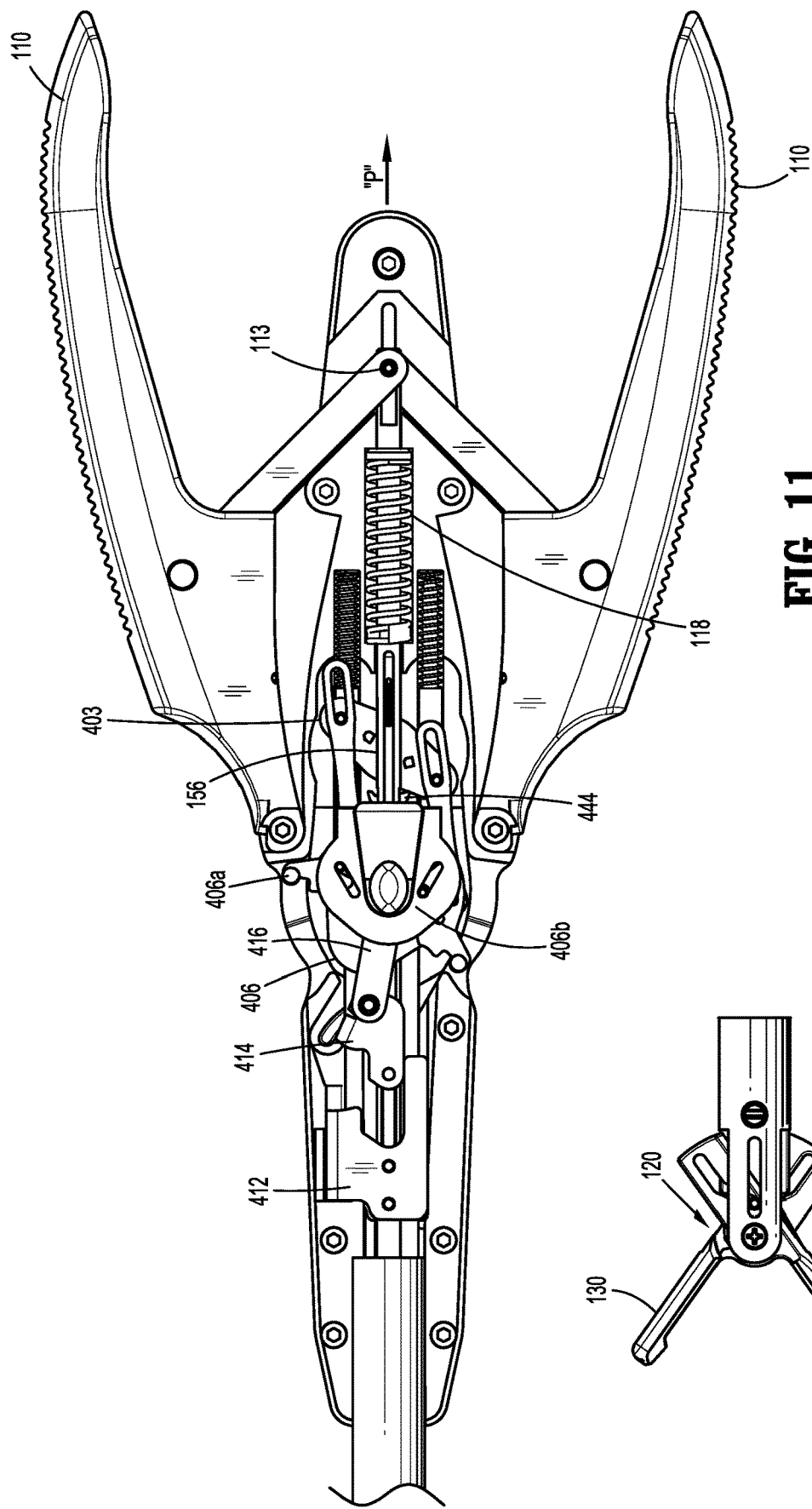
FIGS. 11-14A are partial top views of the stitching device of FIG. 1, illustrating operation thereof.

With reference to FIG. 9, drive conversion assembly 400 further includes links 404, 405 and a pivot block 403 rotatable relative to main rod 156. Each link 404, 405 includes a respective proximal portion 404a, 405a and a respective distal portion 404b, 405b. Proximal portions 404a, 405a of links 404, 405 define respective slots 404c, 405c. Each slot 404c, 405c of links 404, 405 is configured to slidably receive a pin 413a, 413b secured to one of laterally opposing sides 403a, 403b of pivot block 403. Distal portions 404b, 405b of links 404, 405 include respective pins 415a, 415b (FIG. 8). Pin 415a is configured to slidably engage camming slot 411a (FIG. 8) defined in base portion 406a of cam wheel 406, and pin 415b is configured to slidably engage camming slot 411b of base portion 406a.

With continued reference to FIG. 9, drive conversion assembly 400 further includes a pawl 444 biased toward a neutral position in which opposing sides 444a, 444b of pawl 444 extend transversely outward from main rod 156 toward respective links 404, 405. Pawl 444 is configured to engage one of pins 403c, 403d of pivot block 403 depending on the orientation of pivot block 403, when main rod 156 is advanced proximally, in order to rotate pivot block 403, thereby providing reciprocating axial displacement of links 404, 405 in opposite directions. Reciprocating axial displacement of links 404, 405 causes rotation of base portion 406a of cam wheel 406, which, in turn, causes reciprocating axial displacement of first and second blade drive members 480, 482 coupled to respective blades 150, 152 (FIG. 5) of tool assembly 120.

Figure 12:
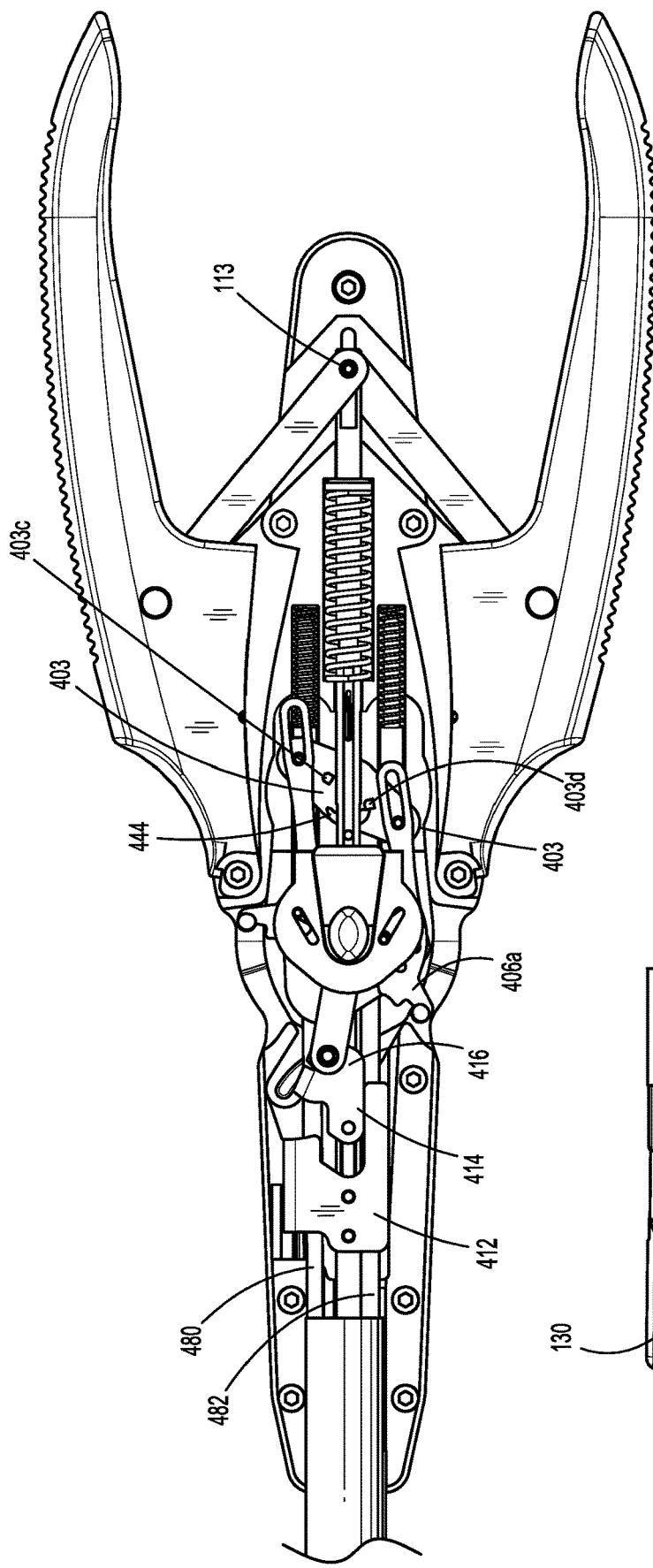
Figure 13:
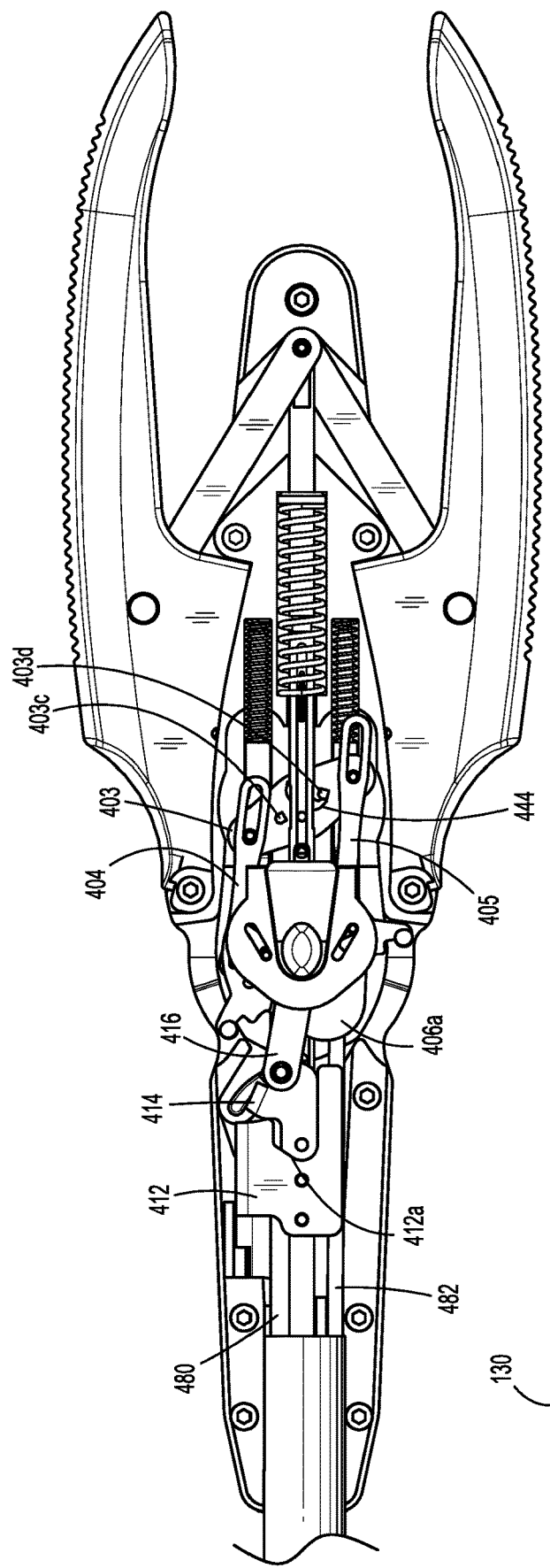
Figure 13A:
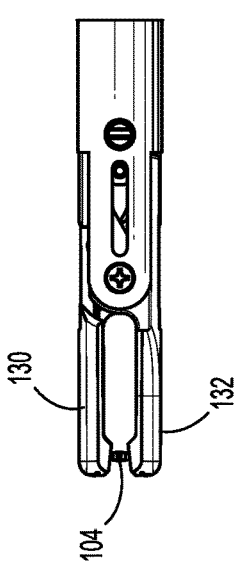

With reference now to FIGS. 10-14, initially, handles 110 are released and jaws 130, 132 are in an open position. In order to close jaws 130, 132 and swap needle 104 between jaws 130, 132, handles 110 are squeezed and main rod 156 coupled to handles 110 is displaced in the direction of arrow "p". Axial displacement of main rod 156 in the proximal direction transitions jaws 130, 132 to the closed position. If needed, jaws 130, 132 can be opened again by releasing handles 110 and needle 104 will stay in the same jaw prior to the reversal process. Continued axial displacement of main rod 156 positions pusher 412 to engage link 414. At this time, pawl 444 approaches pivot block 403, which begins the reversal process. With particular reference to FIGS. 12-13A, continued squeezing of handles 110 positions link 414 in cutout 412a of pusher 412. At this time pawl 444 engages pin 403d (FIG. 12) to rotate pivot block 403, which, in turn, causes reciprocating axial displacement of links 404, 405. The reciprocating axial displacement of links 404, 405 causes rotation of base portion 406a of cam wheel 406. As a result, first and second blade drive members 480, 482 are axially displaced in opposite directions, which, in turn, causes reciprocating axial displacement of blades 150, 152 (FIG. 5) of tool assembly 120.

Figure 14:
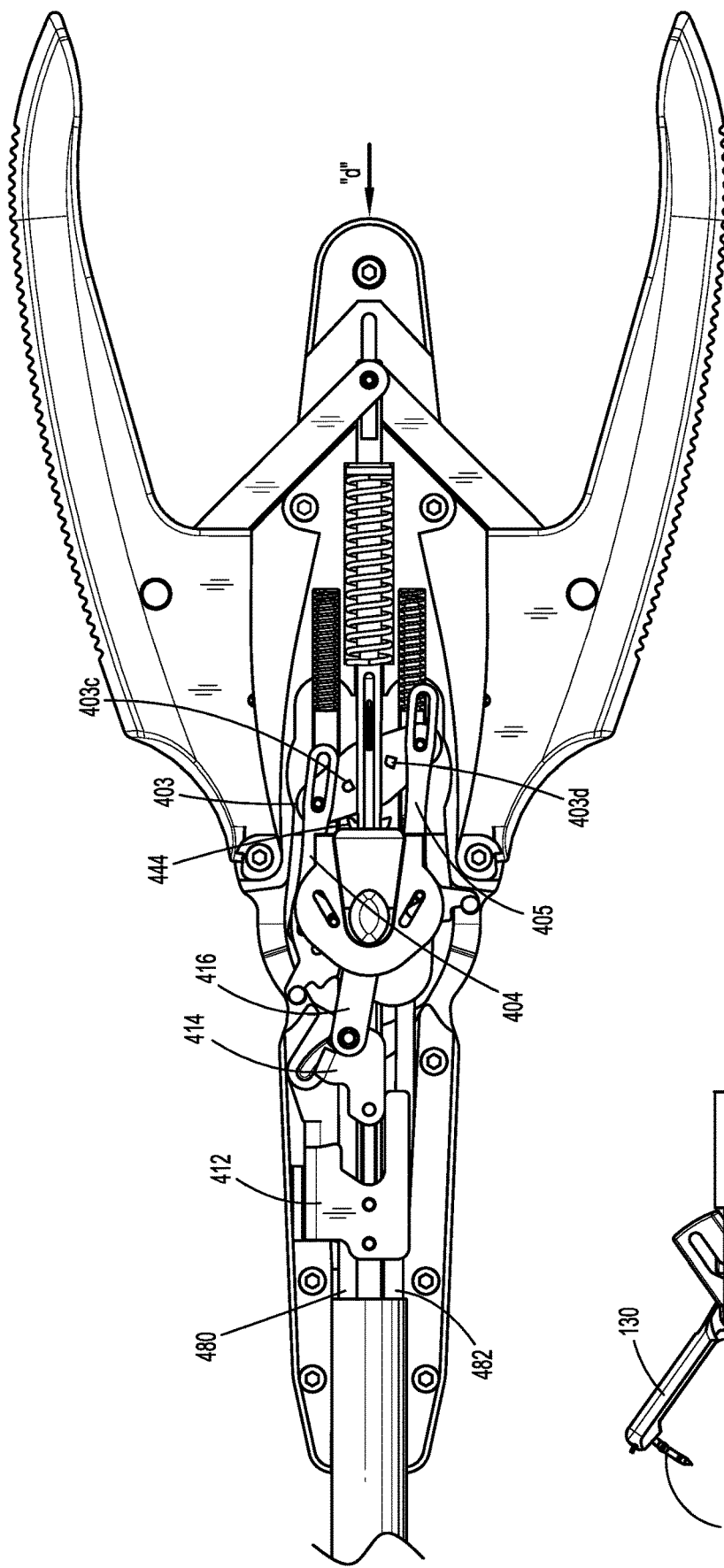
Figure 14A:
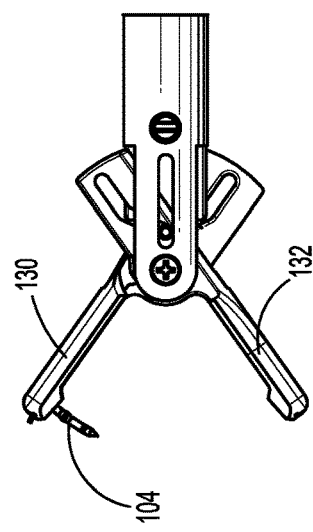

With reference to FIG. 14, at this time, handles 110 can be released to open jaws 130, 132 and retract main rod 156 to the initial position in the direction of arrow "d". When main rod 156 is retracted to the initial position, pawl 444 is moved away from pivot block 403, while pivot block 403 maintains its orientation. At this time, handles 110 may be squeezed to reverse the position of blades 150, 152. Squeezing of handles 110 at this time, advances main rod 156 proximally in the direction of arrow "p" (FIG. 11), which, in turn, causes pawl 444 to this time engage pin 403c of pivot block 403 and rotate pivot block 403 such that links 404, 405 are displaced relative to each other in opposite directions. As discussed, such reciprocating axial displacement of links 404, 405 causes rotation of base portion 406a of cam wheel 406, which, in turn, results in reciprocating axial displacement of first and second blade drive members 480, 482 in opposite directions. In this manner, blades 150, 152 may be displaced in opposite directions to swap needle 104 between jaws 130, 132. Under such a configuration, axial displacement of main rod 156 transitions jaws 130, 132 between the open and closed positions, and axially advances blades 150, 152 of tool assembly 120 in opposite directions, which eliminates the need for a manually operated toggle mechanism.

Figure 15:
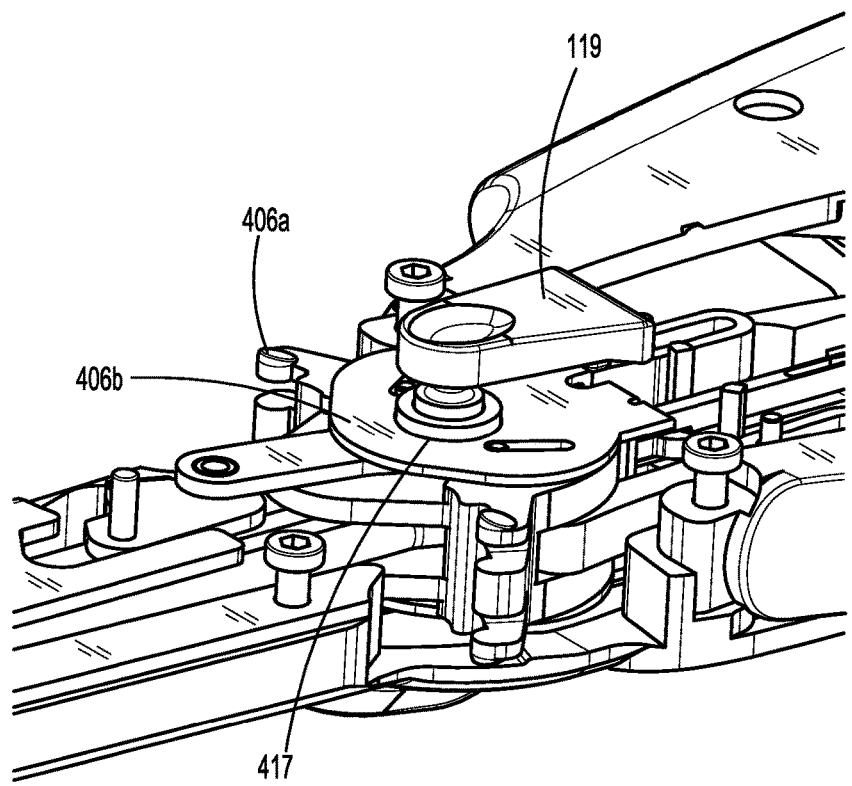
FIG. 15 is a perspective view of the drive conversion assembly of FIG. 6, illustrating attachment with a slider of the handle assembly of FIG. 1.
Figure 16:
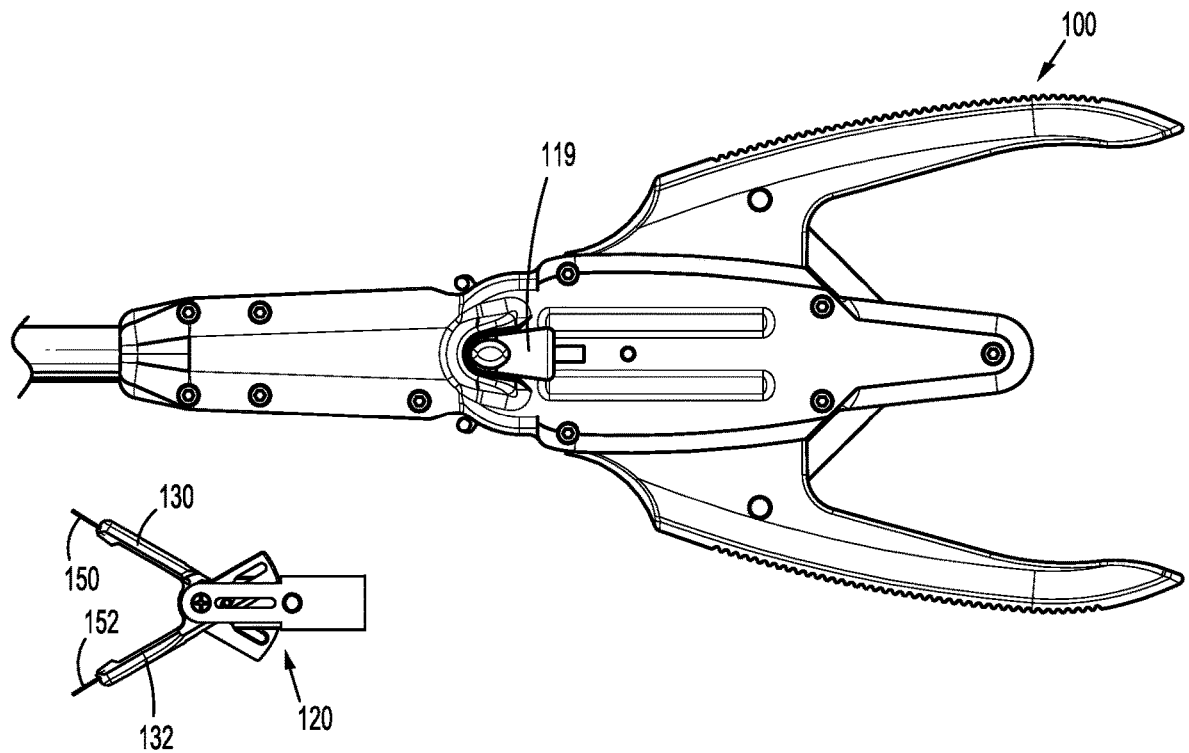
FIG. 16 is a partial top view of the stitching device of FIG. 1, illustrating a reload mode.

With reference now to FIGS. 15 and 16, handle assembly 100 further includes a slider 119 operatively coupled with drive conversion assembly 400. When slider 119 is pressed, slider 119 engages a protrusion 417 (FIG. 8) on base portion 406a of cam wheel 406 such that axial displacement of slider 119 causes concomitant displacement of cam wheel 406. While slider 119 is pressed, slider 119 may be moved proximally to place stitching device 1000 in the suture mode and distally to place stitching device 1000 in the reload mode. In the reload mode, a reversal mechanism of blades 150, 152 is disabled to inhibit reciprocating axial displacement of blades 150, 152, and to enable a loading of needle 104 into one of jaws 130, 132. Specifically, in the reload mode, links 404, 405 are in a distal position such that both blades 150, 152 are in a distal-most position. In this manner, notches formed in respective blades 150, 152 are aligned with or in registration with respective needle recesses 130a, 132a (FIG. 5) defined in respective jaws 130, 132. With the notches of blades 150, 152 aligned with or in registration with the respective needle recesses 130a, 132a, needle 104 (FIG. 2) may be positioned or loaded into a selected one needle recess 130a, 132a of jaws 130, 132.

In the suture mode, jaws 130, 132 are in the open position, and needle 104 is loaded and held in one jaw 130 or 132. Jaws 130, 132 may be positioned about or over a target tissue and handles 110 may be actuated to approximate jaws 130, 132. As jaws 130, 132 are approximated, the exposed end of needle 104 is penetrated through the target tissue and enters opposed jaw 130 or 132. With needle 104 in opposed jaw 130 or 132, pawl 444 rotates pivot block 403, which, in turn, causes reciprocating axial displacement of links 404, 405. The reciprocating axial displacement of links 404, 405 causes rotation of base portion 406a. As a result, first and second blade drive members 480, 482 are axially displaced in opposite directions, which, in turn, causes reciprocating axial displacement of blades 150, 152 (FIG. 5) of tool assembly 120. In so doing, needle 104 is swapped from one blade 150 or 152 to the other blade 150 or 152, and thus, loaded or held in the other jaw 130 or 132.

In use, stitching device 1000 is transitioned to the reload mode by sliding slider 119 (FIG. 16) distally. In this manner, first and second blade control members 480, 482 are placed in a distal position such that both blades 150, 152 (FIG. 5) are in a distal-most position. At this time, notches formed in respective blades 150, 152 are aligned with or in registration with respective needle recesses 130a, 132a (FIG. 5) defined in respective jaws 130, 132. With the notches of blades 150, 152 aligned with or in registration with the respective needle recesses 130a, 132a (FIG. 5) of respective jaws 130, 132, needle 104 (FIG. 2) may be positioned or loaded into a selected one needle recess 130a, 132a of jaws 130, 132.

Once needle 104 is loaded into one of the needle recesses 130a, 132a (FIG. 5) of jaws 130, 132, slider 119 is moved proximally to transition stitching device 1000 to the suture mode. At this time, each blade 150, 152 engages a respective groove 104a of needle 104. With needle 104 engaged by both blades 150, 152, handles 110 are actuated so that only one blade 150, 152, is in engagement with needle 104 (FIG. 5), and the other blade 150, 152 is disengaged from needle 104.

Figure 12A:
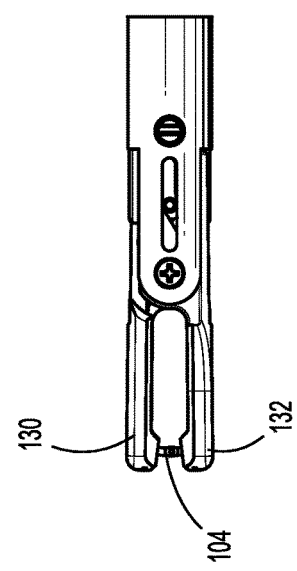

With jaws 130, 132 in the open position and needle 104 loaded and held in one jaw 130 or 132, jaws 130, 132 may be positioned about or over a target tissue. In order to close jaws 130, 132 and swap needle 104 between jaws 130, 132, handles 110 are squeezed. Main rod 156 coupled to handles 110 is displaced in the direction of arrow "p", which transitions jaws 130, 132 to the closed position (FIG. 12A). As jaws 130, 132 are approximated, the exposed end of needle 104 is penetrated through the target tissue and enters opposed jaw 130 or 132. With needle 104 in opposed jaw 130 or 132, continued squeezing of handles 110 positions link 414 in cutout 412a of pusher 412. At this time pawl 444 rotates pivot block 403, which, in turn, causes reciprocating axial displacement of links 404, 405. The reciprocating axial displacement of links 404, 405 causes rotation of base portion 406a. As a result, first and second blade drive members 480, 482 are axially displaced in opposite directions, which, in turn, causes reciprocating axial displacement of blades 150, 152 (FIG. 5) of tool assembly 120. In so doing, needle 104 is swapped from one blade 150 or 152 to the other blade 150 or 152, and thus, loaded or held in the other jaw 130 or 132. With needle 104 being swapped from one blade 150, 152 to another blade 150, 152, handles 110 may be released to thereby open jaws 130, 132 and draw needle 104 through the target tissue. In so doing, the suture is also drawn through the tissue. The process is repeated, passing needle 104 between jaws 130, 132 and drawing the suture through the target tissue, thereby suturing the target tissue as needed or desired.

Figure 17:
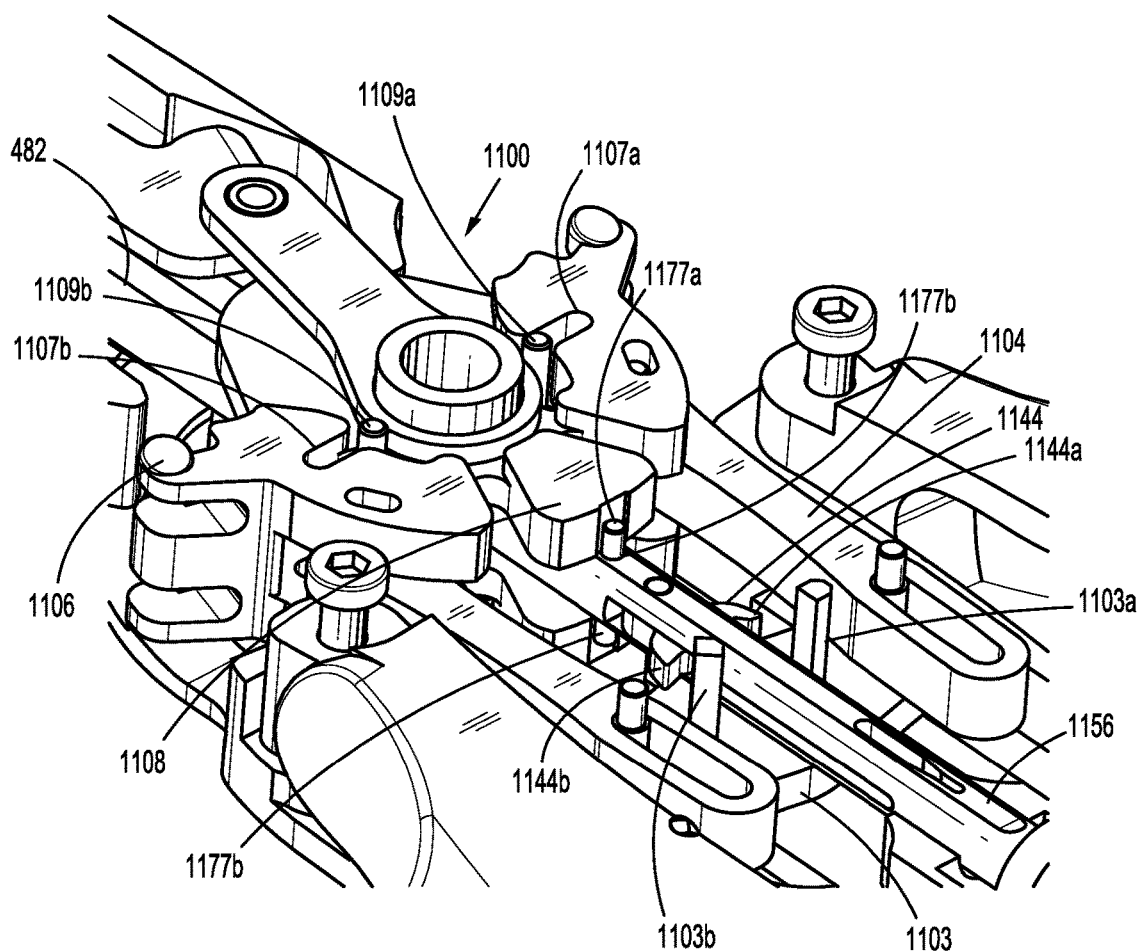
FIG. 17 is a partial perspective view of a drive conversion assembly in accordance with another embodiment of the present disclosure.
Figure 18:
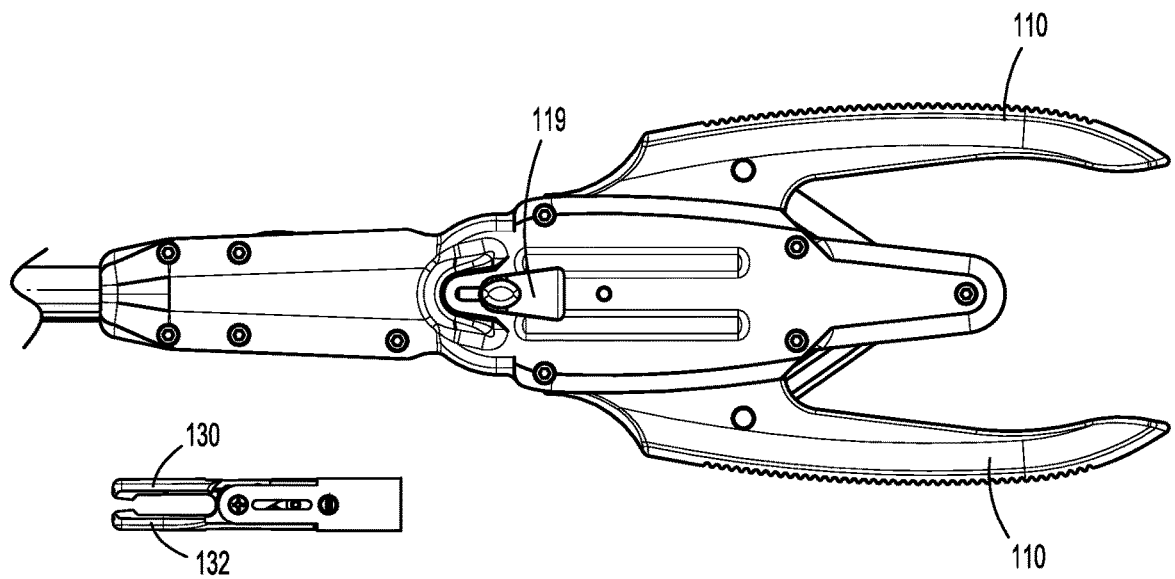
FIG. 18 is a top view of a stitching device including the drive conversion assembly of FIG. 17, illustrating the lock-out mode.

With reference now to FIGS. 17 and 18, there is illustrated a drive conversion assembly 1100 in accordance with an embodiment of the present disclosure for use with stitching device 1000. Drive conversion assembly 1100 includes features that are identical to the features described with respect to drive conversion assembly 400. Thus, the identical parts in drive conversion assembly 1100 will not be described herein to avoid obscuring the present disclosure in unnecessary detail.

As discussed hereinabove with respect to drive conversion assembly 400, drive conversion assembly 1100 is configured to convert axial displacement of a main rod 1156 operatively coupled to jaws 130, 132 into both functions of opening and closing jaws 130, 132 and providing reciprocating axial advancement of blades 150, 152, thereby eliminating the need for a separate toggle mechanism to move blades 150, 152 (FIG. 5) in opposite directions.

Drive conversion assembly 1100 is transitionable between the suture mode and the reload mode, as discussed hereinabove. Drive conversion assembly 1100, however, further enables a lock out mode, in which, jaws 130, 132 remain closed when handles 110 are prematurely released during actuation of handles 110 in the suture mode.

Main rod 1156 may be coupled to handles 110, whereby squeezing of handles 110 causes axial displacement of main rod 1156 in the direction of arrow "p". Drive conversion assembly 1100 includes a cam wheel 1106 defining camming slots 1107a, 1107b configured to receive camming pins 1109a, 1109b. Camming pins 1109a, 1109b are secured with respective proximal ends of first and second blade drive members 480, 482 (FIG. 4) coupled to blades 150, 152 (FIG. 5) of tool assembly 120. Drive conversion assembly 1100 further includes links 1104, 1105 and a pivot block 1103 pivotally supported relative to main rod 1156. Links 1104, 1105 interconnect pivot block 1103 with cam wheel 1106.

Drive conversion assembly 1100 further includes a pawl 1144 operatively coupled to main rod 1156. Opposing sides 1144a, 1144b of pawl 1144 extend transversely toward links 1104, 1105 when pawl 1144 is in a neutral position. Pawl 1144 is configured to engage one of pins 1103a, 1103b of pivot block 1103 depending on the orientation of pivot block 1103. As discussed hereinabove with respect to drive conversion assembly 400, the orientation of cam wheel 1106 is governed by axial displacement of main rod 1156, which, in turn, enables selective engagement of pawl 1144 with pins 1103a, 1103b. When pawl 1144 engages one of pins 1103a, 1103b, pivot block 1103 is rotated to cause reciprocating axial displacement of links 1104, 1105 in opposite directions.

Cam wheel 1106 includes a proximal portion 1108 including a lock out pin 1177a. Main rod 1156 includes an engaging pin 1177b (shown in phantom) configured to engage lock out pin 1177a of cam wheel 1106. In particular, lock out pin 1177a and engaging pin 1177b are configured to engage each other to inhibit distal displacement of main rod 1156 when lock out pin 1177a and engaging pin 1177b are aligned with each other. However, when lock out pin 1177a and engaging pin 1177b are misaligned or offset from each other, main rod 1156 may be displaced distally. Under such a configuration, when handles 110 are prematurely released during actuation in suture mode, lock out pin 1177a and engaging pin 1177b engage each other to inhibit opening of jaws 130, 132.

In the suture mode, jaws 130, 132 are in the open position. When handles 110 are squeezed, main rod 1156 is advanced in the direction of arrow "p", which closes jaws 130, 132. Prior to pawl 1144 engaging one of pins 1103a, 1130b, i.e., prior to reciprocating axial displacement of links 1104, 1105, cam wheel 1106 is in a first orientation such that lock out pin 1177 and engaging pin 1177b are aligned to engage each other to inhibit distal displacement of main rod 1156, which, in turn, inhibits, opening of jaws 130, 132. When handles 110 are further squeezed to enable continued axial displacement of main rod 1156 in the direction of arrow "p", to cause pawl 1144 to engage one of pins 1103a or 1103b of pivot block 1103, cam wheel 1106 is placed in a second orientation, which places lock out pin 1177a and engaging pin 1177b in a misaligned or offset position, such that when handles 110 are released main rod 1156 is displaced distally. At this time, jaws 130, 132 are again in the open position.

The method of stitching target tissue has been described hereinabove and thus will not be described herein to avoid obscuring the present disclosure in unnecessary detail.

In accordance with another embodiment of the present disclosure as illustrated with reference to FIG. 19, there is illustrated a drive conversion assembly 600 for use with stitching device 1000. Drive conversion assembly 600 includes features that are identical to the features described with respect to drive conversion assemblies 400, 1100. Thus, the identical parts in drive conversion assembly 600 will not be described herein to avoid obscuring the present disclosure in unnecessary detail.

Figure 19:
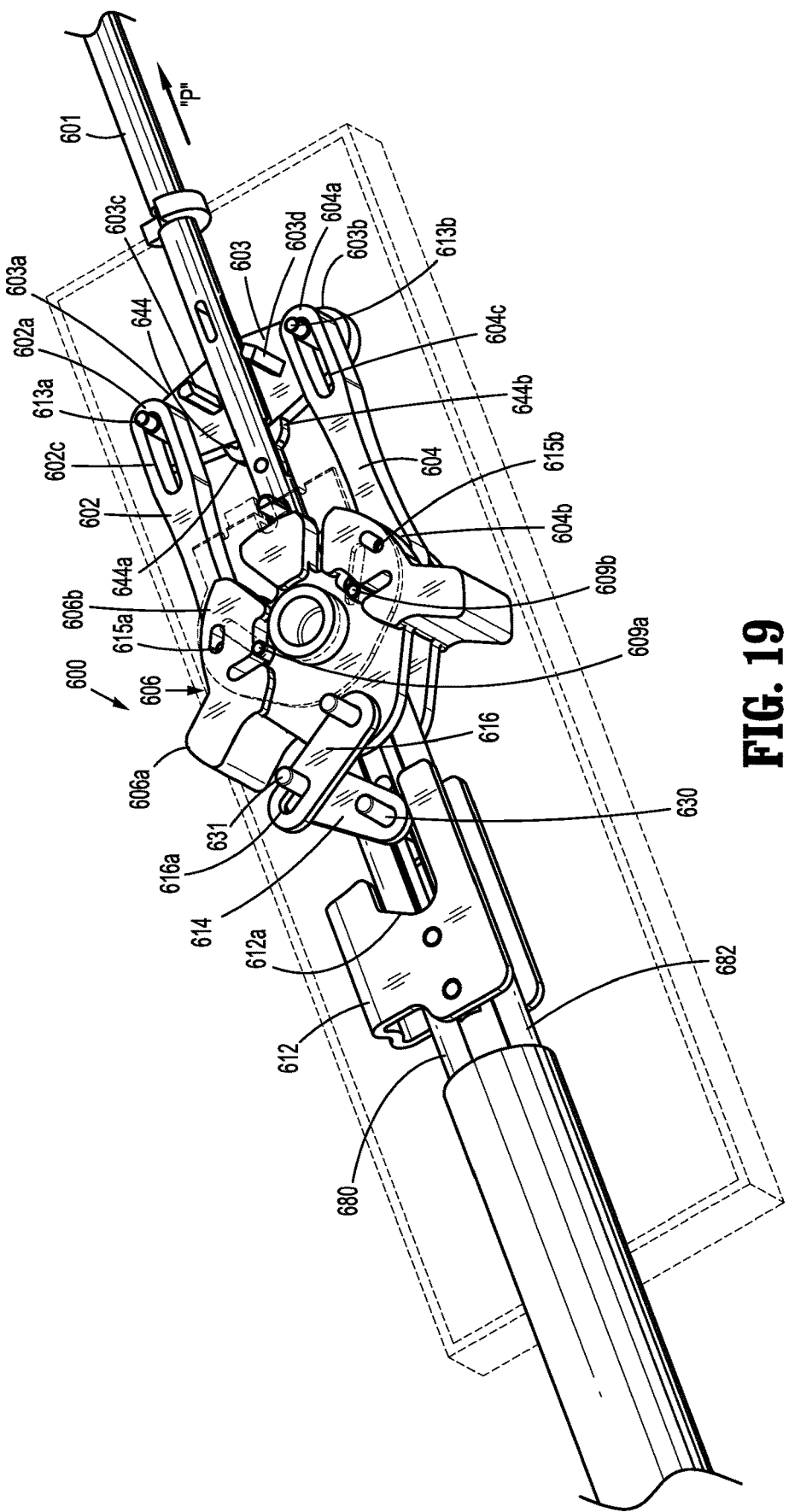
FIG. 19 is a perspective view of a drive conversion assembly in accordance with another embodiment of the present disclosure.

With reference to FIG. 19, drive conversion assembly 600 is configured to convert axial displacement of a main rod 601 operatively coupled to jaws 130, 132 (FIG. 2) into two reciprocating motions of blades 150, 152 (FIG. 5) of tool assembly 120. In this manner, axial displacement of a main rod 601 effects both functions of opening and closing jaws 130, 132 (FIG. 2) and providing reciprocating axial advancement of blades 150, 152 (FIG. 5), thereby eliminating the need for a separate toggle mechanism to move blades 150, 152 in opposite directions.

Figure 20:
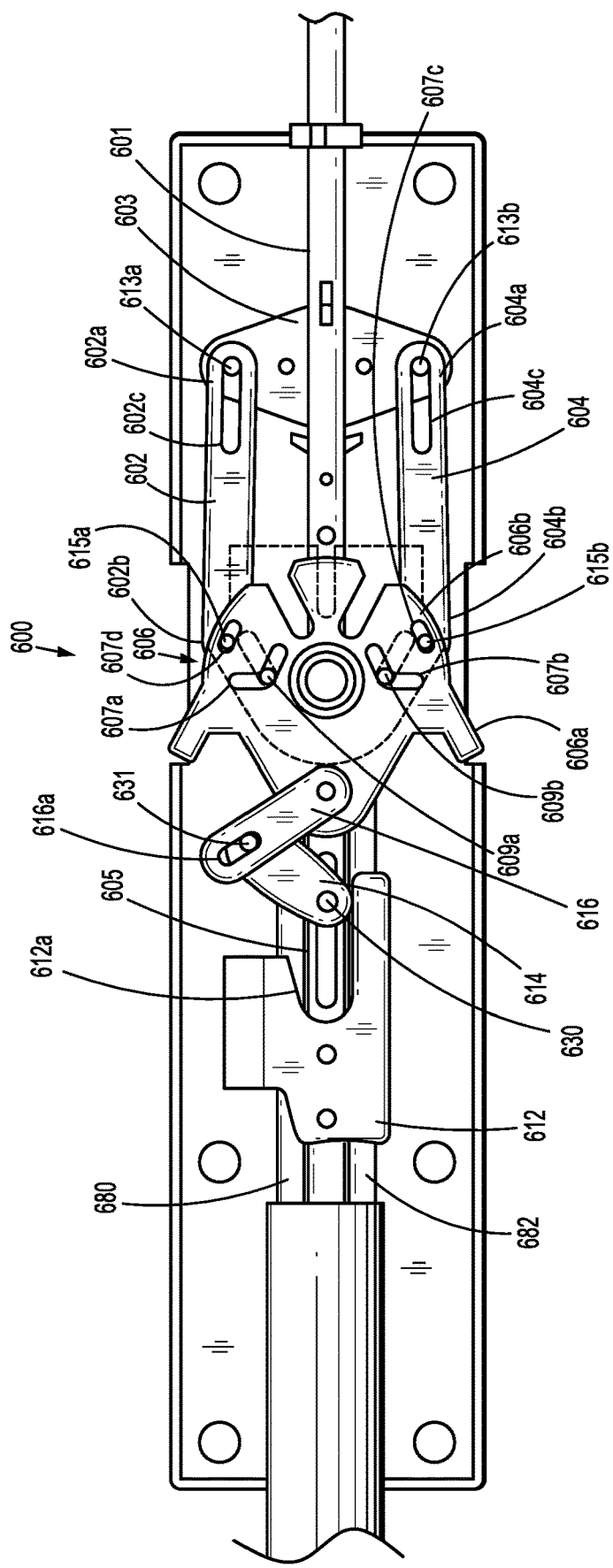
FIG. 20 is a top view of the drive conversion assembly of FIG. 19.

Main rod 601 may be operatively coupled to handles 110 (FIG. 1), whereby squeezing of handles 110 causes axial displacement of main rod 601 in the direction of arrow "p". Drive conversion assembly 600 includes a cam wheel 606 including a base portion 606a and a coupling portion 606b. Base portion 606a includes camming slots 607a, 607b (FIG. 20). Each camming slot 607a, 607b may define an L-shape extending proximally outward.

With reference to FIGS. 19 and 20, drive conversion assembly 600 further includes links 602, 604 and a pivot block 603. Each link 602, 604 includes a respective proximal portion 602a, 604a and a respective distal portion 602b, 604b. Proximal portions 602a, 604a of links 602, 604 define respective slots 602c, 604c. Each slot 602c, 604c of links 602, 604 is configured to slidably receive a pin 613a, 613b secured to one of laterally opposing sides 603a, 603b (FIG. 19) of pivot block 603. Distal portions 602b, 604b (FIG. 20) of links 602, 604 include respective pins 615a, 615b (FIG. 20). Pin 615a is configured to slidably engage camming slot 607d (FIG. 20) defined in base portion 606a of cam wheel 606, and pin 615b is configured to slidably engage camming slot 607c of base portion 606a (FIG. 20).

With continued reference to FIGS. 19 and 20, drive conversion assembly 600 further includes a pusher 612 and links 614, 616. Pusher 612 is secure with main rod 601 for concomitant movement therewith. Pusher 612 defines a cutout 612a having a shape complementary to a shape of link 614. Link 614 may have a non-uniform width. However, link 614 has a generally linear profile. In addition, a portion of main rod 601, in registration with cutout 612a of pusher 612, defines a slot 605 (FIG. 20). Link 614 includes a pin 630 slidably engaging slot 605 of main rod 601. Link 616 defines a slot 616a configured to slidably receive pin 631 secured to link 614. In addition, link 616 is pivotably couple to base portion 606a of cam wheel 606 and engages coupling portion 606b of cam wheel 606.

Camming slots 607a, 607b (FIG. 20) of base portion 606a of cam wheel 606 are configured to slidably receive camming pins 609a, 609b extending from respective first and second blade drive members 680, 682 operatively coupled to blades 150, 152 (FIG. 5). Camming pins 609a, 609b extend through respective camming slots 607a, 607b (FIG. 20) of base portion 606a and further slidably engages respective slots 617a, 617b (FIG. 21) defined in coupling portion 606b of cam wheel 606. In particular, slots 617a, 617b of coupling portion 606b of cam wheel 606 may be defined on opposing lateral sides of coupling portion 606b and may extend distally inward. Slots 607a, 607b of base portion 606a are defined on opposing lateral sides of base portion 606a and extend transversely outward in a distal direction.

Drive conversion assembly 600 further includes a pawl 644 biased to a neutral position in which opposing sides 644a, 644b of pawl 644 extend transversely from main rod 601. Pawl 644 may be spring biased toward the neutral position. Pawl 602 is configured to engage one of pins 603c, 603d depending on the orientation of pivot block 603, when main rod 601 is advanced proximally, to rotate pivot block 603, thereby providing reciprocating axial displacement of links 602, 604 in opposite directions. Reciprocating axial displacement of links 602, 604 causes rotation of cam wheel 606, which, in turn, causes reciprocating axial displacement of first and second blade drive members 680, 682 coupled to blades 150, 152 (FIG. 5) of tool assembly 120.

Figure 21:
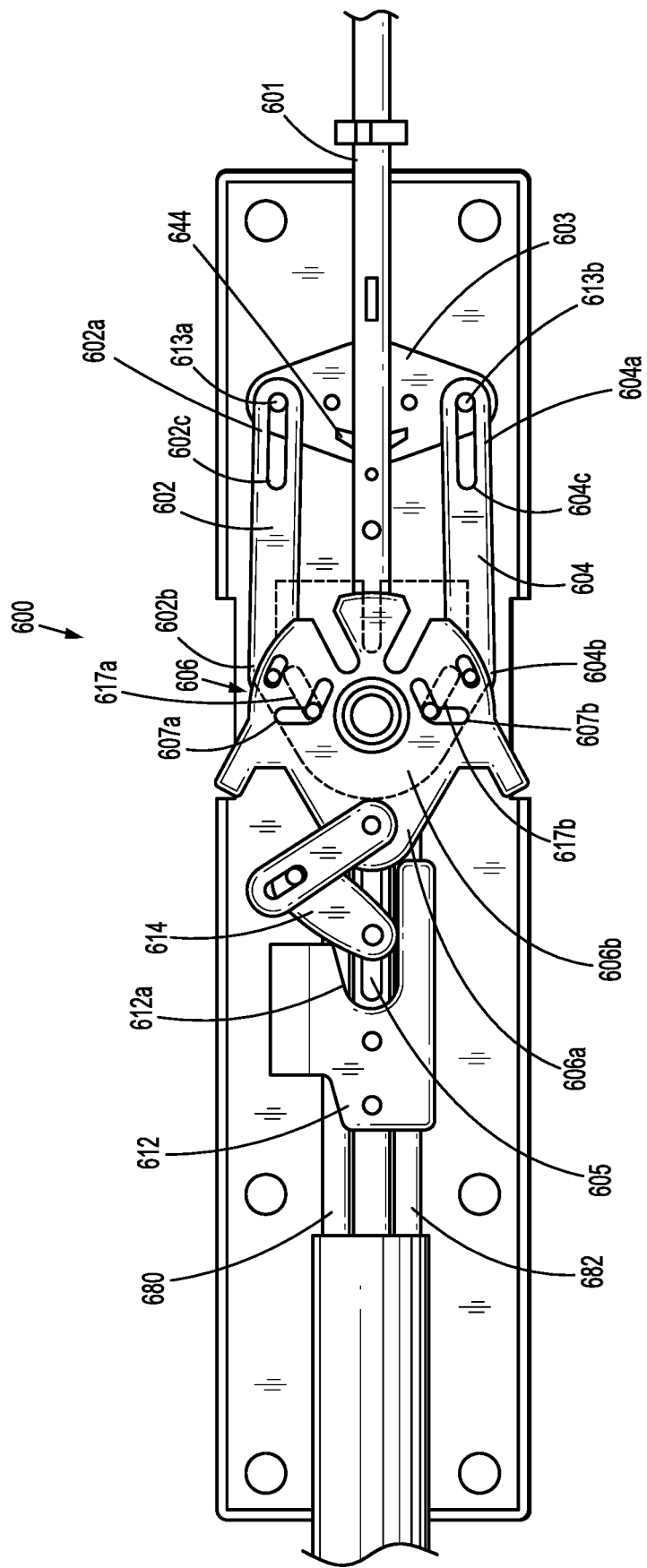
FIGS. 21-24 are top views of the drive conversion assembly of FIG. 19, illustrating axial displacement of a main rod to open and close jaws of a tool assembly of the stitching device and reciprocating axial displacement of blade drive members to effect reciprocating axial displacement of blades of FIG. 5.
Figure 22:
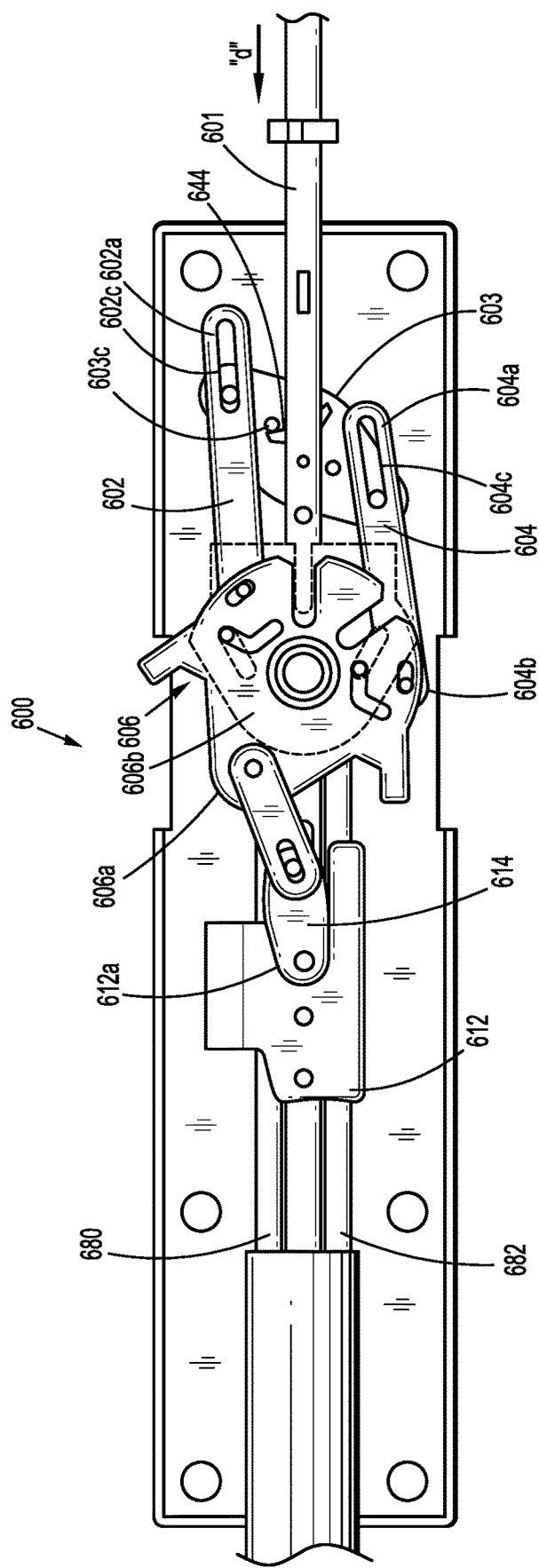

With continued reference to FIGS. 19 and 20, initially, handles 110 (FIG. 1) are released and jaws 130, 132 (FIG. 2) are in an open position. When handles 110 are squeezed, main rod 601, coupled to handles 110, is displaced in the direction of arrow "p". Axial displacement of main rod 601 in the proximal direction transitions jaws 130, 132 to the closed position. Continued axial displacement of main rod 601 positions pusher 612 to engage link 614. At this time, pawl 644 approaches pivot block 603, which begins the reversal process. With reference now to FIGS. 21 and 22, continued squeezing of handles 110 positions link 614 in cutout 612a of pusher 612. At this time pawl 644 engages pin 603c to rotate pivot block 603, which, in turn, causes reciprocating axial displacement of links 602, 604. The reciprocating axial displacement of links 602, 604 causes rotation of base portion 606a. As a result, first and second blade drive members 680, 682 are axially displaced in opposite directions, which, in turn, causes reciprocating axial displacement of blades 150, 152 (FIG. 5) of tool assembly 120.

Figure 23:
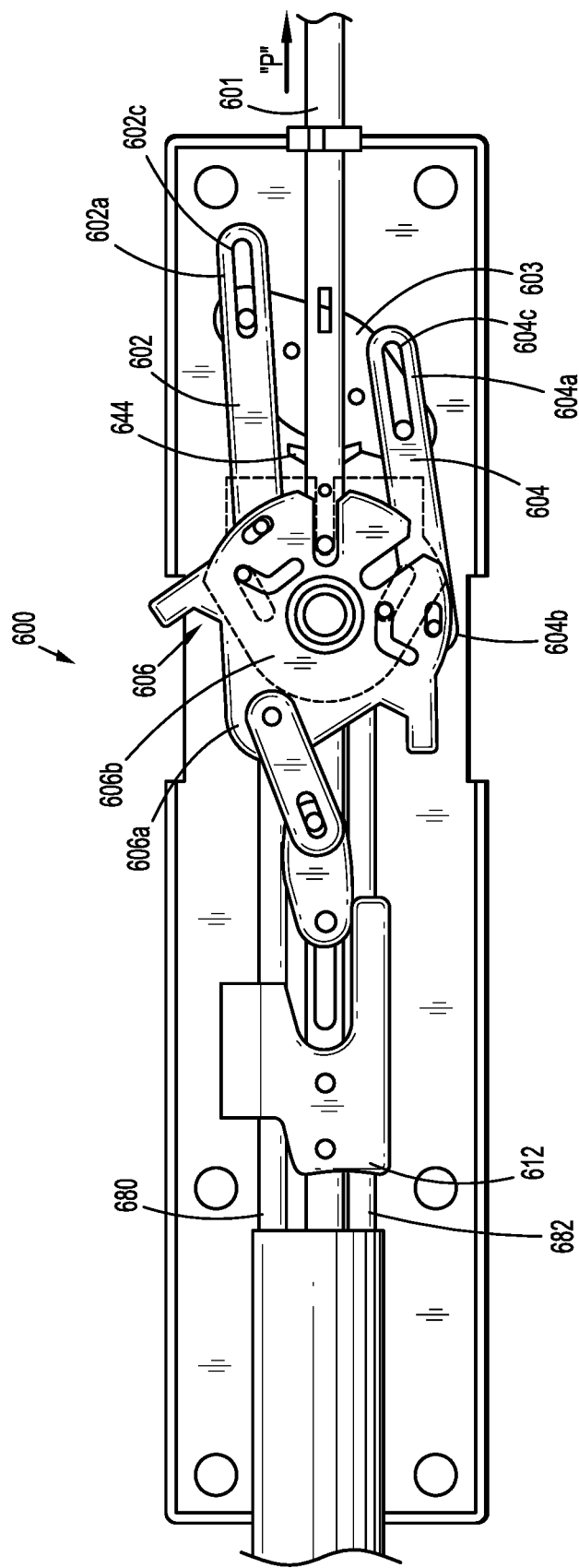
Figure 24:
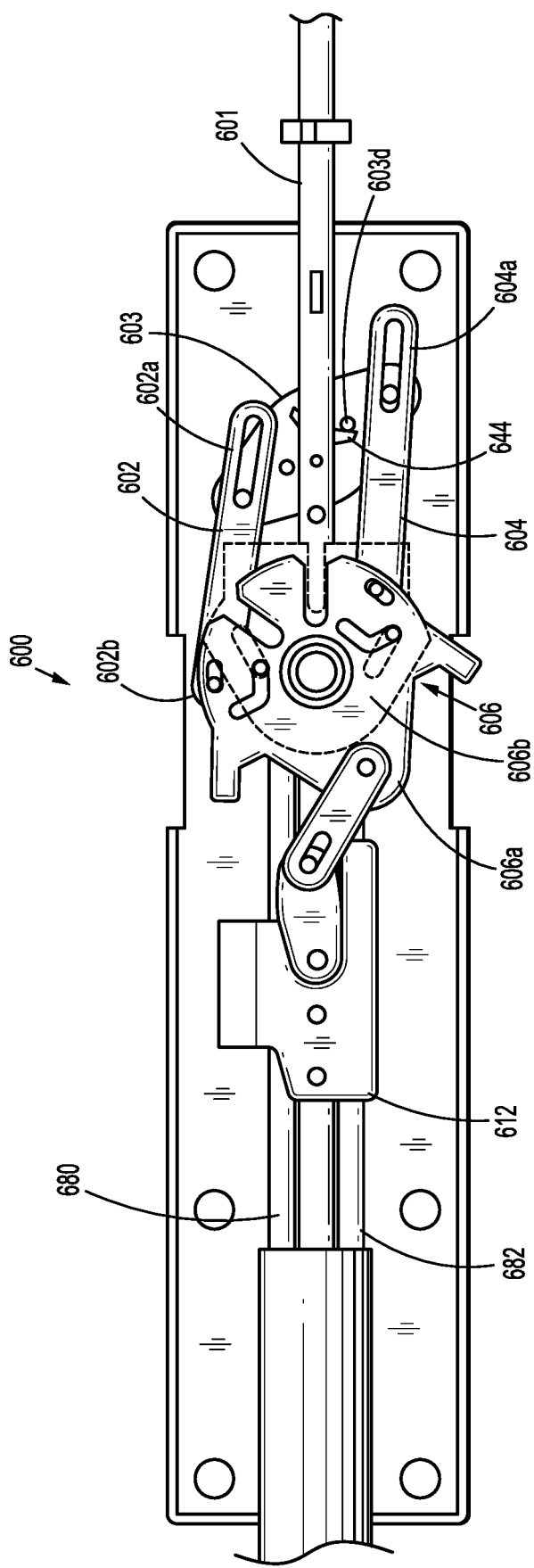
Figure 25:
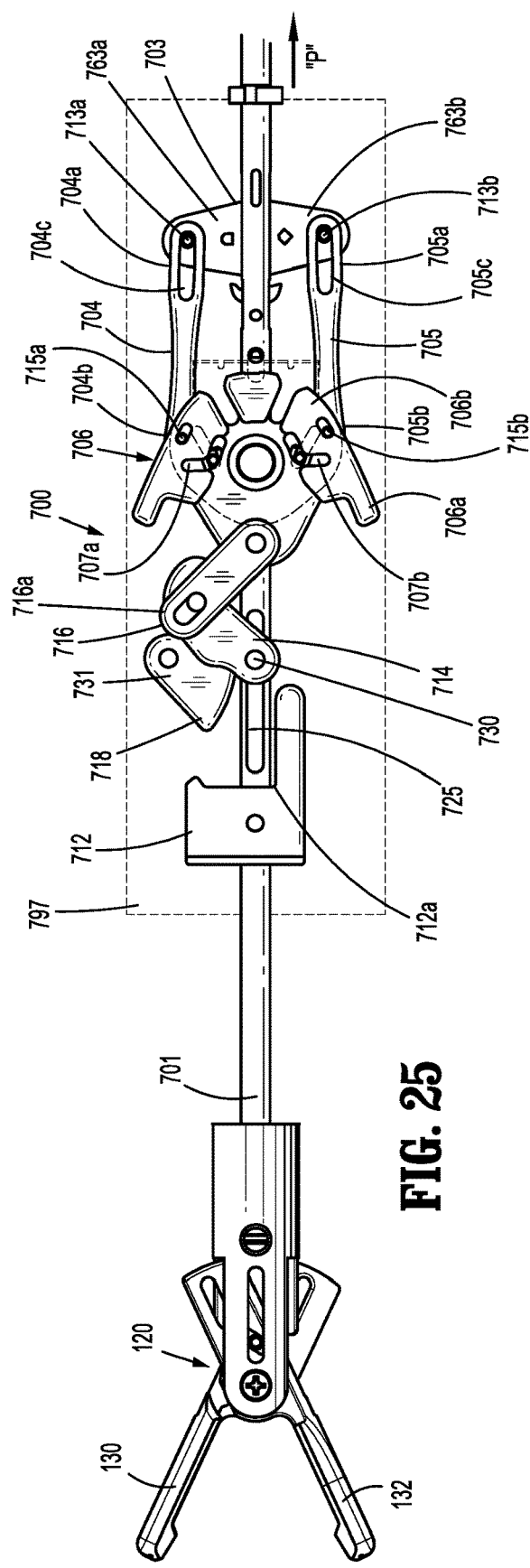
FIG. 25 is a partial top view of a stitching device including a drive conversion assembly in accordance with another embodiment of the present disclosure.

At this time, handles 110 can be released to open jaws 130, 132 and retract main rod 601 to the initial position, in the direction of arrow "d" (FIG. 22). With reference to FIGS. 23-25, when main rod 601 is retracted to the initial position, pawl 644 is moved away from pivot block 603, while pivot block 603 maintains its orientation. At this time, handles 110 may be squeezed to reverse the position of blades 150, 152. Squeezing of handles 110 at this time, advances main rod 601 proximally in the direction of arrow "p" (FIG. 23), which, in turn, causes pawl 644 to engage pin 603d (FIG. 24) of pivot block 603 and rotate pivot block 603 such that links 602, 604 are displaced relative to each other in opposite directions. As discussed, such reciprocating axial displacement of links 602, 604 causes rotation of cam wheel 606, which, in turn, results in reciprocating axial displacement of first and second blade drive members 680, 682 in opposite directions. In this manner, blades 150, 152 may be displaced in opposite directions to swap needle 104 between jaws 130, 132. Under such a configuration, axial displacement of main rod 601 transitions jaws 130, 132 between the open and closed positions, and axially advances blades 150, 152 of tool assembly 120 in opposite directions, which eliminates the need for a toggle mechanism. The method of stitching target tissue has been described hereinabove and thus will not be described herein to avoid obscuring the present disclosure in unnecessary detail.

In accordance with another embodiment of the present disclosure as illustrated in FIG. 25, there is illustrated a drive conversion assembly 700 for use with stitching device 1000. Drive conversion assembly 700 includes features that are identical to the features described with respect to drive conversion assemblies 400, 600, 1100 described hereinabove. Thus, the identical parts in drive conversion assembly 700 will not be described herein to avoid obscuring the present disclosure in unnecessary detail.

With reference to FIG. 25, drive conversion assembly 700 is configured to convert axial displacement of a main rod 701 operatively coupled to jaws 130, 132 into two reciprocating motions of blades 150, 152 (FIG. 5) of tool assembly 120. In this manner, axial displacement of main rod 401 effects both functions of opening and closing jaws 130, 132 and providing reciprocating axial advancement of blades 150, 152, thereby eliminating the need for a separate toggle mechanism to move blades 150, 152 (FIG. 5) in opposite directions.

Figure 26:
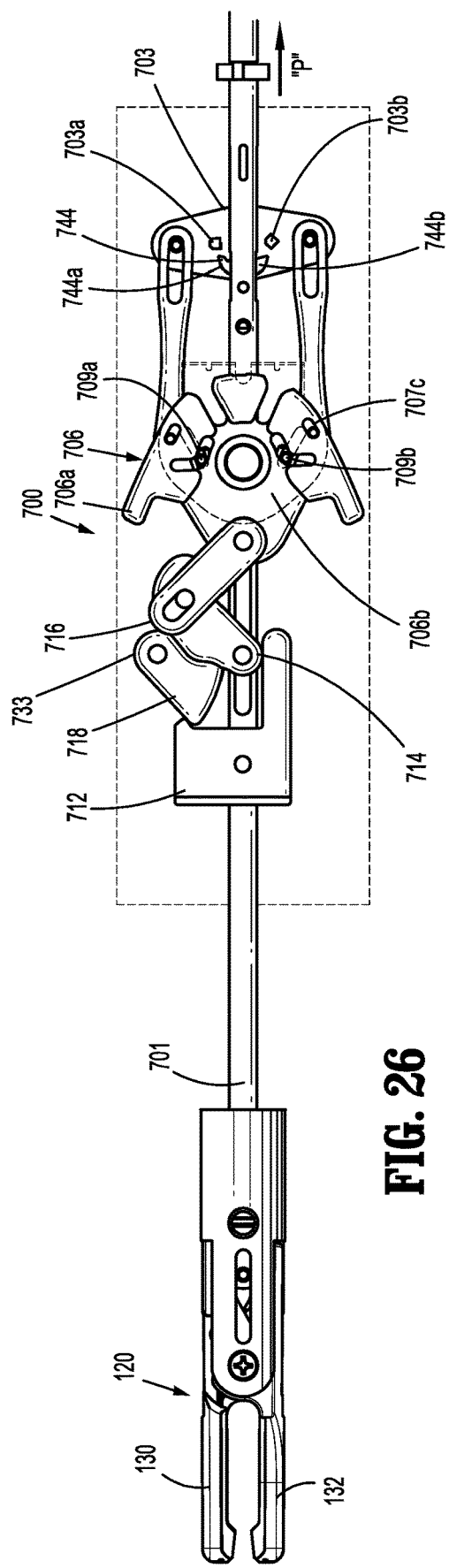
FIG. 26 is a partial top view of the stitching device of FIG. 25, illustrating axial displacement of a main rod in a proximal direction.

With reference to FIGS. 25 and 26, main rod 701 may be operatively coupled to handles 110 (FIG. 1), whereby squeezing of handles 110 causes axial displacement of main rod 701 in the direction of an arrow "p". Drive conversion assembly 700 includes a cam wheel 706 including a base portion 706a and a coupling portion 706b. Base portion 706a includes substantially L-shaped camming slots 707a, 707b. Camming slots 707a, 707b of base portion 706a extend transversely outward.

Drive conversion assembly 700 further includes links 704, 705 and a pivot block 703. Each link 704, 705 includes a proximal portion 704a, 705a and a distal portion 704b, 705b. Proximal portions 704a, 705a define respective slots 704c, 705c. Each slot 704c, 705c is configured to slidably receive respective pins 713a, 713b secured to one of laterally opposing sides 763a, 763b of pivot block 703. Distal portions 704b, 705b of links 704, 705 include respective pins 715a 715b. Pin 715a of link 704 is configured to slidably engage camming slot 707d (FIG. 30) defined in base portion 706a of cam wheel 706. Pin 715b of link 705 is configured to slidably engage camming slot 707c (FIG. 26) defined in base portion 706a of cam wheel 706.

Figure 27:
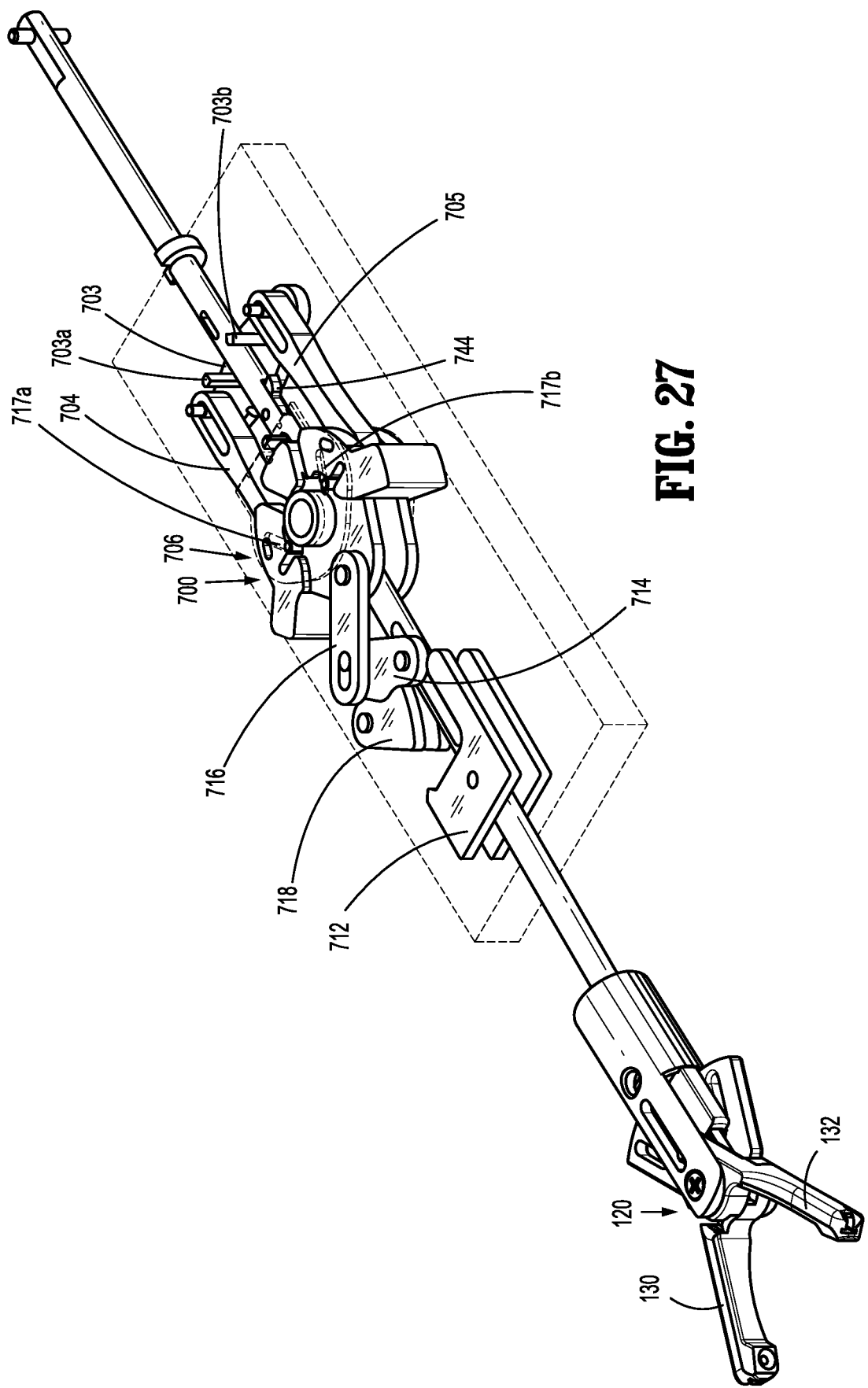
FIGS. 27 and 28 are partial perspective views of the stitching device of FIG. 25, illustrating axial displacement of the main rod in the proximal direction.
Figure 28:
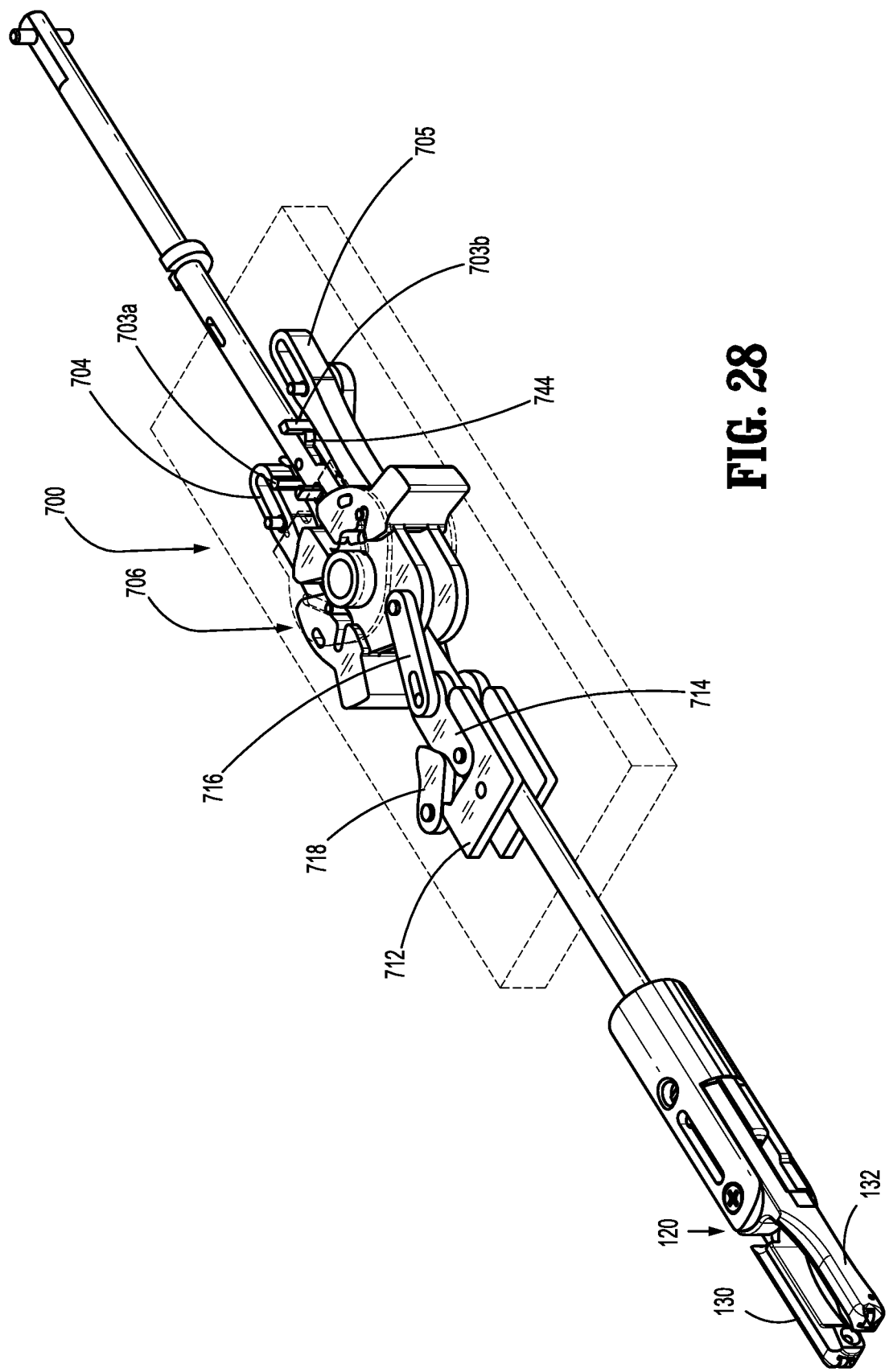

Drive conversion assembly 700 further includes a pusher 712 and links 714, 716, 718. Pusher 712 is secured with main rod 701 for concomitant movement therewith. Pusher 712 defines an L-shaped profile with an arcuate cutout 712a configured to receive a portion of link 714. Link 714 includes a pin 730 slidably engaging slot 725 defined in main rod 701. Link 716 defines a slot 716a configured to slidably receive pin 731 secured to link 714. In addition, link 716 is pivotably coupled to base portion 706a of cam wheel 706. Link 718 is pivotally secured on hub 797 by a pin 733 (FIG. 26). Link 718 is positioned to engage pusher 712 when pusher 712 is displaced proximally in the direction of arrow "p". Proximal displacement of pusher 712 pushes link 718 to cause links 714, 716 to be aligned with main rod 701 (FIG. 29) such that link 718 is transverse to links 714, 716. Camming slots 707a, 707b of base portion 706a of cam wheel 706 are configured to slidably receive camming pins 709a, 709b (FIG. 26) extending from respective first and second blade drive members 480, 482 (FIG. 4) operatively coupled to blades 150, 152 (FIG. 5) of tool assembly 120. Camming pins 709a, 709b extend through respective camming slots 707a, 707b (FIG. 25) of base portion 706a and slidably engage respective slots 717a, 717b (FIG. 27) defined in coupling portion 706b of cam wheel 706. In particular, slots 717a, 717b of coupling portion 706b of cam wheel 706 may be defined on opposing lateral sides of coupling portion 706b and may extend distally inward. Slots 707a, 707b (FIG. 25) of base portion 706a are defined on opposing lateral sides of base portion 706a and extend transversely outward in a distal direction.

Drive conversion assembly 700 further includes a pawl 744 (FIG. 26) biased to a neutral position in which opposing sides 744a, 744b of pawl 744 extend transversely from main rod 701. Pawl 744 may be coupled to main rod 701 by a spring (not shown). Pawl 744 is configured to engage one of pins 703a, 703b (FIG. 26) depending on the orientation of pivot block 703, whereby engagement of one of pins 703a, 703b of pivot block 703 with pawl 744 rotates pivot block 703, which, in turn, reverses axial displacement of links 704, 705 in opposite directions, as will be described hereinbelow.

Figure 41:
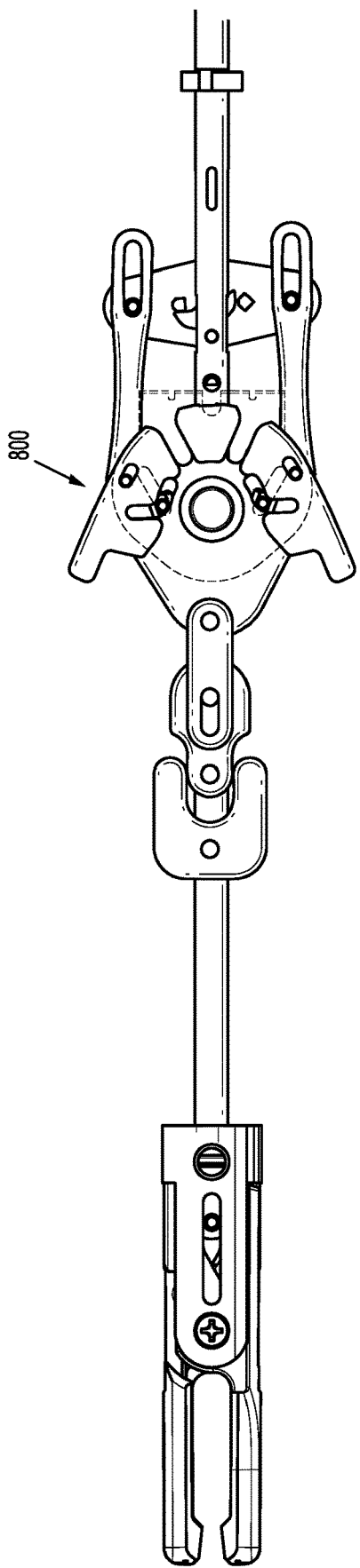
Figure 42:
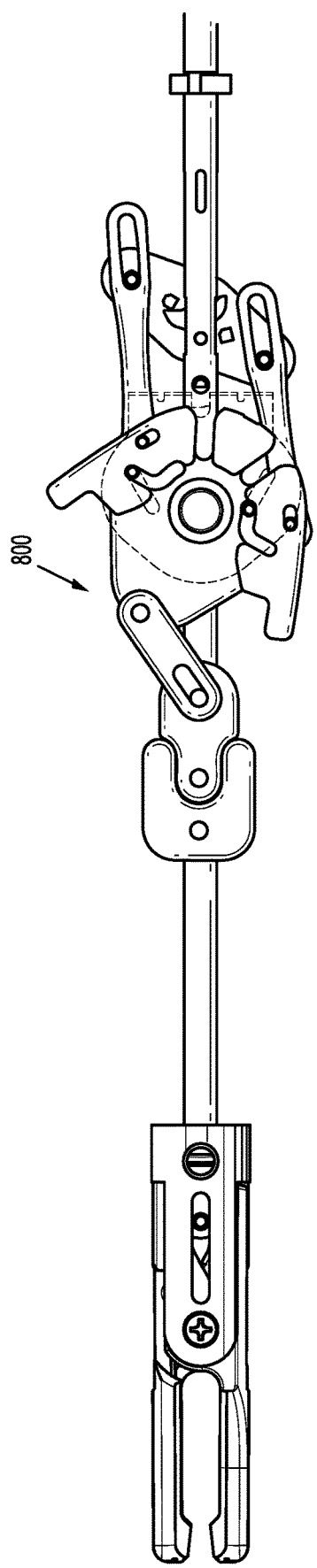

With reference to FIGS. 41 and 42, initially, jaws 130, 132 are in an open position and cam wheel 706 is in a reload position, in which needle 104 (FIG. 2) can be positioned in one of jaws 130, 132. When handles 110 are squeezed, main rod 701 coupled to handles 110, is displaced in a direction of arrow "p". Axial displacement of main rod 701 in the proximal direction transitions jaws 130, 132 to the closed position and pusher 712 is moved toward links 714, 716, 718. At this time, pawl 744 is moved toward pivot block 703.

With reference now to FIGS. 27-30, continued squeezing of handles 110 causes pusher 712 to push link 718 which urges links 714, 716 to align with main rod 701, and pawl 744 to engage pin 703b of pivot block 703. With reference to FIG. 29, engagement of pawl 744 with pin 703b causes rotation of pivot block 703 such that links 704, 705 are axially displaced with respect to each other in opposite directions to cause reciprocating axial displacement of blades 150, 152 (FIG. 5) in opposite directions. As discussed hereinabove with respect to drive conversion assemblies 400, 600, 1100, handles 110 may be released and squeezed again to reverse the orientation of links 704, 705 by engaging pawl 744 with pin 703a of pivot block 703 to change the orientation of pivot block 703, thereby providing reciprocating displacement of blades 150, 152 in tool assembly 120 in opposite directions. The method of stitching target tissue has been described hereinabove and thus will not be described herein to avoid obscuring the present disclosure in unnecessary detail.

Figure 32:
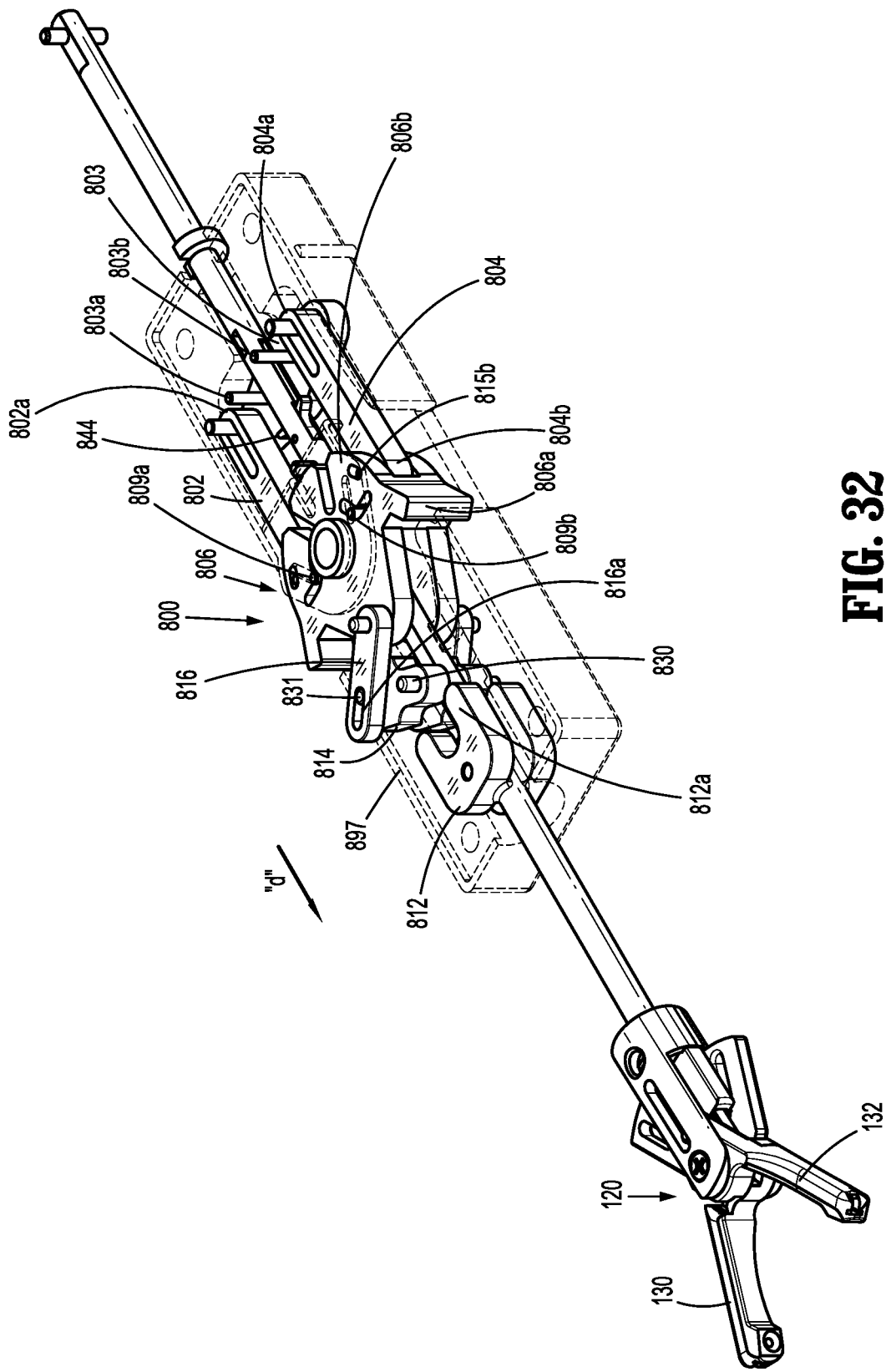
FIG. 32 is a partial, perspective view of the stitching device of FIG. 31, illustrating the drive conversion assembly in a reload mode.

In accordance with another embodiment of the present disclosure as illustrated in FIGS. 31 and 32, there is illustrated a drive conversion assembly 800 for use with stitching device 1000. Drive conversion assembly 800 includes features that are identical to the features described with respect to drive conversion assemblies 400, 600, 700, 1100. Thus, the identical parts in drive conversion assembly 800 will not be described herein to avoid obscuring the present disclosure in unnecessary detail.

Drive conversion assembly 800 is configured to convert axial displacement of a main rod 801 operatively coupled to jaws 130, 132 into two reciprocating motions of blades 150, 152 (FIG. 5) of tool assembly 120. In this manner, axial displacement of main rod 801 effects both functions of opening and closing jaws 130, 132 and providing reciprocating axial advancement of blades 150, 152 (FIG. 5), thereby eliminating the need for a separate toggle mechanism, to move blades 150, 152 (FIG. 5) in opposite directions.

With reference to FIGS. 31 and 32, main rod 801 may be operatively coupled to handles 110 (FIG. 1), whereby squeezing of handles 110 causes axial displacement of main rod 801. Drive conversion assembly 800 is selectively transitionable between an operational mode (FIG. 31) and a reload mode (FIG. 32). When drive conversion assembly 800 is in the operational mode (FIG. 31), squeezing of handles 110 opens and closes jaws 130, 132 and causes reciprocating axial displacement of blades 150, 152 of tool assembly 120 such that needle 104 (FIG. 5) may be swapped between jaws 130, 132. In the reload mode (FIG. 32), a reversal mechanism of blades 150, 152 is disabled to inhibit reciprocating axial displacement of blades 150, 152, and to enable a loading of needle 104 into one of jaws 130, 132. Drive conversion assembly 800 may be selectively transitioned from the operational mode to the reload mode by advancing a cam wheel 806 distally in the direction of arrow "d" (FIG. 32), which inhibits rotation of cam wheel 806. It is contemplated that hub 897 may be provided with a slider or a button (not shown) to advance cam wheel 806 distally to the reload mode. Additionally, it is further contemplated that the slider or the button may be frictionally locked or may include a ratchet mechanism that maintains the position of the slider or the button in order to maintain the reload mode. However, it is also envisioned that the slider or button may be released when main rod 801 is pulled proximally by actuation of handles 110.

With continued reference to FIGS. 31 and 32, drive conversion assembly 800 includes cam wheel 806 including a base portion 806a and a coupling portion 806b. Base portion 806a includes substantially L-shaped camming slots 807a, 807b (FIG. 39). Camming slots 807a, 807b extend transversely outward. Drive conversion assembly 800 further includes links 802, 804 and a pivot block 803. Each link 802, 804 includes a proximal portion 802a, 804a and a distal portion 802b, 804b (FIGS. 32 and 35). Proximal portions 802a, 804a define respective slots 802c, 804c (FIG. 31). Each slot 802c, 804c is configured to slidably receive a respective pin 813a, 813b secured to one of laterally opposing sides of pivot block 803. Distal portions 802b, 804b (FIGS. 31 and 35) of links 802, 804 include respective pins 815a, 815b (FIG. 31). Pin 815a is configured to slidably engage camming slot 807d (FIG. 36) defined in base portion 806a of cam wheel 806. Pin 815b is configured to slidably engage camming slot 807c (FIG. 38) also defined in base portion 806a.

Figure 33:
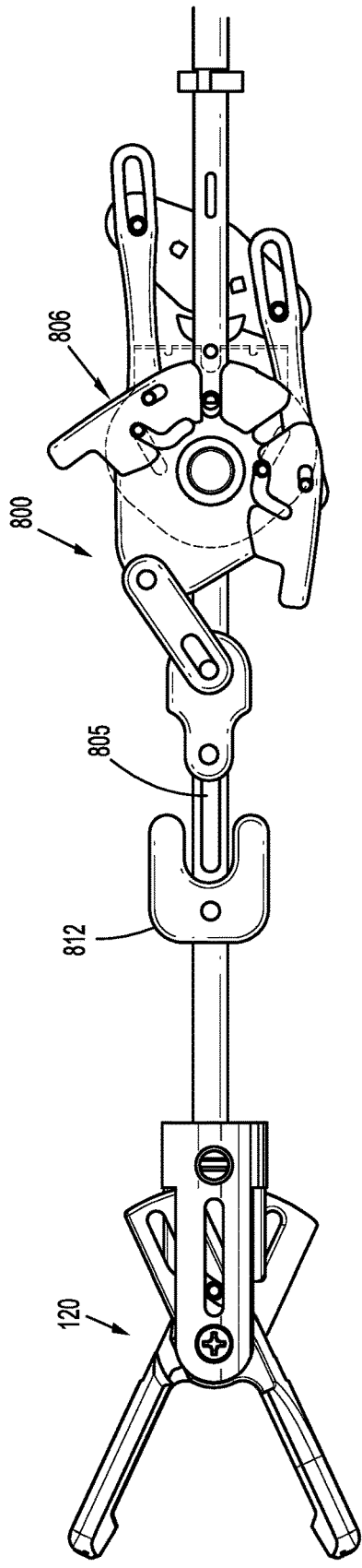

With continued reference to FIGS. 31 and 32, drive conversion assembly 800 further includes a pusher 812 and links 814, 816. Pusher 812 is secure with main rod 801 for concomitant movement therewith. Pusher 812 defines a cutout 812a having, e.g., a U-shape, complementary to a shape of link 814. In addition, a portion of main rod 801, in registration with cutout 812a of pusher 812, defines a slot 805 (FIG. 33). Link 814 includes a first pin 830 slidably engaging slot 805 (FIG. 33) of main rod 801. Link 816 defines a slot 816a configured to slidably receive a second pin 831 secured to link 814. In addition, link 816 is pivotably couple to base portion 806a of cam wheel 806. Camming slots 807a, 807b (FIG. 39) of base portion 806a of cam wheel 806 are configured to slidably receive camming pins 809a, 809b (FIG, 33) extending from respective first and second blade drive members 480, 482 (FIG. 4 shown) operatively coupled with respective blades 150, 152 of tool assembly 120. Camming pins 809a, 809b extend through respective camming slots 807a, 807b of base portion 806a and further cammingly engage respective slots 817a, 817b (FIG. 39) defined in coupling portion 806b of cam wheel 806. In particular, slots 817a, 817b (FIG. 39) of coupling portion 806b of cam wheel 806 may be defined on opposing lateral sides of coupling portion 806b and may extend distally inward. Slots 807a, 807b (FIG. 39) of base portion 806a are defined on opposing lateral sides of base portion 806a and extend transversely outward in a distal direction.

Drive conversion assembly 800 further includes a pawl 844 biased to a neutral position in which opposing sides of pawl 844 extend transversely from main rod 801. Pawl 844 may be operatively coupled to main rod 801 and spring biased toward the neutral position. Pawl 844 is configured to engage one of pins 803a, 803b depending on the orientation of pivot block 803, whereby engagement of pin 803a, 803b with pawl 844 rotates pivot block 803, which, in turn, reverses axial displacement of links 804, 805 in opposite directions, as will be described hereinbelow.

Figure 34:
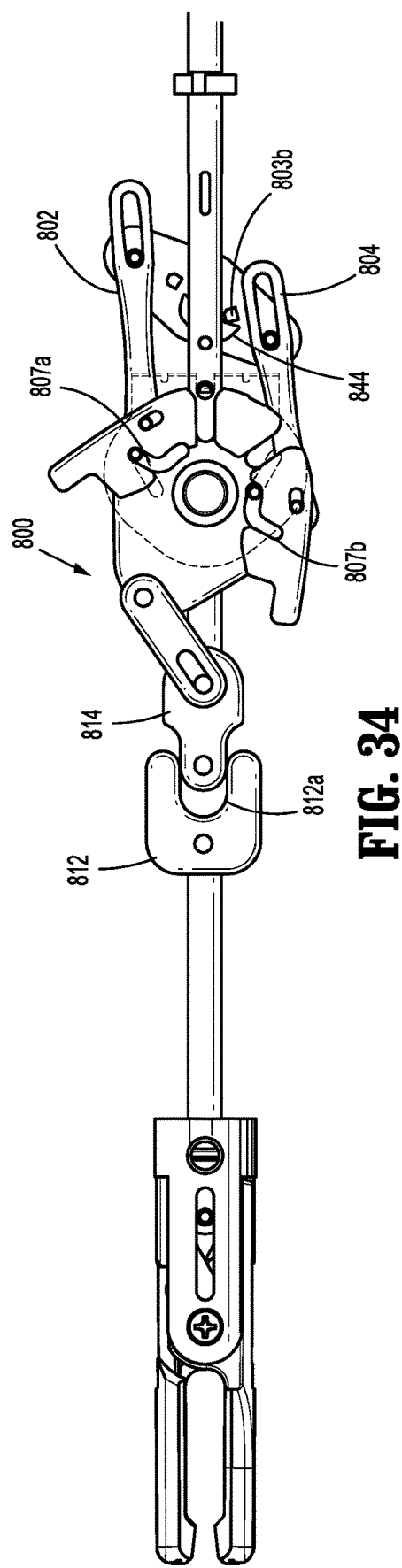

With reference to FIGS. 31 and 32, drive conversion assembly 800 is in the operational mode in which jaws 130, 132 are in the open position and cam wheel 806 is in a position. When handles 110 are squeezed, main rod 801 coupled to handles 110 (FIG. 1) is advanced in a direction of arrow "p". With reference to FIG. 34, axial displacement of main rod 801 in the proximal direction transitions jaws 130, 132 to the closed position (FIG. 34). With reference now to FIGS. 34 and 35, continued axial displacement of main rod 801 positions link 814 within cutout 812a of pusher 812. At this time, pawl 844 approaches pivot block 803, which begins the reversal process. Pawl 844 engages pin 803b and causes pivot block 803 to rotate, whereby links 802, 804 are axially displaced from each other in opposite directions to cause axial displacement of first and second blade drive members 480, 482 (FIG. 4) coupled to blades 150, 152 (FIG. 5), which, in turn, causes reciprocating axial displacement of blades 150, 152 in tool assembly 120.

With reference to FIG. 36, at this time, handles 110 are released and main rod 801 is advanced distally in the direction of arrow "d" to the initial position. When main rod 801 is advanced to the initial position, pawl 844 is moved away from pivot block 803. With reference to FIGS. 37 and 38, at this time, handles 110 may be squeezed to reverse the position of blades 150, 152. Squeezing of handles 110 at this time causes jaws 130, 132 to close and main rod 801 to advance proximally in the direction of arrow "p", which, in turn, causes pawl 844 to this time engage pin 803a and rotate pivot block 803 such that links 802, 804 are axially displaced in opposite directions, which, in turn, causes blades 150, 152 (FIG. 5) of tool assembly 120 to be axially displaced in opposite directions.

With reference to FIG. 39, as discussed hereinabove, by using a slider or a button (not shown), cam wheel 806 may be moved distally to place drive conversion assembly 800 in the reload mode. With reference to FIGS. 40-42, upon reloading needle 104 (FIG. 2) in one of jaws 130 or 132, main rod 801 may be advance proximally by, e.g., squeezing handles 110, to place drive conversion assembly 800 in the operational mode.

Under such a configuration, axial displacement of main rod 801 effects opening and closing of jaws 130, 132, as well as providing axial displacement of blades 150, 152 in tool assembly 120, which eliminates a toggle mechanism.

The method of stitching target tissue has been described hereinabove and thus will not be described herein to avoid obscuring the present disclosure in unnecessary detail.

In accordance with another embodiment of the present disclosure, there is illustrated a drive conversion assembly 1400 for use with stitching device 1000. Drive conversion assembly 1400 includes features that are identical to previously described drive conversion assemblies 400, 600, 700, 800, 1100. Identical constructions will not be described in detail to avoid obscuring the present disclosure in unnecessary detail.

Figure 43:
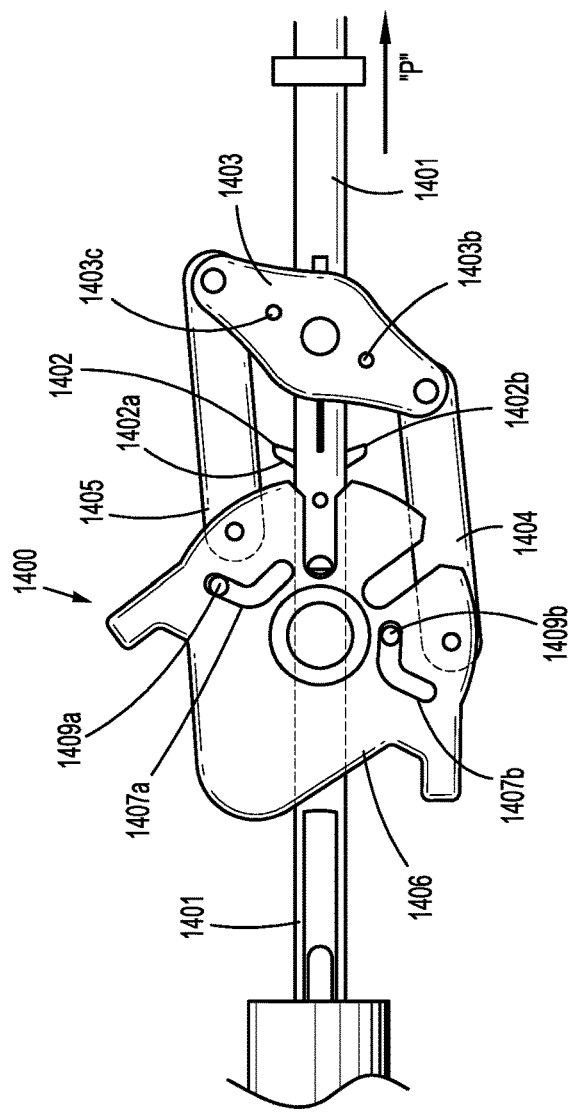
FIG. 43 is a partial top view of a drive conversion assembly in accordance with an embodiment of the present disclosure.
Figure 45:
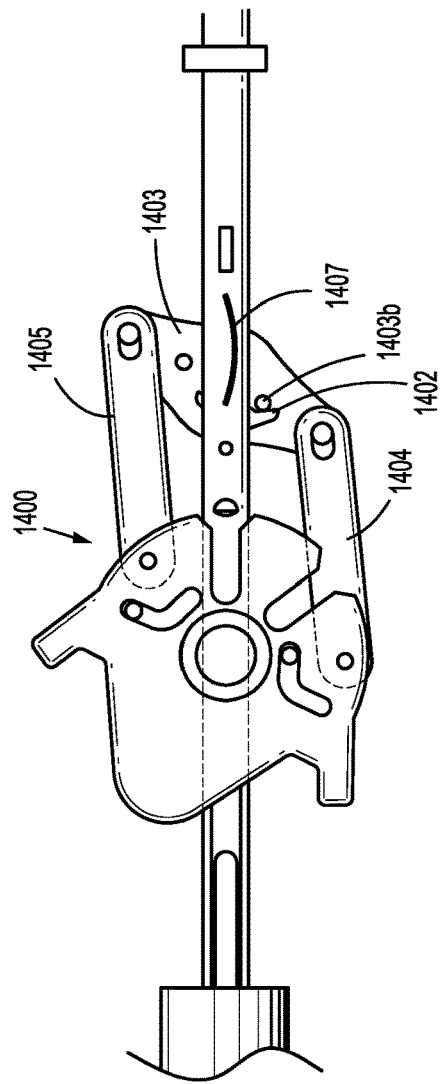
FIG. 45 is a top view of the drive conversion assembly of FIG. 43, illustrating axial displacement of a main rod in a proximal direction.
Figure 44:
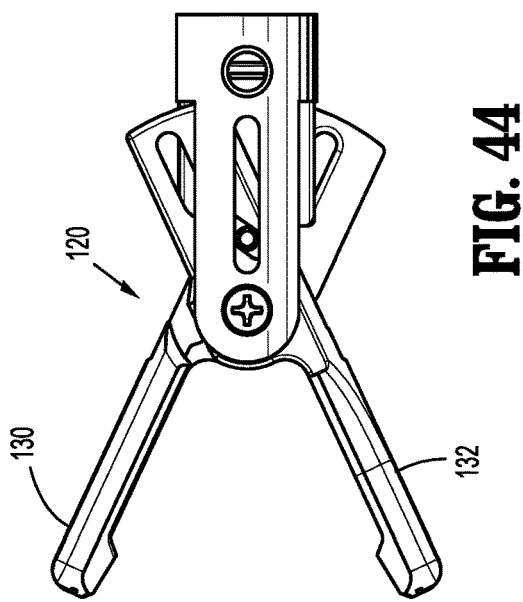
FIG. 44 is a top view of a tool assembly for use with the drive conversion assembly of FIG. 43, illustrating jaws thereof in an open position.

With reference to FIGS. 43 and 44, drive conversion assembly 1400 is configured to convert axial displacement of a main rod 1401 operatively coupled to jaws 130, 132, into two reciprocating motions of blades 150, 152 (FIG. 5) of tool assembly 120. In this manner, axial displacement of main rod 1401 effects both functions of opening and closing jaws 130, 132 and providing reciprocating axial displacement of blades 150, 152, thereby eliminating the need for a separate toggle mechanism to move blades 150, 152 (FIG. 5) in opposite directions.

With continued reference to FIGS. 43 and 44, main rod 1401 may be coupled to handles 110 (FIG. 1), whereby squeezing of handles 110 causes axial displacement of main rod 1401 in the direction of arrow "p". Drive conversion assembly 1400 includes a cam wheel 1406 defining camming slots 1407a, 1407b configured to receive camming pins 1409a, 1409b secured with first and second blade drive members 480, 482 (FIG. 4). Drive conversion assembly 1400 further includes links 1404, 1405 and a pivot block 1403 rotatable relative to main rod 1401. Links 1404, 1405 interconnect pivot block 1403 with cam wheel 1406. Drive conversion assembly 1400 further includes a pawl 1402 operatively coupled to main rod 1401. Pawl 1402 includes opposing sides 1402a, 1402b extending radially outward toward respective links 1404, 1405 when pawl 1402 is in a neutral position (FIG. 43). Pawl 1402 may be spring biased toward the neutral position (FIG. 43). Opposing sides 1402a, 1402b of pawl 1402 are configured to engage respective pins 1403b, 1403c depending on the orientation of pivot block 1403, to cause rotation of pivot block 1403, thereby reversing axial displacement of links 1404, 1405 in opposite directions, as will be described hereinbelow. Drive conversion assembly 1400 may not include a pusher and links associated with the pusher, such as those shown in FIG. 6.

Figure 46:
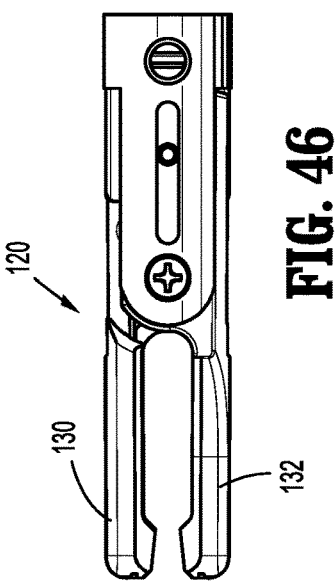
FIG. 46 is a top view of the tool assembly of FIG. 44, illustrating the jaws in a closed position.
Figure 47:
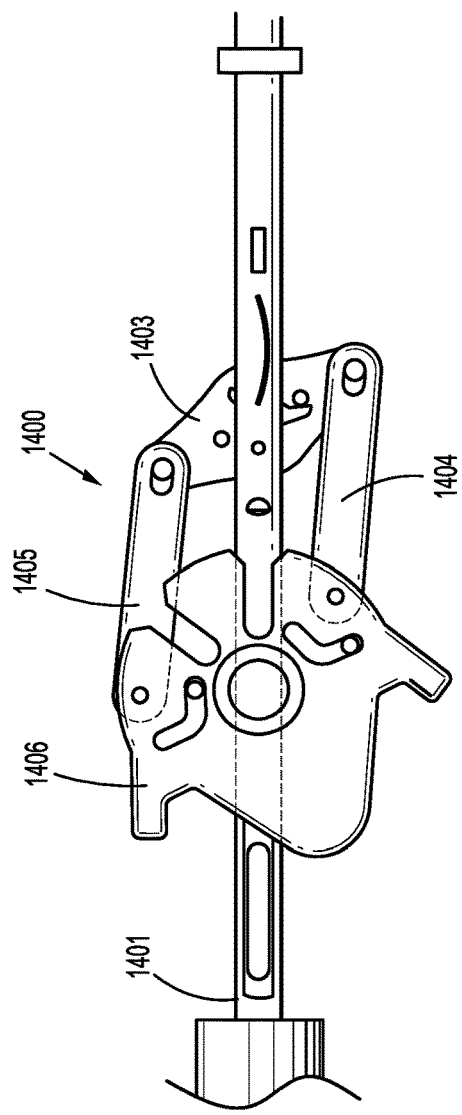
FIG. 47 is partial, top view of the drive conversion assembly of FIG. 43, illustrating reversal of a pivot block.
Figure 48:
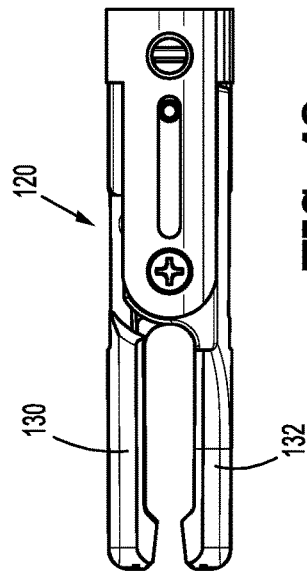
FIG. 48 is another top view of the tool assembly of FIG. 46, illustrating the jaws in the closed position.
Figure 49:
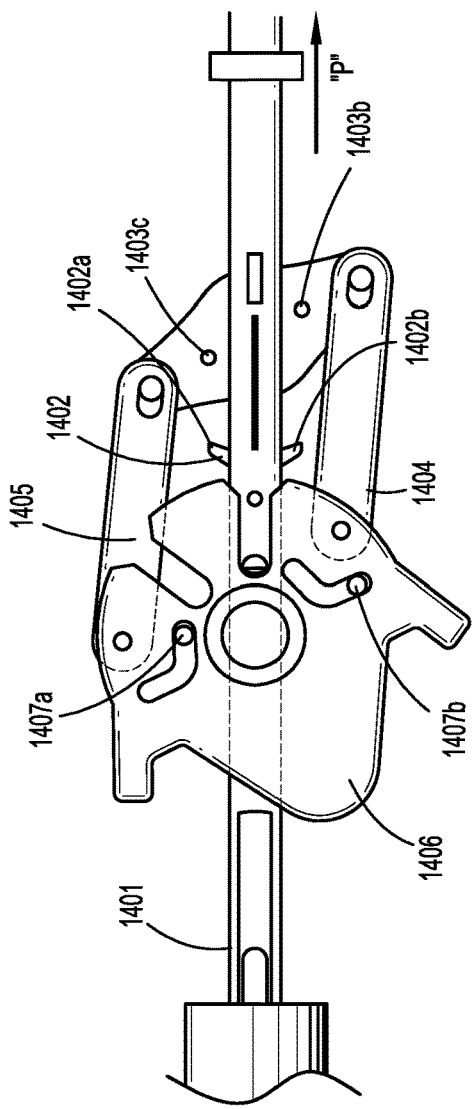
FIG. 49 is a partial, top view of the drive conversion assembly of FIG. 43, illustrating axial displacement of the main rod in a distal direction.
Figure 50:
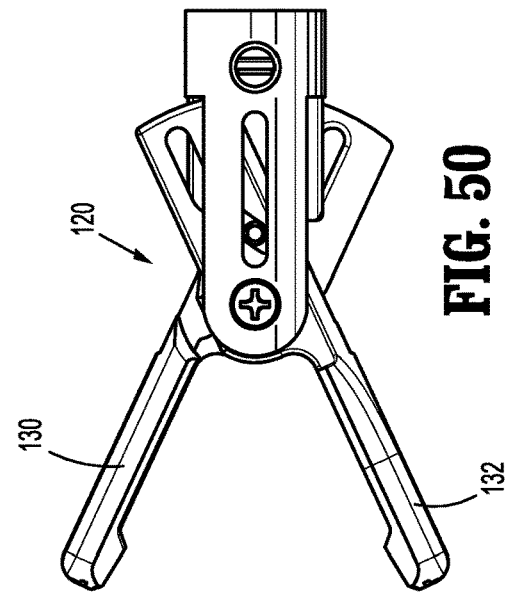
FIG. 50 is a top view of the tool assembly of FIG. 44, illustrating the jaws in the open position.
Figure 51:
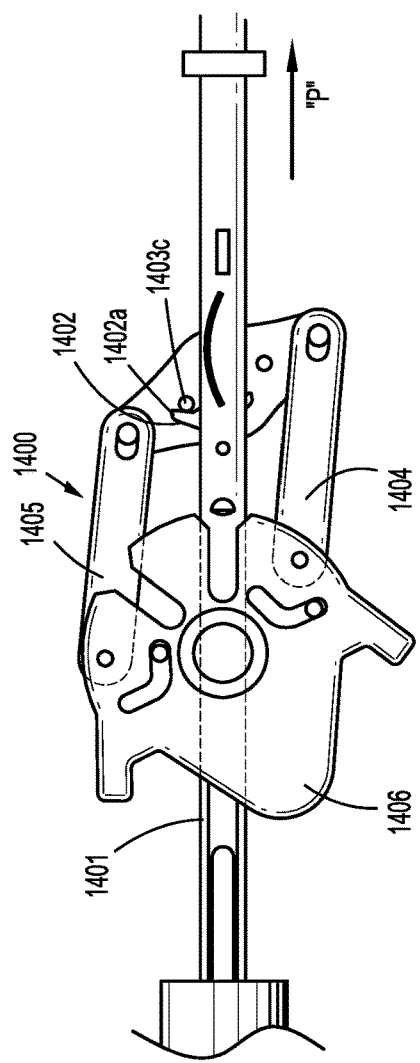
FIG. 51 is a partial, top view of the drive conversion assembly of FIG. 43, illustrating axial displacement of the main rod in the proximal direction.
Figure 52:
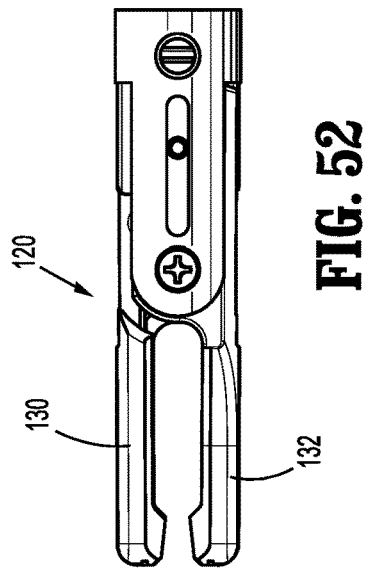
FIG. 52 is a top view of the tool assembly of FIG. 44, illustrating the jaws in the closed position.
Figure 53:
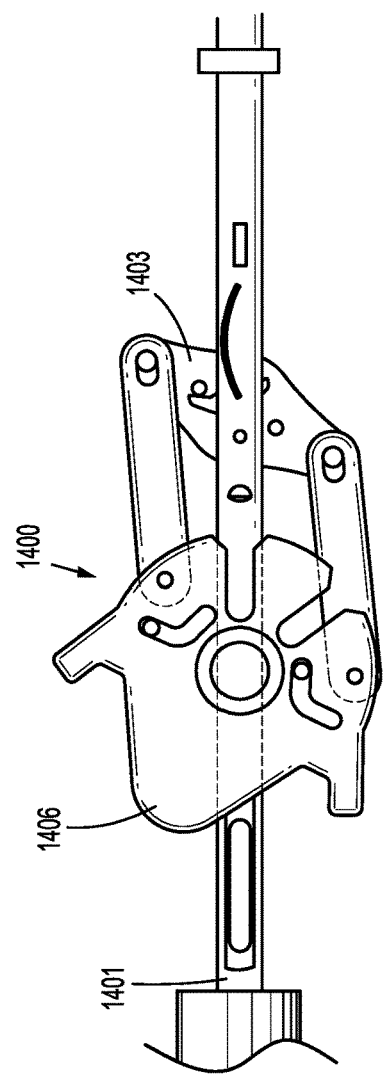
FIG. 53 is a partial, top view of the drive conversion assembly of FIG. 43, illustrating rotation of the pivot block.
Figure 54:
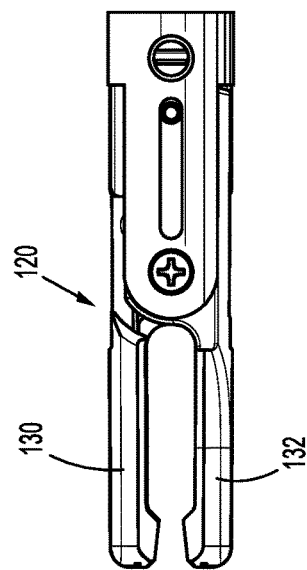
FIG. 54 is a top view of the tool assembly of FIG. 44, illustrating the jaws in a closed position.

With reference to FIGS. 43-46, initially, jaws 130, 132 are in an open position and cam wheel 1406 is in an initial orientation. When handles 110 (FIG. 1) are squeezed, main rod 1401 advances in the direction of arrow "p", which transitions jaws 130, 132 to the closed position (FIG. 46). With reference to FIGS. 45-48, continued advancement of main rod 1401 in the proximal direction "p" causes side 1402b of pawl 1402 to engage pin 1403b of pivot block 1403 (FIG. 45) and rotate pivot block 1403 (FIG. 47) such that links 1404, 1405 are displaced in opposite directions (FIG. 47). At this time, jaws 130, 132 of tool assembly 120 remain closed (FIG. 48). However, when the orientation of pivot block 1403 reverses (FIG. 47), blades 150, 152 (FIG. 5) in respective jaws 130, 132 move in opposite directions to enable swapping of needle 104 in jaws 130, 132. With reference to FIGS. 49 and 50, when handles 110 are released, main rod 1401 advances distally to the initial position, which, in turn, causes pawl 1402 to return to the initial position and orientation (FIG. 49). At this time, jaws 130, 132 are again in the open position (FIG. 50).

With reference now to FIGS. 51-54, in order to close jaws 130, 132 and swap needle 104 between jaws 130, 132, handles 110 are squeezed and main rod 1401 is moved proximally in the direction of arrow "p", which, in turn, enables side 1402a of pawl 1402 to engage pin 1403c. Engagement of side 1402a of pawl 1402 with pin 1403c rotates pivot block 1403, which, in turn, causes reciprocating displacement of links 1404, 1405 in opposite directions. In this manner, blades 150, 152 (FIG. 5) of tool assembly 120 move in opposite directions to enable swapping of needle 104 between jaws 130, 132 to move needle 104 and draw the suture (not shown) through tissue.

Under such a configuration, squeezing of handles 110 serves to open and close jaws 130, 132 and provide reciprocating displacement of blades 150, 152 of tool assembly 120 in opposite directions, which eliminates the need for a toggle mechanism.

The method of stitching target tissue has been described hereinabove and thus will not be described herein to avoid obscuring the present disclosure in unnecessary detail.

Figure 55:
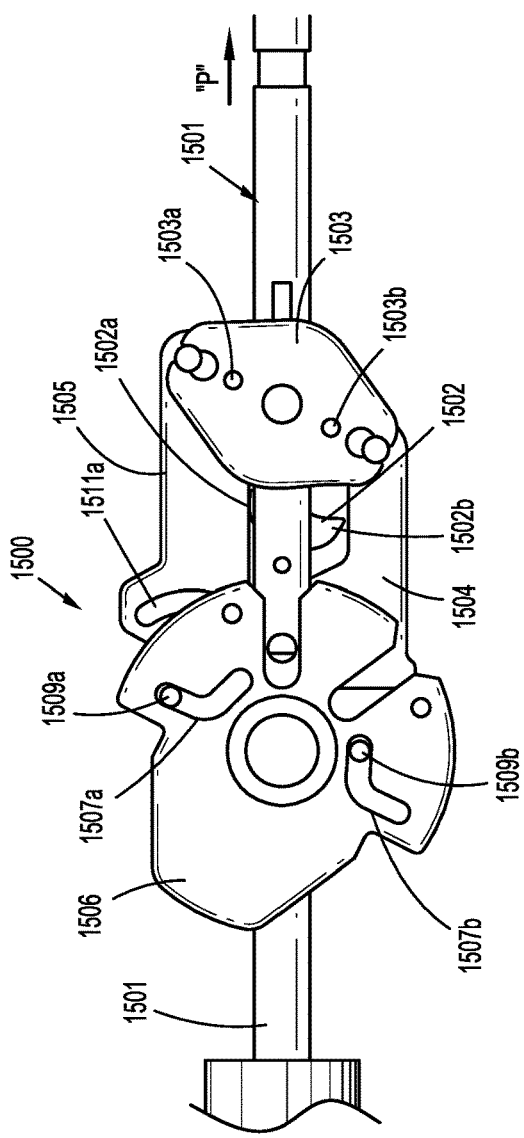
FIG. 55 is a partial, top view of a drive conversion assembly in accordance with another embodiment of the present disclosure.
Figure 56:
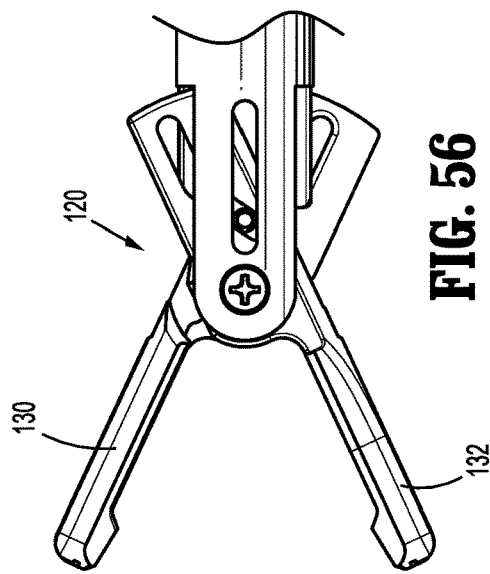
FIG. 56 is a top view of a tool assembly for use with the drive conversion assembly of FIG. 55, illustrating jaws thereof in an open position.

With reference now to FIGS. 55 and 56, there is illustrated a drive conversion assembly 1500 in accordance with an embodiment of the present disclosure for use with stitching device 1000. Drive conversion assembly 1500 includes features that are identical to the features described with respect to drive conversion assembly 1400. Thus, the identical parts in drive conversion assembly 1500 will not be described herein to avoid obscuring the present disclosure in unnecessary detail.

Drive conversion assembly 1500 is configured to convert axial displacement of a main rod 1501 operatively coupled to jaws 130, 132 into both functions of opening and closing jaws 130, 132 and providing reciprocating axial advancement of blades 150, 152 (FIG. 5), thereby eliminating the need for a separate toggle mechanism to move blades 150, 152 in opposite directions.

Figure 57:
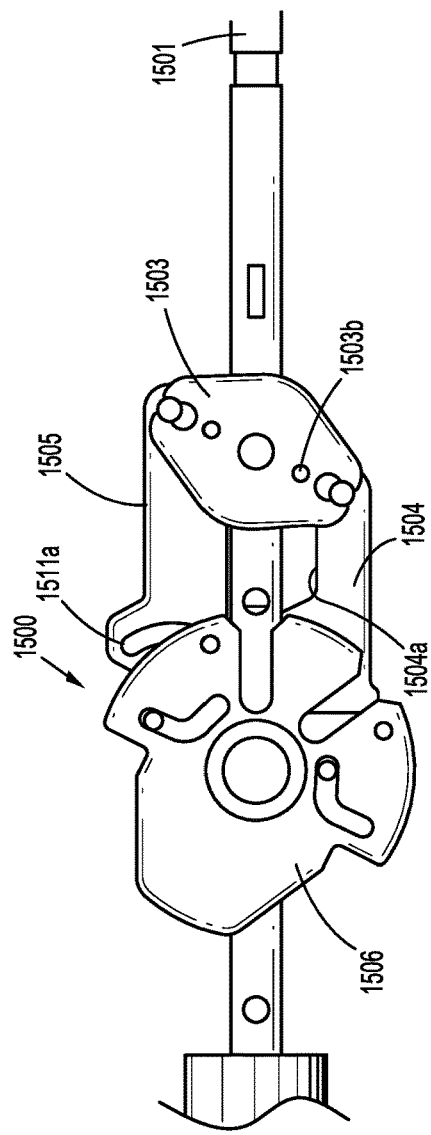
FIG. 57 is a partial, top view of the drive conversion assembly of FIG. 55, illustrating axial displacement of a main rod in a proximal direction.
Figure 59:
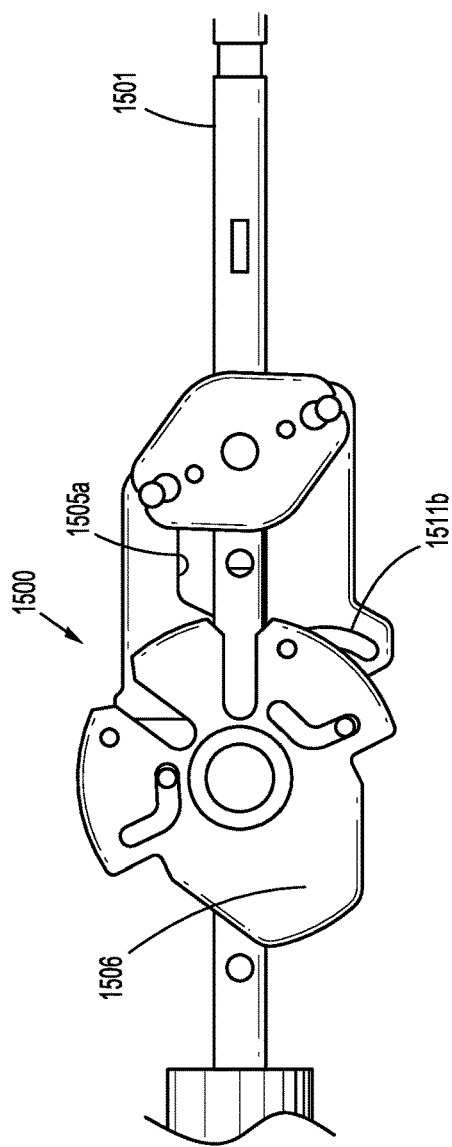
FIG. 59 is a partial, top view of the drive conversion assembly of FIG. 55, illustrating rotation of the pivot block.

Main rod 1501 may be coupled to handles 110 (FIG. 1), such that squeezing of handles 110 causes axial displacement of main rod 1501. Drive conversion assembly 1500 further includes a cam wheel 1506 defining camming slots 1507a, 1507b configured to receive camming pins 1509a, 1509b. Each camming slot 1507a, 1507b may define an L-shape. Camming pins 1509a, 1509b are secured with respective proximal ends of first and second blade drive members 480, 482 (FIG. 4) coupled to blades 150, 152 (FIG. 5) of tool assembly 120. Drive conversion assembly 1500 further includes links 1504, 1505 and a pivot block 1503 pivotally supported relative to main rod 1501. Links 1504, 1505 interconnect pivot block 1503 with cam wheel 1506. In particular, links 1504, 1505 define respective slots 1511a, 1511b (FIGS. 55 and 59). Slots 1511a, 1511b may extend transversely outward. Each slot 1511a, 1511b may include an arcuate profile. Drive conversion assembly 1500 further includes a pawl 1502 operatively coupled to main rod 1501. Opposing sides 1502a, 1502b of pawl 1502 extend transversely toward links 1504, 1505 when pawl 1502 is in a neutral position. Pawl 1502 is configured to engage one of pins 1503a, 1503b depending on the orientation of pivot block 1503. The transversely outward slots 1511a, 1511b (FIGS. 55 and 59) of links 1504, 1505 enable pawl 1502 to engage inner surfaces 1504a, 1505a (FIGS. 57 and 59) of respective links 1504, 1505, which may control the orientation of pawl 1502 during axial displacement of main rod 1501 to enable selective engagement of pawl 1502 with pins 1503a, 1503b. When pawl 1502 engages one of pins 1503a, 1503b, pivot block 1503 is rotated to cause reciprocating axial displacement of links 1504, 1505 in opposite directions (FIGS. 57 and 59).

Figure 58:
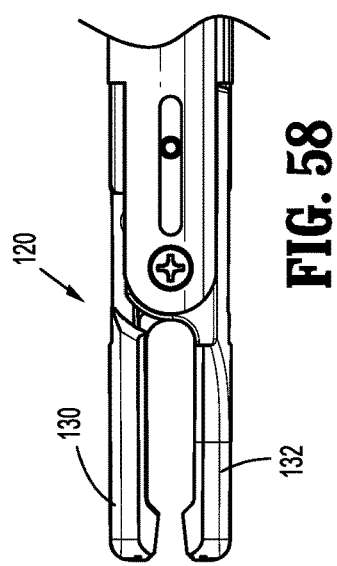
FIG. 58 is a top view of the tool assembly of FIG. 56, illustrating the jaws in a closed position.
Figure 60:
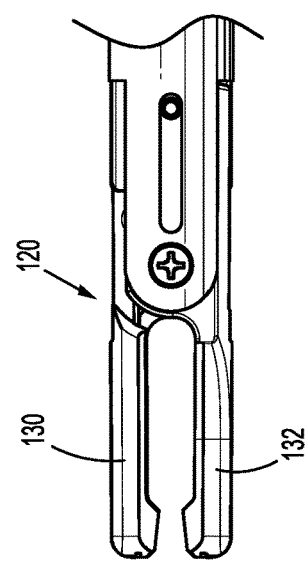
FIG. 60 is another top view of the tool assembly of FIG. 58, illustrating the jaws in the closed position.
Figure 61:
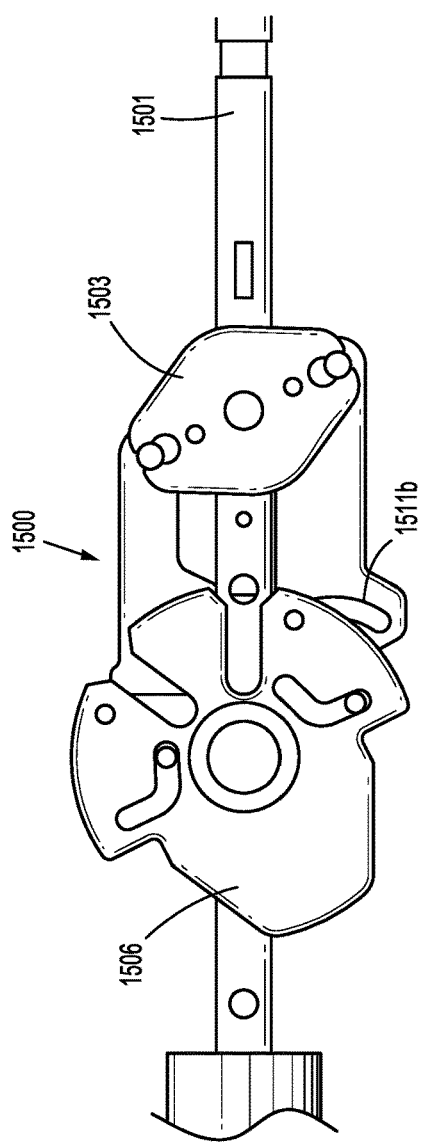
FIG. 61 is a partial, top view of the drive conversion assembly of FIG. 55, illustrating the main rod initiating axial displacement in the distal direction.
Figure 63:
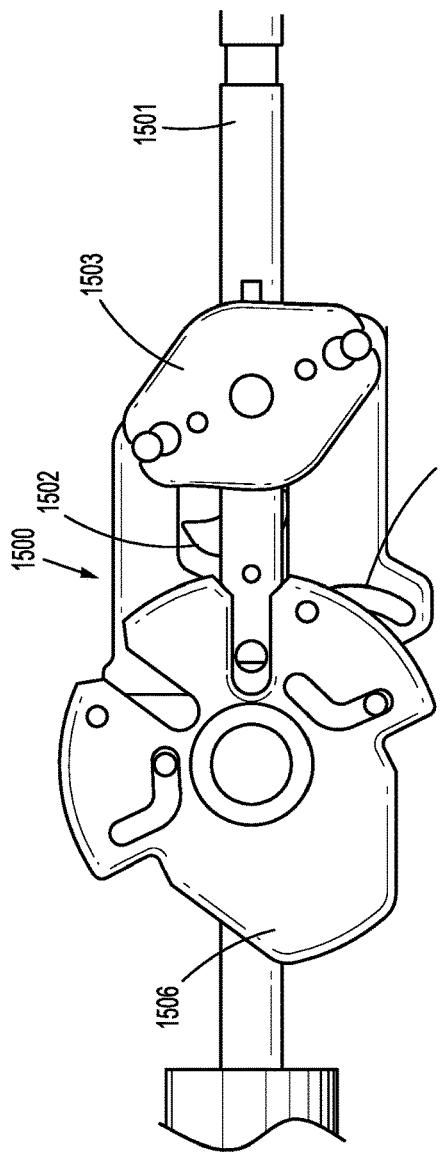
FIG. 63 is a partial, top view of the drive conversion assembly of FIG. 55, illustrating axial displacement of the main rod in the distal direction.
Figure 62:
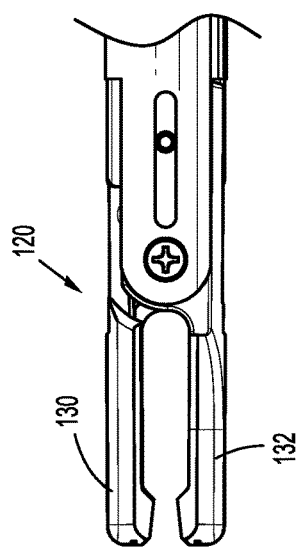
FIG. 62 is another top view of the tool assembly of FIG. 60, illustrating the jaws in the closed position.
Figure 64:
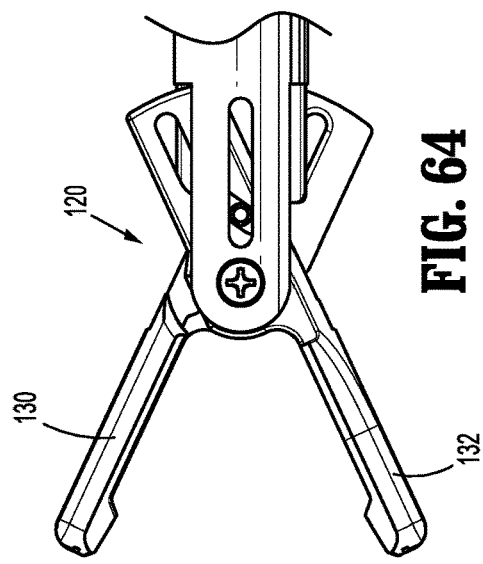
FIG. 64 is another top view of the tool assembly of FIG. 56, illustrating the jaws in the open position.

With reference to FIGS. 55 and 56, initially, jaws 130, 132 are in an open position and cam wheel 1506 is in a first orientation in which links 1504, 1505 are longitudinally displaced from each other. When handles 110 (FIG. 3) are squeezed, main rod 1501 is advanced in the direction of arrow "p". During axial displacement of main rod 1501, pawl 1502 may slide against inner surfaces 1504a, 1505a (FIGS. 57 and 59). With reference now to FIGS. 57-59, continued axial displacement of main rod 1501 causes pawl 1502 to engage pin 1503b (FIG. 57) of pivot block 1503 to reverse the orientation of pivot block 1503 (FIG. 59), which, in turn, reverses longitudinal displacement of links 1504, 1505. At this time, pawl 1502 may rotate to accommodate the rotation of pivot block 1503. At this time, jaws 130, 132 of tool assembly 120 remain closed (FIG. 60). However, when the orientation of pivot block 1503 reverses (FIG. 59), blades 150, 152 in respective jaws 130, 132 also move in opposite directions. With reference to FIGS. 63 and 64, when handles 110 are released, main rod 1501 moves distally to the initial position. At this time, jaws 130, 132 are again in the open position (FIG. 50).

In order to swap needle 104 from one jaw 130, 132 to the other jaw 130, 132, handles 110 may be squeezed again, which causes main rod 1501 to move proximally. At this time, the reoriented pawl 1502 engages pin 1503a (FIG. 55) of pivot block 1503 and causes rotation of pivot block 1503 in an opposite direction. Reciprocating axial displacement of links 1504, 1505 causes cam wheel 1506 to rotate back to the first orientation (FIG. 55). Rotation of cam wheel 1506 causes reciprocating axial displacement of blades 150, 152 in opposite directions. In this manner, squeezing of handles 110 serves to open and close jaws 130, 132 and to provide axial displacement of blades 150, 152 of tool assembly 120 in opposite directions. As a result, the need for a toggle mechanism including a manually operated lever, is eliminated. The method of stitching target tissue has been described hereinabove and thus will not be described herein to avoid obscuring the present disclosure in unnecessary detail.

In accordance with another embodiment of the present disclosure, there is illustrated a drive conversion assembly 1600 for use with stitching device 1000. With reference to FIG. 65, drive conversion assembly 1600 is configured to convert axial displacement of main rod 156 into both functions of opening and closing jaws 130, 132 and providing reciprocating axial displacement of blades 150, 152, thereby eliminating the need for a separate toggle mechanism to move blades 150, 152 (FIG. 5) in opposite directions.

As discussed hereinabove, main rod 156 is coupled to handles 110 (FIG. 1), such that squeezing of handles 110 causes axial displacement of main rod 156 in the direction of an arrow "p". Drive conversion assembly 1600 includes a cam wheel 1606 defining camming slots 1607a, 1607b configured to receive camming pins (not shown) secured with first and second blade drive members 480, 482 (FIG. 4) coupled with respective blades 150, 152 (FIG. 5). Drive conversion assembly 1600 further includes first and second pins 1603a, 1603b and a reset pin 1603c. First and second pins 1603a, 1603b are adjacent respective slots 1607a, 1607b. For example, first and second pins 1603a, 1603b may be disposed radially inward of respective slots 1607a, 1607b. In addition, first and second pins 1603a, 1603b may diametrically oppose each other. Drive conversion assembly 1600 further includes a pawl 1602 operatively coupled to main rod 156. Pawl 1602 may be biased to a neutral position by a biasing member 1609.

Pawl 1602 includes opposing sides 1602a (FIG. 69), 1602b (FIG. 65) extending transversely outward from main rod 156 based on the orientation of the cam wheel 1606. Opposing sides 1602a, 1602b of pawl 1602 are configured to engage respective first and second pins 1603a, 1603b, as well as reset pin 1603c, to cause rotation of cam wheel 1606, thereby providing reciprocating axial displacement of first and second blade drive members 480, 482 in opposite directions.

When stitching device 1000 is in the suture mode, jaws 130, 132 are in the open position. When handles 110 (FIG. 1) are squeezed, main rod 156 advances in the direction of arrow "p", which transitions jaws 130, 132 to the closed position. With reference to FIG. 66, continued advancement of main rod 156 in the proximal direction "p" causes side 1602b of pawl 1602 to engage second pin 1603b and rotate cam wheel 1606 such that first and second blade drive members 480, 482 are displaced in opposite directions (FIG. 67). As a result, blades 150, 152 (FIG. 5) in respective jaws 130, 132 move in opposite directions to enable swapping of needle 104 in jaws 130, 132. At this time, jaws 130, 132 of tool assembly 120 remain closed.

Figure 69:
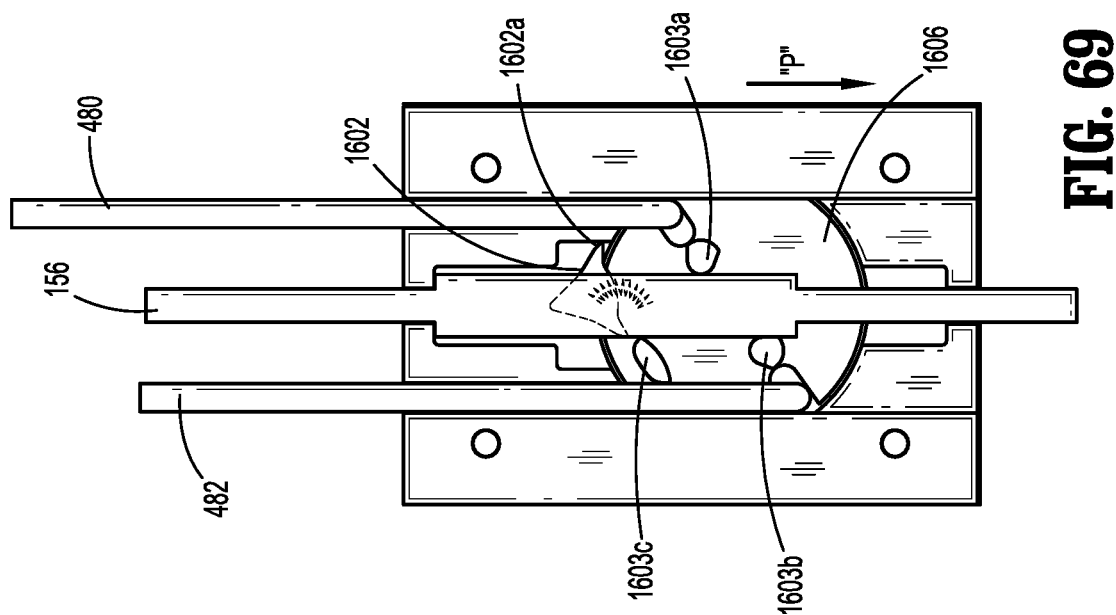
Figure 68:
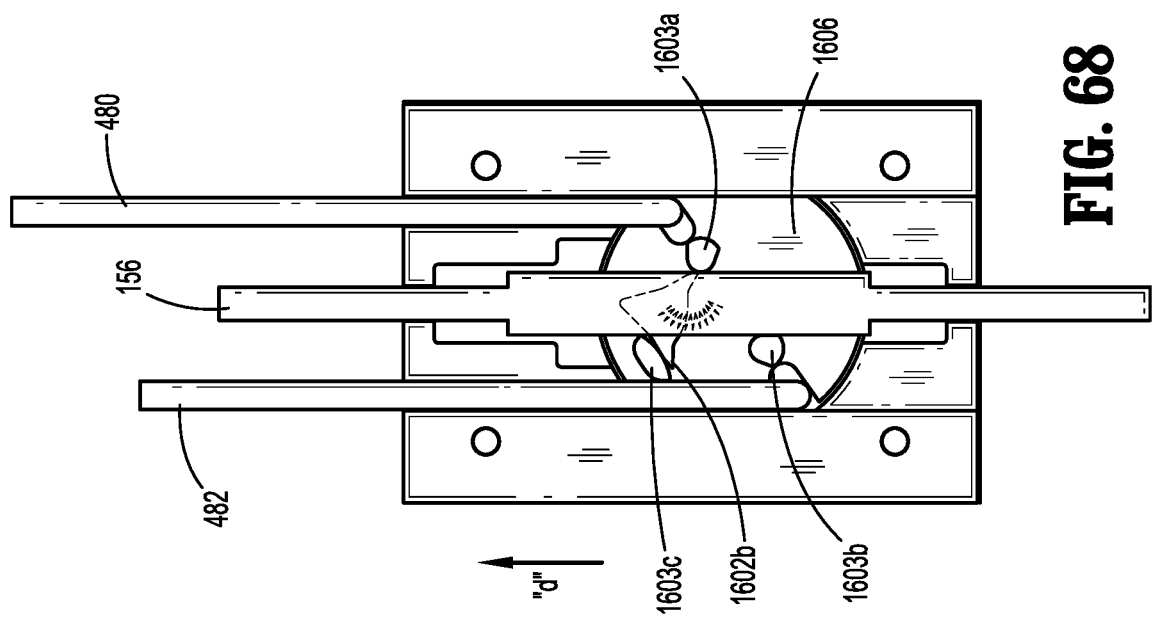

With reference to FIG. 68, when handles 110 are released, main rod 156 advances distally in the direction of arrow "d", which, in turn, causes pawl 1602 to engage reset pin 1603c. Reset pin 1603c urges pawl 1602 distally and further positions opposing side 1602a (FIG. 69) of pawl 1602 to transversely extend out of main rod 156 (FIG. 69). This enables main rod 156 to return to the initial position. At this time, jaws 130, 132 are again in the open position.

In order to close jaws 130, 132 and swap needle 104 between jaws 130, 132, handles 110 are squeezed and main rod 156 is moved proximally in the direction of arrow "p", which, in turn, enables side 1602a of pawl 1602 to this time engage first pin 1603a. Engagement of side 1602a of pawl 402 with first pin 1603a rotates cam wheel 1606, which, in turn, causes reciprocating displacement of first and second blade drive members 480, 482 in opposite directions. In this manner, blades 150, 152 (FIG. 5) of tool assembly 120 move in opposite directions to enable swapping of needle 104 between jaws 130, 132, thereby moving needle 104 and drawing the suture (not shown) through tissue. When handles 110 are released, main rod 156 advances distally in the direction of arrow "d" to the initial position, which, in turn, causes pawl 1602 to engage reset pin 1603c. Reset pin 1603c urges pawl 1602 distally and further positions side 1602b of pawl 1602 (FIG. 65) to transversely extend out of main rod 156. At this time, jaws 130, 132 are again in the open position.

Under such a configuration, squeezing of handles 110 serves to open and close jaws 130, 132 and provide reciprocating displacement of blades 150, 152 of tool assembly 120 in opposite directions, which eliminates the need for a manually operated lever.

Figure 70:
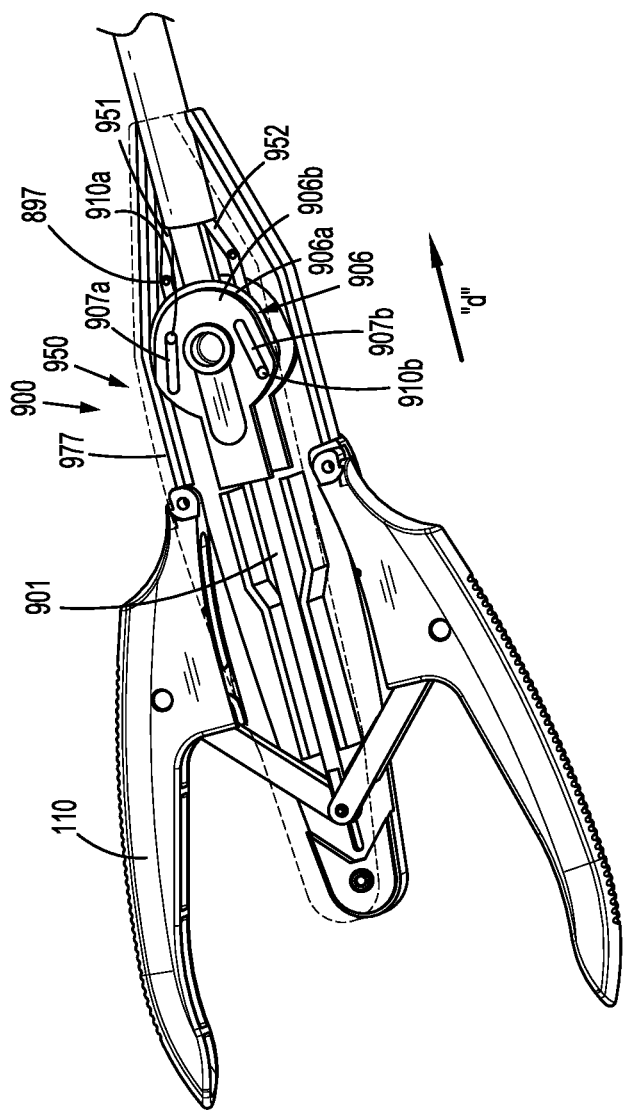
FIG. 70 is a partial, perspective view of a handle assembly including a drive conversion assembly in accordance with another embodiment of the present disclosure.

The method of stitching target tissue has been described hereinabove and thus will not be described herein to avoid obscuring the present disclosure in unnecessary detail. In accordance with another embodiment of the present disclosure as illustrated in FIG. 70, there is illustrated a handle assembly 900 for use with stitching device 1000. Handle assembly 900 includes a drive conversion assembly 950.

Drive conversion assembly 950 includes features that are identical to previously described drive conversion assemblies 400, 600, 700, 800, 1100, 1400, 1500, 1600. Identical constructions will not be described in detail to avoid obscuring the present disclosure in unnecessary detail.

With continued reference to FIG. 70, drive conversion assembly 950 is configured to convert axial displacement of a main rod 901 operatively coupled to jaws 130, 132 (FIG. 1) into two reciprocating motions of blades 150, 152 (FIG. 5) of tool assembly 120. In this manner, axial displacement of main rod 901 effects both functions of opening and closing jaws 130, 132 and providing reciprocating axial advancement of blades 150, 152, thereby eliminating the need for a separate toggle mechanism, to move blades 150, 152 (FIG. 5) in opposite directions.

Main rod 901 may be operatively coupled to handles 110, whereby squeezing of handles 110 causes axial displacement of main rod 901. Drive conversion assembly 950 is selectively transitionable between an operational mode and a reload mode. When in the operational mode, squeezing of handles 110 opens and closes jaws 130, 132 and causes reciprocating axial displacement of blades 150, 152 of tool assembly 120 such that needle 104 (FIG. 5) may be swapped between jaws 130, 132. In the reload mode, jaws 130, 132 are in the open position and blades 150, 152 are positioned such that needle 104 may be loaded into one of jaws 130, 132. Drive conversion assembly 950 transitions from the operational mode to the reload mode by advancing cam wheel assembly 906 distally in a direction of an arrow "d" in order to position blades 150, 152 to receive insertion of needle 104 to one of jaws 130, 132. It is contemplated that hub 997 may be provided with a slider or a button (not shown) to advance cam wheel assembly 906 distally to the reload mode.

With continued reference to FIG. 70, cam wheel assembly 906 includes a base portion 906a and a coupling portion 906b. Base portion 906a includes camming slots (not shown), and coupling portion 906b defines camming slots 907a, 907b. Camming pins 910a, 910b ride in the respective camming slots (not shown) of base portion 906a and respective camming slots 907a, 907b of coupling portion 906b. Drive conversion assembly 950 further includes first and second blade drive members 951, 952 operatively coupling cam wheel assembly 906 with blades 150, 152 (FIG. 5) of tool assembly 120 (FIG. 2).

Figure 71:
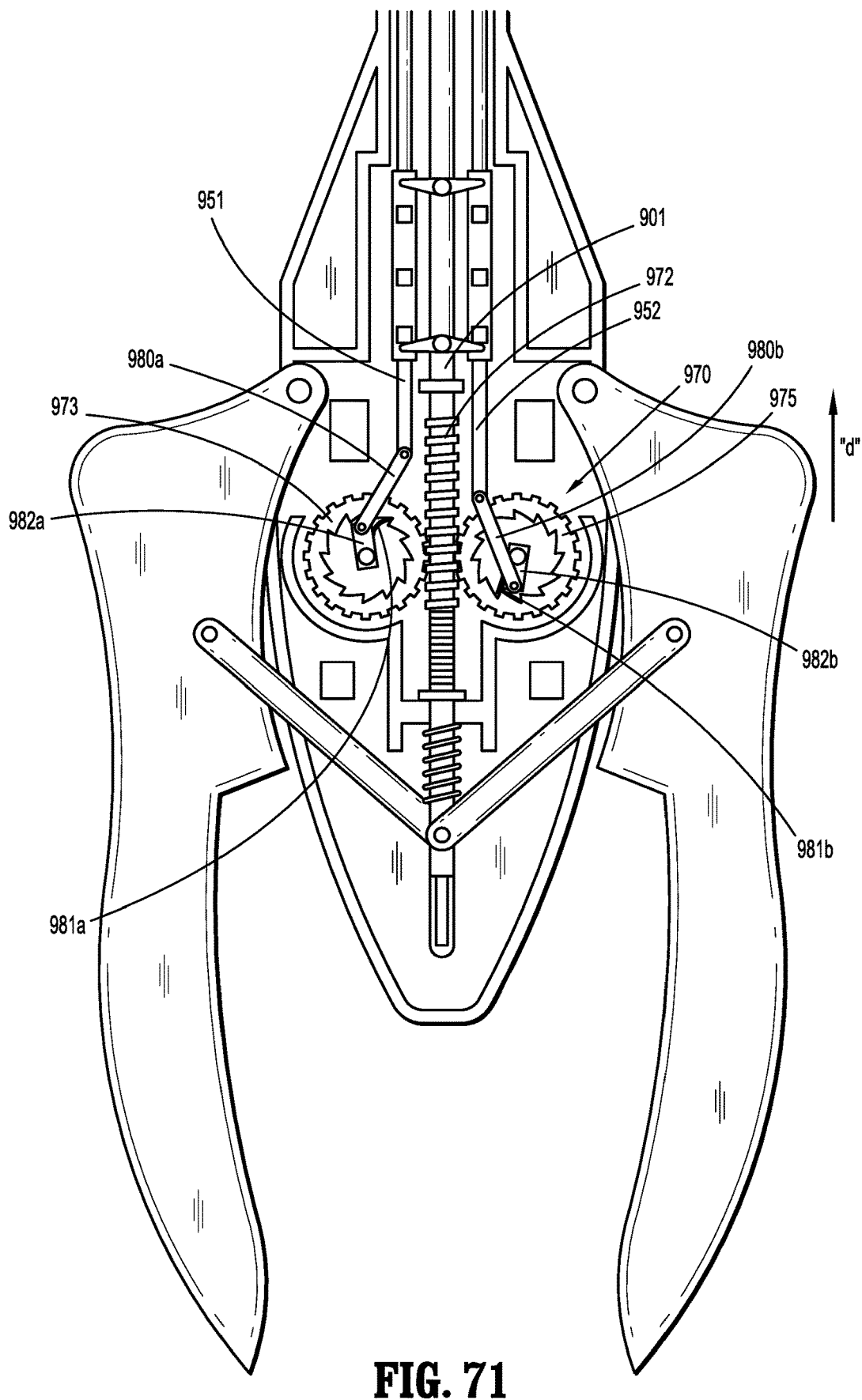
FIG. 71 is a partial cross-sectional view of the handle assembly of FIG. 70.

With reference now to FIG. 71, cam wheel assembly 906 may include a worm gear assembly 970. Worm gear assembly 970 includes first and second gears 973, 975. Main rod 901 may include a worm gear portion 972. Worm gear portion 972 is interposed between first and second gears 973, 975 such that axial displacement or rotation of worm gear 972 causes rotation of first and second gears 973, 975 in opposite directions. Worm gear assembly 970 further includes connecting links 980a, 980b pivotally connected to respective first and second blade drive members 951, 952. Connecting links 980a, 980b are pivotably coupled to respective rotating links 982a, 982b. Rotating links 982a, 982b are pivotably disposed about respective first and second gears 973, 975. In addition, each of rotating links 982a, 982b includes an engaging portion 981a, 981b configured to engage inner surfaces of respective first and second gears 973, 975. The inner surfaces of respective first and second gears 973, 975 includes cutouts or teeth that serve as ratchet mechanisms to limit the direction of rotation of rotating links 982a, 982b to a single direction. Under such a configuration, rotation of first and second gears 973, 975 causes reciprocating axial displacement of first and second blade drive members 951, 952 in opposite directions.

Accordingly, in use, when handles 110 are squeezed, main rod 901 is advanced distally in the direction of an arrow "d" and causes rotations of first and second gears 973, 975, which, in turn, causes reciprocating axial displacement of blades 150, 152 of tool assembly 120 in opposite directions. When handles 110 are released, main rod 901 returns to the initial position, without affecting the orientation of first and second gears 973, 975 or axial displacement of blades 150, 152. It is also envisioned that squeezing of handles 110 may rotate main rod 901 by using, e.g., a worm gear assembly, to eliminate the need for resetting main rod 901 to the initial position before initiating the next cycle or reversal of blades 150, 152.

In use, cam wheel assembly 906 is moved distally to load needle 104 in one of jaws 130, 132. Thereafter, handles 110 are squeezed to transition cam wheel assembly 906 to the operational mode. Handles 110 are squeezed again to advance main rod 901 proximally which rotates first and second gears 973, 975. Rotation of first and second gears 973, 975 causes rotation of cam wheel assembly 906 and provides reciprocating axial displacement of first and second blade drive members 951, 952, which, in turn, causes reciprocating axial displacement of blades 150, 152 of tool assembly 120. When handles 110 are released, main rod 901 is retracted to the initial position in the direction of arrow "d". At this time, handles 110 may be squeezed again to reverse the position of blades 150, 152 in order to swap needle 104 to the other jaw 130, 132. Such a configuration eliminates the need for a separate toggle mechanism, to move blades 150, 152 (FIG. 5) in opposite directions. The method of stitching target tissue has been described hereinabove and thus will not be described herein to avoid obscuring the present disclosure in unnecessary detail.

Although the illustrative embodiments of the present disclosure have been described herein with reference to the accompanying drawings, the above description, disclosure, and figures should not be construed as limiting, but merely as exemplifications of particular embodiments. For example, elongate shaft assembly 170 may include an articulable section to facilitate maneuverability of stitching device through the anatomical structure of the patient. It is to be understood, therefore, that the disclosure is not limited to those precise embodiments, and that various other changes and modifications may be effected therein by one skilled in the art without departing from the scope or spirit of the disclosure.

What is claimed is:

1. An endoscopic stitching device, comprising:
    a handle assembly including:
        a main rod configured for axial displacement; and
        a drive conversion assembly including:
            a cam wheel;
            a pivot block;
            first and second links interconnecting the pivot block with the cam wheel;
            a pawl operatively coupled to the main rod, the pawl configured to engage the pivot block to rotate the pivot block which, in turn, causes reciprocating displacement of the first and second links;
            third and fourth links operatively coupled with the cam wheel; and
            a pusher operatively coupled to the main rod, the pusher engaging the third link to exert force on the cam wheel; and
    an elongate shaft assembly including:
        first and second blade drive members; and
        a tool assembly including:
            first and second jaws operatively coupled with the main rod of the handle assembly; and
            first and second blades slidably disposed in the respective first and second jaws, the first and second blades operatively coupled with the first and second blade drive members, respectively, wherein axial displacement of the main rod transitions the first and second jaws between open and closed positions and causes reciprocating axial displacement of the first and second blades.

2. The endoscopic stitching device according to claim 1, wherein the pusher includes a cutout portion configured to receive the third link such that the third link is aligned with the main rod.

3. The endoscopic stitching device according to claim 1, wherein the cam wheel includes a base portion and a coupling portion cammingly coupled with the base portion, wherein the first and second blade drive members are cammingly coupled with the base portion.

4. The endoscopic stitching device according to claim 3, wherein the first and second links are cammingly coupled to the base portion of the cam wheel.

5. The endoscopic stitching device according to claim 3, wherein the coupling portion of the cam wheel includes a pair of opposing slots, the pair of opposing slots extending distally inward.

6. The endoscopic stitching device according to claim 3, wherein the base portion of the cam wheel defines a pair of opposing slots extending transversely outward with respect to the main rod.

7. The endoscopic stitching device according to claim 1, wherein the drive conversion assembly further includes a fifth link pivotally supported such that when the main rod is advanced proximally, the pusher pushes the fifth link to position the third and fourth links in alignment with the main rod.

8. The endoscopic stitching device according to claim 1, wherein the pusher defines a cutout having an arcuate portion configured to receive the third link therein.

9. The endoscopic stitching device according to claim 1, wherein the cam wheel is transitionable between a proximal position in which the first and second links are movable to effect axial displacement thereof and a distal position in which both of the first and second blades are in distal positions to receive a needle.

10. The endoscopic stitching device according to claim 1, wherein the pusher defines a U-shaped cutout.

11. The endoscopic stitching device according to claim 1, wherein the third link includes a camming pin that rides along a camming slot defined in the main rod.

12. The endoscopic stitching device according to claim 1, wherein the cam wheel of the drive conversion assembly includes a lock out pin and the main rod includes an engaging pin configured to inhibit axial movement of the main rod when the lock out pin and the engaging pin engage each other in alignment.

13. An endoscopic stitching device, comprising:
    an elongate shaft assembly including:
        first and second blade drive members; and
        a tool assembly including:
            first and second jaws; and
            first and second blades slidably disposed in the respective first and second jaws, the first and second blades operatively coupled with the first and second blade drive members, respectively; and
a handle assembly including:
a main rod configured for axial displacement; and
a drive conversion assembly operatively coupled with the first and second blade drive members, the drive conversion assembly including:
a cam wheel including first, second, and third pins; and
a pawl operatively coupled to the main rod, the pawl configured to engage the first pin to cause rotation of the cam wheel in a first direction which, in turn, causes reciprocating displacement of the first and second blade drive members, and the second pin to cause rotation of the cam wheel in a second direction, which, in turn, causes reciprocating displacement of the first and second blade drive members in opposite directions, the pawl configured to engage the third pin to cause the pawl to extend transversely outward of the main rod away from the third pin, wherein axial displacement of the main rod pivots the first and second jaws between open and closed positions and causes reciprocating axial displacement of the first and second blades.

14. The endoscopic stitching device according to claim 13, wherein the first and second pins diametrically oppose each other.

15. The endoscopic stitching device according to claim 13, wherein the first and second pins are disposed adjacent the first and second blade drive members, respectively.

16. The endoscopic stitching device according to claim 13, wherein the pawl is coupled to a biasing member.

* * * * *